United States Patent
Evans et al.

(10) Patent No.: US 7,335,677 B2
(45) Date of Patent: Feb. 26, 2008

(54) INHIBITORS OF DIPEPTIDYL PEPTIDASE IV

(75) Inventors: David M. Evans, Southampton (GB); Doreen M. Ashworth, Southampton (GB)

(73) Assignee: Ferring B.V., Hoofddorp (NL)

(*) Notice: Subject to any disclaimer, the term of this patent is extended or adjusted under 35 U.S.C. 154(b) by 240 days.

(21) Appl. No.: 10/491,794

(22) PCT Filed: Oct. 23, 2002

(86) PCT No.: PCT/GB02/04764

§ 371 (c)(1),
(2), (4) Date: Oct. 12, 2004

(87) PCT Pub. No.: WO03/035057

PCT Pub. Date: May 1, 2003

(65) Prior Publication Data

US 2005/0043299 A1 Feb. 24, 2005

(30) Foreign Application Priority Data

Oct. 23, 2001 (GB) ............................ 0125445.7

(51) Int. Cl.
*C07D 401/12* (2006.01)
*C07D 403/12* (2006.01)
*A61K 31/4025* (2006.01)

(52) U.S. Cl. .................... 514/408; 548/530; 548/540; 546/150; 546/164; 546/208; 514/213.01; 514/217.08; 514/307; 514/314; 514/326; 540/476; 540/480

(58) Field of Classification Search ............... 548/530, 548/540; 514/408
See application file for complete search history.

(56) References Cited

U.S. PATENT DOCUMENTS

| 6,011,115 A | 1/2000 | Miharu |
| 6,011,155 A * | 1/2000 | Villhauer .................... 544/333 |

FOREIGN PATENT DOCUMENTS

| DE | 4344648 A1 * | 6/1995 |
| EP | 490379 A2 * | 6/1992 |

OTHER PUBLICATIONS

Alexander, J., et al. "(Acyloxy)alkyl Carbamates as Novel Bioreversible Prodrugs for Amines: Incresed Permeation through Biological Membranes", J. Med. Chem., vol. 31, pp. 318-322 (1988).

* cited by examiner

*Primary Examiner*—Kahsay Habte
(74) *Attorney, Agent, or Firm*—Foley & Lardner LLP

(57) ABSTRACT

Novel compounds that are inhibitors of one or most post-proline cleaving proteases, e.g. dipeptidyl peptidase IV, according to general formula (1). $R^1$ is H or CN, $X^1$ is O, S, $CH_2$, CHF, $CF_2$, $CH(CH_3)$, $C(CH_3)_2$ or CH(CN), and b is 1 or 2. $G^1$ is H or a group according to the formula —$CH^2$—$X^2$—$(CH_2)_a$-$G^3$ and $G^2$ is H or a group according to the formula —$CH_2$—$(CH_29_a$-$G^3$, provided that one of $G^1$ and $G^2$ is H and the other is not H. $X^2$ is O, S, or $CH_2$, and a is 0, 1 or 2, provided that when a is 1 then $X_2$ is $CH_2$. $G^3$ is a group according to one of general formulae 2-4, where the variables have meaning given in the description. The compounds are useful in the treatment of i.a. type 2 diabetes and impaired glucose tolerance (1)

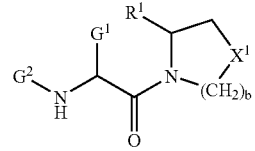

(2)

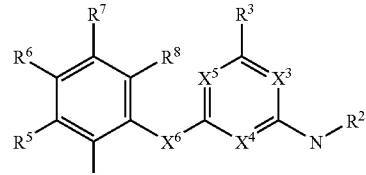

(3)

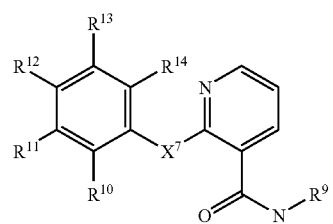

(4)

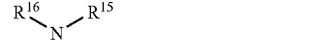

(5)

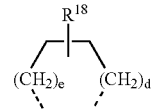

(6)

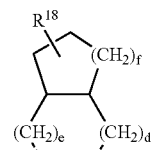

(7)

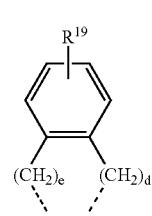

7 Claims, No Drawings

INHIBITORS OF DIPEPTIDYL PEPTIDASE IV

The present invention relates to novel compounds that are inhibitors of post-proline aminopeptidases. The compounds are useful as antiproliferative agents and in the treatment of, inter alia, type 2 diabetes and impaired glucose tolerance.

BACKGROUND

The enzyme dipeptidyl peptidase IV, herein abbreviated DP-IV (and elsewhere as DAP-IV or DPP-IV) and also known by the classification EC.3.4.14.5, is a serine protease that cleaves the N-terminal dipeptide from peptides that begin with the sequence H-Xaa-Pro (where Xaa is any amino acid, although preferably a lipophilic one, and Pro is proline). It will also accept as substrates peptides that begin with the sequence H-Xaa-Ala (where Ala is alanine). DP-IV was first identified as a membrane-bound protein. More recently a soluble form has been identified.

Initial interest in DP-IV focussed on its role in the activation of T lymphocytes. DP-IV is identical to the T cell protein CD26. It was proposed that inhibitors of DP-IV would be capable of modulating T cell responsiveness, and so could be developed as novel immunomodulators. It was further suggested that CD26 was a necessary co-receptor for HIV, and thus that DP-IV inhibitors could be useful in the treatment of AIDS.

Attention was given to the role of DP-IV outside the immune system. It was recognised that DP-IV has a key role in the degradation of several peptide hormones, including growth hormone releasing hormone (GHRH) and glucagon-like peptide-1 and -2 (GLP-1 and GLP-2). Since GLP-1 is known to have a potentiating effect on the action of insulin in the control of post-prandial blood glucose levels it is clear that DP-IV inhibitors might also be usefully employed in the treatment of type II diabetes and impaired glucose tolerance. At least two DP-IV inhibitors are currently undergoing clinical trials to explore this possibility.

Several groups have disclosed inhibitors of DP-IV. While some leads have been found from random screening programs, the majority of the work in this field has been directed towards the investigation of substrate analogues. Inhibitors of DP-IV that are substrate analogues are disclosed in, for example, U.S. Pat. Nos. 5,462,928, 5,543,396, WO95/15309 (equivalent to U.S. Pat. No. 5,939,560 and EP 0731789), WO98/19998 (equivalent to U.S. Pat. No. 6,011,155), WO99/46272 and WO99/61431.

More recently a number of proteins have been found that share some of the enzymatic properties of DP-IV. Some, such as FAP and DPP-8, have sequence homology with DP-IV, while others, such as QPP, have no such homology but nevertheless mimic the aminodipeptidase activity of DP-IV. The physiological function of these newer proteases is still being investigated. FAP has been implicated in invasive processes such as cancer metastasis and endometriosis, and QPP appears to be involved in immune-cell apoptosis. It is also possible that some of these proteases share a common function. This redundancy would allow continuing normal physiological function in the event of a failure in the expression or function of one of the proteases.

In order to further define the roles of these newer proteases it is important to have the tools to manipulate selectively each one or the whole class. Therefore there exists a need for specific and potent inhibitors of each of these proteases, and also for potent non-specific inhibitors of the class of post-proline cleaving aminodipeptidases.

SUMMARY OF THE INVENTION

We disclose herein a series of novel compounds that are inhibitors of one or more post-proline cleaving proteases, and specifically compounds according to general formula 1.

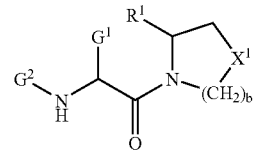

1

In general formula 1, $R^1$ is H or CN, $X^1$ is O, S, $CH_2$, CHF, $CF_2$, $CH(CH_3)$, $C(CH_3)_2$ or CH(CN), and b is 1 or 2. $G^1$ is H or a group according to the formula —$CH^2$—$X^2$—$(CH_2)_a$-$G^3$ and $G^2$ is H or a group according to the formula —$CH_2$—$(CH_2)_a$-$G^3$, provided that one of $G^1$ and $G^2$ is H and the other is not H. $X^2$ is O, S or $CH_2$, and a is 0, 1 or 2, provided that when a is 1 then $X^2$ is $CH_2$. $G^3$ is a group according to one of general formulae 2-4.

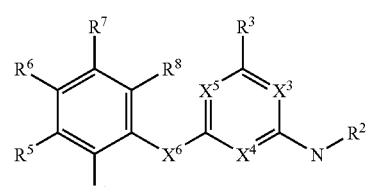

2

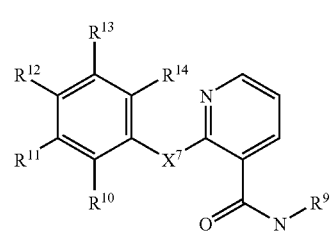

3

4

$X^3$, $X^4$ and $X^5$ are either nitrogen N or CH, provided that at least two of $X^3$, $X^4$ and $X^5$ are N. $X^6$ is either O or NH. $R^2$ is either H or alkyl. $R^3$ is selected from H, Cl, OH, O-alkyl, $NH_2$, NH-alkyl and $N(alkyl)_2$. $R^4$, $R^5$, $R^6$, $R^7$ and $R^8$ are selected from H, Br, Cl, F, $CF_3$, alkyl, acyl, OH, O-alkyl, $NH_2$, NH-alkyl, $N(alkyl)_2$, $NO_2$, NH-acyl, $CO_2H$, $CO_2$-alkyl, $CONH_2$, CONH-alkyl, $CON(alkyl)_2$ and CN. $X^7$ is $CH_2$, O, S or NH. $R^9$ is either H or alkyl. $R^{10}$, $R^{11}$, $R^{12}$, $R^{13}$ and $R^{14}$ are selected from H, Br, Cl, F, $CF_3$, alkyl, acyl, OH, O-alkyl, $NH_2$, NH-alkyl, $N(alkyl)_2$, $NO_2$, NH-acyl, $CO_2H$, $CO_2$-alkyl, $CONH_2$, CONH-alkyl, $CON(alkyl)_2$ and CN. $R^{15}$ and $R^{16}$ are each independently H, alkyl, alkenyl, polyfluoroalkyl, aralkyl, aryl or $CH_2$-L-$R^{17}$, where L is a covalent bond, CH=CH, C≡C or —$C_6H_4$—, and $R^{17}$ is H, alkyl or aryl, or $R^{15}$ and $R^{16}$ together are a group according to one of general formulae 5-7.

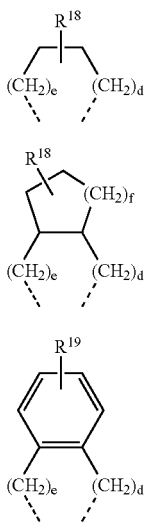

$R^{18}$ is H, alkyl, aryl, OH, O-alkyl, $NH_2$, NH-alkyl or $N(alkyl)_2$, and $R^{19}$ is H, alkyl, aryl, F, Cl, Br, $CF_3$, OH, O-alkyl, $NH_2$, NH-alkyl or $N(alkyl)_2$. The integers d and e are 0, 1, 2 or 3 such that d+e is 3, 4 or 5, and f is 1, 2 or 3. When $R^{15}$ and $R^{16}$ are both H then $X^1$ may not be S or $CH_2$ if b is 1.

Preferred compositions are inhibitors of non-membrane associated post-proline cleaving proteases. The most preferred compositions are selective for non-membrane associated proteases (e.g. for example inhibitors of one or more of QPP, DPP-8 and/or DPP-9).

DETAILED DESCRIPTION OF THE INVENTION

In a first aspect, the present invention relates to a series of novel α-amino acyl derivatives of saturated nitrogen-containing heterocycles according to general formula 1.

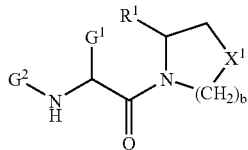

In general formula 1, the group $R^1$ is either a hydrogen atom H or a nitrile group CN. The group $X^1$ is selected from an oxygen atom O, a sulphur atom S, a methylene group $CH_2$, a monofluoromethylene group CHF, a difluoromethylene group $CF_2$, an ethylidene group $CH(CH_3)$, a 2-propylidene group $C(CH_3)_2$ and a cyanomethylene group CH(CN). The integer b is either 1 or 2, such that the nitrogen-containing ring has 5 or 6 members.

The group $G^1$ is either H or a group according to the formula —$CH_2$—$X^2$—$(CH_2)_a$-$G^3$ and the group $G^2$ is either H or a group according to the formula —$CH_2$—$(CH_2)_a$-$G^3$, provided that one of $G^1$ and $G^2$ is H and the other is not H. The group $X^2$ is selected from O, S and $CH_2$. The integer a is 0, 1 or 2, provided that when a is 1 then $X^2$ is $CH_2$.

The group $G^3$ is selected from a group according to general formula 2, a group according to general formula 3 and a group according to general formula 4.

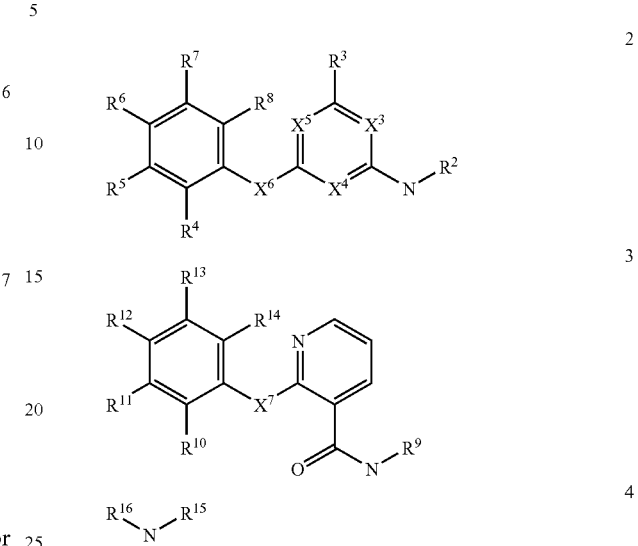

In general formula 2, the groups $X^3$, $X^4$ and $X^5$ are selected from nitrogen N and methine CH, provided that at least two of $X^3$, $X^4$ and $X^5$ are nitrogen. Preferably $X^3$, $X^4$ and $X^5$ are all nitrogen. The group $X^6$ is selected from O and NH. $R^2$ is selected from H and alkyl. $R^3$ is selected from H, Cl, OH, O-alkyl, $NH_2$, NH-alkyl and $N(alkyl)_2$. $R^4$, $R^5$, $R^6$, $R^7$ and $R^8$ are independently selected from H, Br, Cl, F, $CF_3$, alkyl, acyl, OH, O-alkyl, $NH_2$, NH-alkyl, $N(alkyl)_2$, $NO_2$, NH-acyl, $CO_2H$, $CO_2$-alkyl, $CONH_2$, CONH-alkyl, $CON(alkyl)_2$ and CN.

In general formula 3, the group $X^7$ is selected from $CH_2$, O, S and NH. $R^9$ is selected from H and alkyl. $R^{10}$, $R^{11}$, $R^{12}$, $R^{13}$ and $R^{14}$ are independently selected from H, Br, Cl, F, $CF_3$, alkyl, acyl, OH, O-alkyl, $NH_2$, NH-alkyl, $N(alkyl)_2$, $NO_2$, NH-acyl, $CO_2H$, $CO_2$-alkyl, $CONH_2$, CONH-alkyl, $CON(alkyl)_2$ and CN.

In general formula 4, $R^{15}$ and $R^{16}$ are each independently selected from H, alkyl, alkenyl, polyfluoroalkyl, aralkyl, aryl and $CH_2$-L-$R^{17}$, where L is selected from a covalent bond, CH=CH, C≡C and —$C_6H_4$— and $R^{17}$ is selected from H, alkyl and aryl, or $R^{15}$ and $R^{16}$ together are a group selected from general formula 5, general formula 6 and general formula 7.

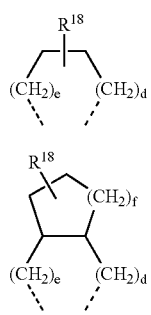

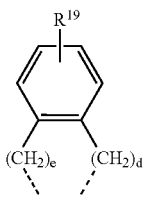

7

In these general formulae, the group $R^{18}$ is selected from H, alkyl, aryl, OH, O-alkyl, $NH_2$, NH-alkyl and $N(alkyl)_2$, and the group $R^{19}$ is selected from H, alkyl, aryl, F, Cl, Br, $CF_3$, OH, O-alkyl, $NH_2$, NH-alkyl and $N(alkyl)_2$. The integers d and e are selected from 0, 1, 2 and 3 such that d+e is 3, 4 or 5, and the integer f is selected from 1, 2 and 3.

When $R^{15}$ and $R^{16}$ are both H then $X^1$ may not be S or $CH_2$ if b is 1.

The term alkyl, as used herein, denotes saturated hydrocarbon groups with between 1 and 10 carbon atoms, including straight-chain, branched and mono- and polycycloalkyl groups, such as methyl, ethyl, propyl, isopropyl, n-butyl, tert-butyl, cyclopentyl, cyclohexylmethyl, 2-cyclohexyl-2-propyl, bicyclo[2.2.2]octyl and the like.

The term alkenyl, as used herein, denotes monounsaturated hydrocarbon groups with between 2 and 10 carbon atoms, including straight-chain, branched and mono- and polycycloalkenyl groups, such as vinyl, allyl, methallyl, cyclohex-3-enyl and the like.

The term aryl, as used herein, denotes monocyclic and fused bicyclic aromatic groups, including carbocyclic groups, such as phenyl and naphthyl, and heteroaryl groups with up to three heteroatoms selected from nitrogen, oxygen and sulphur, such as pyrrolyl, furyl, thienyl, pyrazolyl, imidazolyl, oxazolyl, isothiazolyl, pyridyl, pyrimidinyl, indolyl, quinolinyl and the like. Unless otherwise specified, aryl groups may optionally be substituted with up to three groups independently selected from alkyl, OH, O-alkyl, Cl, F, Br, $NH_2$, NH-alkyl, $N(alkyl)_2$, $CO_2H$, $CO_2$-alkyl, $CONH_2$, CONH-alkyl, $CON(alkyl)_2$, $NO_2$ and CN.

The term aralkyl, as used herein, denotes alkyl groups that are substituted by, or fused to, one or more aryl groups, including benzyl, phenethyl, indanyl, fluorenyl and the like.

The term acyl, as used herein, denotes a group selected from H—CO, alkyl-CO, aryl-CO and aralkyl-CO, including formyl, acetyl, benzoyl, phenylacetyl and the like.

The term polyfluoroalkyl, as used herein, denotes an alkyl group wherein all the hydrogen atoms on one or more of the carbon atoms are replaced by fluorine atoms, including trifluoromethyl, 2,2,2-trifluoroethyl and the like.

In one preferred embodiment of the invention $R^1$ is H.

In another preferred embodiment of the invention $R^1$ is CN.

In another preferred embodiment of the invention $X^1$ is $CH_2$.

In another preferred embodiment of the invention $X^1$ is S.

In another preferred embodiment of the invention b is 1.

In another preferred embodiment of the invention b is 2.

In another preferred embodiment of the invention a is 0.

In another preferred embodiment of the invention a is 0 and $X^2$ is $CH_2$.

In another preferred embodiment of the invention a is 1.

In another preferred embodiment of the invention a is 1 and $X^2$ is $CH_2$.

In another preferred embodiment of the invention a is 2 and $X^2$ is $CH_2$.

In another preferred embodiment of the invention the compound is a compound according to general formula 8.

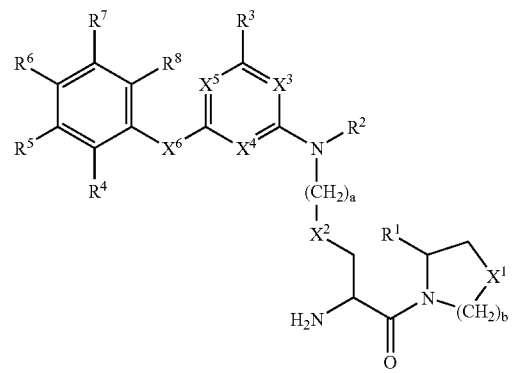

8

In another preferred embodiment of the invention the compound is a compound according to general formula 9.

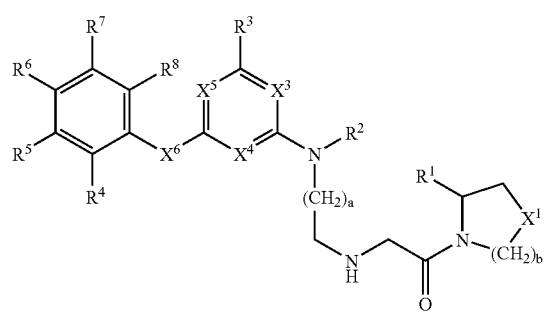

9

In another preferred embodiment of the invention the compound is a compound according to general formula 10.

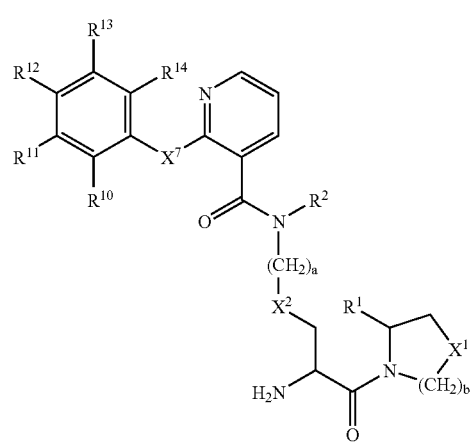

10

In another preferred embodiment of the invention the compound is a compound according to general formula 11.

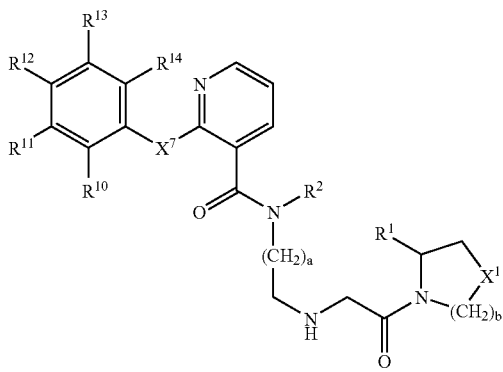

In another preferred embodiment of the invention the compound is a compound according to general formula 12.

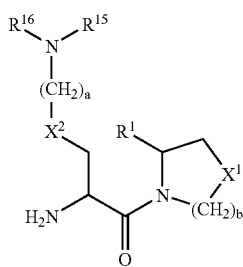

In another preferred embodiment of the, invention the compound is a compound according to general formula 13.

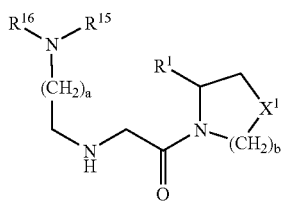

It will be recognised that certain of the compounds within the scope of the present invention are capable of forming salts with suitable acids or bases. To the extent that such salts are pharmaceutically acceptable they are included within the scope of this invention It will further be recognised that certain of the compounds within the scope of the present invention are capable of existing as optical isomers, such as enantiomers and diastereomers. All such optical isomers and mixtures thereof, including but not limited to racemates, are included within the scope of the invention.

The compounds of the present invention are inhibitors of post-proline cleaving proteases such as DPP-IV, QPP, FAP, DPP-8 (DPRP-1) and DPP-9 (DPRP-2). As such they may be useful in the treatment of diseases in which dysregulation of these enzymes or their endogenous substrates plays a role or the disease is ameliorated by inhibition of such enzymes. Accordingly, in further aspects, the present invention provides for the use of compounds according to the present invention in the preparation of pharmaceutical compositions, and for the use of such compositions a therapeutic agents.

Preferred compositions which are inhibitors for QPP may have $G^2$=H, b=1 or 2 and/or a=0 or 1. Further preferred compositions having b=2 include G1 groups having a=0 or 1 and $X^2$ is $CH_2$. Further preferred compositions having b=2 have $X^1$=$CH_2$ or S, for example Example 38 of Table 2. Further preferred compositions having b=1 include G1 groups having a=0 or 1 and $X^2$ is $CH_2$. Further preferred compositions having b=1 have $X^1$=S or $CH_2$ or $CF_2$, for example, Example 42 of Table 2.

The compounds of the present invention can be prepared by methods generally known in the art and illustrated in the following non-limiting examples.

EXAMPLES

Example 1

(2S)-1-[$N^\omega$,$N^\omega$-(Dicinnamyl)-L-lysinyl]pyrrolidine-2-carbonitrile dihydrochloride

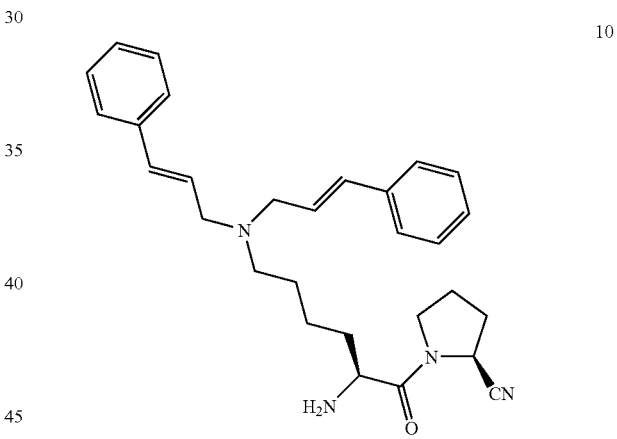

A. ($N^\alpha$-(tert-Butyloxycarbonyl)-$N^\omega$-(9-fluorenylmethyloxycarbonyl)-L-lysinyl)-L-prolinamide $N^\omega$-(tert-Butyloxycarbonyl)-$N^\omega$-(9-fluorenylmethyloxycarbonyl)-L-lysine (5 g, 10.7 mmol) was dissolved in $CH_2Cl_2$ (100 mL). The solution was cooled to 0° C., L-prolinamide (1.78 g, 11.7 mmol) and PyBOP® (6.7 g, 12.8 mmol) were added, and the pH adjusted to pH9 with triethylamine. After 18 h at 0° C. to room temperature the solvent was removed in vacuo and the residue was taken up in ethyl acetate (200 mL). The solution was washed with 0.3M $KHSO_4$ (2×50 mL), sat. $NaHCO_3$ (2×50 mL), water (2×50 mL) and brine (1×50 mL), dried ($Na_2SO_4$) and evaporated in vacuo. The residue was purified by flash chromatography on silica gel (eluant: 2% methanol, 98% chloroform) to give a colourless oil identified as ($N^\omega$-(tert-butyloxycarbonyl)-$N^\omega$-(9-fluorenylmethyloxycarbonyl)-L-lysinyl)-L-prolinamide (4.05 g, 7.2 mmol, 67%).

B. (2S)-1-(N$^\alpha$-(tert-Butyloxycarbonyl)-N$^\omega$-(9-fluorenylmethyloxycarbonyl)-L-lysinyl)pyrrolidine-2-carbonitrile (N$^\alpha$-(tert-Butyloxycarbonyl)-N$^\omega$-(9-fluorenylmethyloxycarbonyl)-L-lysinyl)-L-prolinamide (3.95 g, 7.02 mmol) was dissolved in dry THF (100 mL). The solution was cooled to 0° C., triethylamine (1.4 g, 14 mmol) was added followed by the slow addition of trifluoroacetic anhydride (2.97 g, 14.1 mmol). The pH was adjusted to pH9 with triethylamine. After 30 min the reaction mixture was diluted with ethyl acetate (100 mL), washed with water (1×50 mL) and brine (1×50 mL), dried (Na$_2$SO$_4$) and evaporated in vacuo to give an orange oil. The residue was purified by flash chromatography on silica gel (eluant: 60% pet ether, 40% ethyl acetate) to give a colourless oil identified as (2S)-1-(N$^\alpha$-(tert-butyloxycarbonyl)-N$^\omega$-(9-fluorenylmethyloxycarbonyl)-L-lysinyl)pyrrolidine-2-carbonitrile (3.3 g, 6.11 mmol, 87%).

C. (2S)-1-(N$^\alpha$-(tert-Butyloxycarbonyl)-L-lysinyl)pyrrolidine-2-carbonitrile (2S)-1-(N$^\alpha$-(tert-Butyloxycarbonyl)-N$^\omega$-(9-fluorenylmethyloxycarbonyl)-L-lysinyl)-pyrrolidine-2-carbonitrile (3.1 g, 5.7 mmol) was dissolved in THF (80 mL). Diethylamine (20 mL) was added. After 2 h at room temperature the solvent was removed in vacuo. The residue was purified by flash chromatography on silica gel (eluant: 90% chloroform, 7% methanol, 3% triethylamine) to give a colourless oil identified as (2S)-1-(N$^\alpha$-(tert-butyloxycarbonyl)-L-lysinyl)pyrrolidine-2-carbonitrile (1.63 g, 5.03 mmol, 89%).

D. (2S)-1-(N$^\alpha$-(tert-Butyloxycarbonyl)-N$^\omega$,N$^\omega$-(dicinnamyl)-L-lysinyl)pyrrolidine-2-carbonitrile (2S)-1-(N$^\alpha$-(tert-Butyloxycarbonyl)-L-lysinyl)pyrrolidine-2-carbonitrile (100 mg, 0.31 mmol) was dissolved in methanol (25 mL). To this solution was added trans-cinnamaldehyde (170 mg, 1.18 mmol). After 30 mins sodium triacetoxyborohydride (330 mg, 1.56 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 2% methanol, 98% chloroform) to give a colourless oil identified as (2S)-1-(N$^\alpha$-(tert-butyloxycarbonyl)-N$^\omega$,N$^\omega$-(dicinnamyl)-L-lysinyl)pyrrolidine-2-carbonitrile (38 mg, 0.068 mmol, 11%). Further elution with 9% methanol, 90% chloroform and 1% acetic acid gave a colourless oil identified as (2S)-1-(N$^\alpha$-(tert-butyloxycarbonyl)-N$^\omega$-(cinnamyl)-L-lysinyl)pyrrolidine-2-carbonitrile (32 mg, 0.073 mmol, 12%)

E. (2S)-1-[N$^\omega$,N$^\omega$-(Dicinnamyl)-L-lysinyl]pyrrolidine-2-carbonitrile dihydrochloride (2S)-1-(N$^\alpha$-(tert-Butyloxycarbonyl)-N$^\omega$,N$^\omega$-(dicinnamyl)-L-lysinyl)pyrrolidine-2-carbonitrile (32 mg, 0.057 mmol) was dissolved in 4M HCl/dioxan (20 mL). After 1 h at room temperature the solvent was removed in vacuo. The residue was lyophilised from water to give a white solid identified as (2S)-1-[N$^\omega$,N$^\omega$-(dicinnamyl)-L-lysinyl]pyrrolidine-2-carbonitrile dihydrochloride (37 mg, 0.053 mmol, 93%).

[M+H]$^+$=457.3

$^1$H NMR (CD$_3$OD): δ 1.35-1.55 (2H, m), 1.75-2.00 (2H, m), 2.05-2.23 (6H, m), 3.10-3.29 (4H, m), 3.61-3.68 (2H, m), 4.00-4.03 (4H, m), 4.20-4.30 (1H, m), 4.82-4.93 (1H, m), 6.34-6.39 (2H, m), 6.94 (2H, d, J=5.8 Hz), 7.31-7.37 (6H, m), 7.39-7.53 (4H, m) ppm.

Example 2

(2S)-1-[N$^\omega$-(Cinnamyl)-L-lysinyl]pyrrolidine-2-carbonitrile dihydrochloride

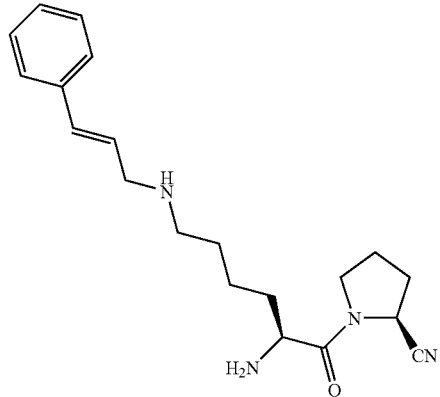

A. (2S)-1-[N$^\omega$-(Cinnamyl)-L-lysinyl]pyrrolidine-2-carbonitrile dihydrochloride (2S)-1-(N$^\alpha$-(tert-Butyloxycarbonyl)-N$^\omega$-(cinnamyl)-L-lysinyl)pyrrolidine-2-carbonitrile (32 mg, 0.057 mmol). was dissolved in 4M HCl/dioxan (20 mL). After 1 h at room temperature the solvent was removed in vacuo. The residue was lyophilised from water to give a white solid identified as (2S)-1-[N$^\omega$-(cinnamyl)-L-lysinyl]pyrrolidine-2-carbonitrile dihydrochloride (37 mg, 0.053 mmol, 93%).

[M+H]$^+$=341.5

$^1$H NMR (CD$_3$OD): δ 1.29-1.55 (2H, m), 1.72-1.80 (2H, m), 1.90-2.11 (2H, m), 2.16-2.29 (6H, m), 3.02-3.09 (2H, m), 3.65-3.69 (2H, m), 3.78-3.82 (2H, m), 4.23-4.27 (1H, m), 4.81-4.82 (1H, m), 4.91-4.99 (1H, m), 6.21-6.32 (1H, m), 6.86 (1H, d, J=6.1 Hz), 7.26-7.35 (3H, m), 7.37-7.40 (2H, m) ppm.

Example 3

(2S)-1-[N$^\omega$,N$^\omega$-(Dicinnamyl)-L-ornithinyl]pyrrolidine-2-carbonitrile dihydrochloride

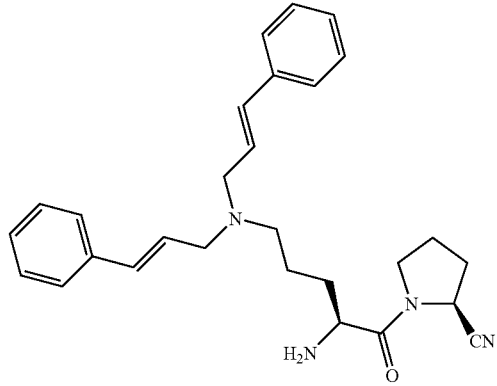

A. (2S)-1-(N$^\alpha$-(tert-Butyloxycarbonyl)-L-ornithyl) pyrrolidine-2-carbonitrile (2S)-1-(N$^\alpha$-(tert-Butyloxycarbonyl)-L-ornithyl)pyrrolidine-2-carbonitrile was prepared by the method described for the lysine derivative in Example 1.

B. (2S)-1-(N$^\alpha$-(tert-Butyloxycarbonyl)-N$^\omega$,N$^\omega$-(dicinnamyl)-L-ornithinyl)pyrrolidine-2-carbonitrile (2S)-1-(N$^\alpha$-(tert-Butyloxycarbonyl)-L-ornithinyl)pyrrolidine-2-carbonitrile (200 mg, 0.65 mmol) was dissolved in methanol (25 mL). To this solution was added trans-cinnamaldehyde (180 mg, 1.25 mmol). After 30 mins sodium triacetoxyborohydride (343 mg, 1.63 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography (eluant: 2% methanol, 98% chloroform) to give a colourless oil identified as (2S)-1-(N$^\alpha$-(tert-butyloxycarbonyl)-N$^\omega$,N$^\omega$-(dicinnamyl)-L-ornithinyl)-pyrrolidine-2-carbonitrile (77 mg, 0.14 mmol, 22%). Further elution with 9% methanol, 90% chloroform and 1% acetic acid gave a colourless oil identified as (2S)-1-(N$^\alpha$-(tert-butyloxycarbonyl)-N$^\omega$-(cinnamyl)-L-ornithinyl)pyrrolidine-2-carbonitrile (78 mg, 0.18 mmol, 28%).

C. (2S)-1-[N$^\omega$,N$^\omega$-(Dicinnamyl)-L-ornithinyl]pyrrolidine-2-carbonitrile dihydrochloride (2S)-1-(N$^\alpha$-(tert-Butyloxycarbonyl)-N$^\omega$,N$^\omega$-(dicinnamyl)-L-ornithinyl)pyrrolidine-2-carbonitrile (67 mg, 0.12 mmol) was dissolved in 4M HCl/dioxan (20 mL). After 1 h at room temperature the solvent was removed in vacuo. The residue was lyophilised from water to give a white solid identified as (2S)-1-[N$^\omega$,N$^\omega$-(dicinnamyl)-L-ornithinyl]pyrrolidine-2-carbonitrile dihydrochloride (82 mg, 0.12 mmol, 100%).

[M+H]$^+$=443.3

$^1$H NMR (CD$_3$OD): δ 1.98-2.12 (4H, m), 2.22-2.29 (4H, m), 3.27-3.31 (4H, m), 3.62-3.67 (2H, m), 3.96 (4H, d, J=7.5 Hz), 4.30-4.40 (1H, m), 4.80-4.83 (1H, m), 6.34-6.41 (2H, m), 6.96 (2H, d, J=15.6 Hz), 7.31-7.39 (6H, m), 7.49-7.53 (4H, m) ppm.

Example 4

(2S)-1-[N$^\omega$-(Cinnamyl)-L-ornithinyl]pyrrolidine-2-carbonitrile dihydrochloride

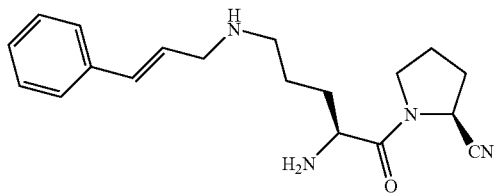

A. (2S)-1-[N$^\omega$-(Cinnamyl)-L-ornithinyl]pyrrolidine-2-carbonitrile dihydrochloride (2S)-1-(N$^\alpha$-(tert-Butyloxycarbonyl)-N$^\omega$-(cinnamyl)-L-ornithinyl)pyrrolidine-2-carbonitrile (71 mg, 0.17 mmol). was dissolved in 4M HCl/dioxan (20 mL). After 1 h at room temperature the solvent was removed in vacuo. The residue was lyophilised from water to give a white solid identified as (2S)-1-[N$^\omega$-(cinnamyl)-L-ornithinyl]pyrrolidine-2-carbonitrile dihydrochloride (91 mg, 0.16 mmol, 100%).

[M+H]$^+$=327.5

$^1$H NMR (CD$_3$OD): δ 1.70-1.88 (2H, m), 1.97-2.01 (2H, m), 2.14-2.32 (4H, m), 3.08-3.13 (2H, m), 3.29-3.31 (3H, m), 3.68-3.71 (2H, m), 3.79-3.82 (2H, m), 4.29-4.31 (1H, m), 4.87-4.91 (1H, m), 6.29-6.31 (1H, m), 6.86 (1H, d, J=15.8 Hz), 7.29-7.30 (3H, m), 7.44-7.48 (2H, m) ppm.

Example 5

3-[N$^\omega$-N$^\omega$-(Dicinnamyl)-L-lysinyl]thiazolidine dihydrochloride

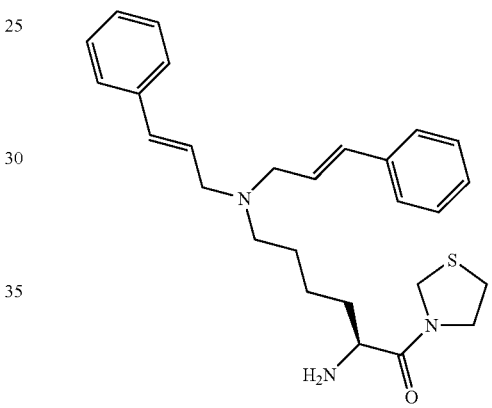

A. 3-[N$^\alpha$-(tert-Butyloxycarbonyl)-N$^\omega$-(9-fluorenylmethyloxycarbonyl)-L-lysinyl]-thiazolidine N$^\alpha$-(tert-Butyloxycarbonyl)-N$^\omega$-(9-fluorenylmethyloxycarbonyl)-L-lysine (2.73 g, 6 mmol) was dissolved in CH$_2$Cl$_2$/DMF (9:1, 100 mL). To this solution at 0° C. were added 1-hydroxybenzotriazole hydrate (1.53 g, 10 mmol), water-soluble carbodiimide (1.34 g, 7 mmol), thiazolidine (1.28 g, 18 mmol) and N-methylmorpholine (1.0 g, 10 mmol). After 18 h at 0° C. to room temperature the solvent was removed in vacuo and the residue was taken up in ethyl acetate (100 mL). The solution was washed with 0.3M KHSO$_4$ (2×25 mL), sat. NaHCO$_3$ (2×25 mL), water (2×25 mL) and brine (1×25 mL), dried (Na$_2$SO$_4$) and evaporated in vacuo. The residue was purified by flash chromatography on silica gel (eluant: 75% ethyl acetate, 25% pet. ether) to give a white solid identified as 3-[N$^\alpha$-(tert-butyloxycarbonyl)-N$^\omega$-(9-fluorenylmethyloxycarbonyl)-L-lysinyl]thiazolidine (2.55 g, 4.85 mmol, 81%).

B. 3-[N$^\alpha$-(tert-Butyloxycarbonyl)-L-lysinyl]thiazolidine

3-[N$^\alpha$-(tert-Butyloxycarbonyl)-N$^\omega$-(9-fluorenylmethyloxycarbonyl)-L-lysinyl]thiazolidine (1.15 g, 2.13 mmol) was dissolved in acetonitrile (20 mL). Diethylamine (5 mL)

C. 3-(N$^\alpha$-(tert-Butyloxycarbonyl)-N$^\omega$,N$^\omega$-(dicinnamyl)-L-lysinyl)thiazolidine 3-(N$^\alpha$-(tert-Butyloxycarbonyl)-L-lysinyl)thiazolidine (200 mg, 0.6 mmol) was dissolved in methanol (25 mL). To this solution was added trans-cinnamaldehyde (400 mg, 3.0 mmol). After 30 mins sodium triacetoxyborohydride (534 mg, 2.54 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 2% methanol, 98% chloroform) to give a colourless oil identified as 3-(N$^\alpha$-(tert-butyloxycarbonyl)-N$^\omega$,N$^\omega$-(di-cinnamyl)-L-lysinyl)thiazolidine (139 mg, 0.25 mmol, 40%).

D. 3-[N$^\omega$,N$^\omega$-(Dicinnamyl)-L-lysinyl]thiazolidine dihydrochloride 3(N$^\alpha$-(tert-Butyloxycarbonyl)-N$^\omega$,N$^\omega$-(di-cinnamyl)-L-lysinyl)thiazolidine (139 mg, 0.25 mmol). was dissolved in 4M HCl/dioxan (20 mL). After 1 h at room temperature the solvent was removed in vacuo. The residue was lyophilised from water to give a pale brown solid identified as 3-[N$^\omega$, N$^\omega$-(dicinnamyl)-L-lysinyl]thiazolidine dihydrochloride (127 mg, 0.24 mmol, 96%).

[M+H]$^+$=450.2

$^1$H NMR (CD$_3$OD): δ 1.49-1.55 (2H,m), 1.89-1.98 (4H, m), 3.01-3.30 (4H, m), 3.4-3.5 (4H, m), 3.7-3.9 (3H, m), 4.0-4.2 (3H, m), 4.2-4.8 (2H, br m), 6.38-6.44 (2H, m), 6.99-6.93 (2H, m), 7.34-7.37 (5H, m), 7.51-7.60 (4H, m) ppm.

Example 6

3-[N$^\omega$,N$^\omega$-(Cinnamyl)-L-lysinyl]thiazolidine dihydrochloride

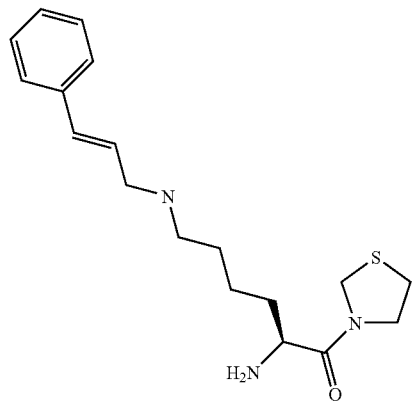

A. 3-(N$^\alpha$-(tert-Butyloxycarbonyl)-N$^\omega$,N$^\omega$-(cinnamyl)-L-lysinyl)thiazolidine 3-(N$^\alpha$-(tert-Butyloxycarbonyl)-L-lysinyl)thiazolidine (200 mg, 0.6 mmol) was dissolved in methanol (25 mL). To this solution was added trans-cinnamaldehyde (400 mg, 3.0 mmol). After 30 mins sodium triacetoxyborohydride (534 mg, 2.54 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 1% triethylamine, 5% methanol, 94% chloroform) to give a colourless oil identified as 3-(N$^\alpha$-(tert-butyloxycarbonyl)-N$^\omega$,N$^\omega$-(cinnamyl)-L-lysinyl)thiazolidine (215 mg, 0.50 mmol, 83%).

B. 3-[N$^\omega$,N$^\omega$-(Cinnamyl)-L-lysinyl]thiazolidine dihydrochloride 3-(N$^\alpha$-(tert-Butyloxycarbonyl)-N$^\omega$,N$^\omega$-(cinnamyl)-L-lysinyl)thiazolidine (215 mg, 0.5 mmol). was dissolved in 4M HCl/dioxan (20 mL). After 1 h at room temperature the solvent was removed in vacuo. The residue was lyophilised from water to give a pale brown solid identified as 3-[N$^\omega$, N$^\omega$-(cinnamyl)-L-lysinyl]thiazolidine dihydrochloride (160 mg, 0.40 mmol, 79%).

[M+H]$^+$=334.4

$^1$H NMR (CD$_3$OD): δ 1.28-1.30 (1H, m), 1.51-1.53 (1H, m), 1.79-1.78 (1H, m), 1.93-1.98 (2H, m), 2.9-3.3 (5H, m), 3.6-3.8 (5H, m), 4.30-4.70 (5H, m), 6.2-6.3 (1H, m), 6.85-6.91(1H, m), 7.1-7.7 (5H, m) ppm.

Example 7

1-[N$^\omega$-(Cyclohexylmethyl)-L-ornithinyl]pyrolidine dihydrochloride

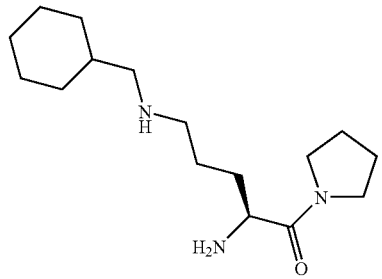

A. 1-[N$^\omega$-(Benzyloxycarbonyl)-N$^\alpha$-(tert-butyloxycarbonyl)-L-ornithinyl]pyrrolidine N$^\omega$-(Benzyloxycarbonyl)-N$^\alpha$-(tert-butyloxycarbonyl)-L-ornithine (5.49 g, 15 mmol) was dissolved in CH$_2$Cl$_2$/DMF (9:1, 100 mL). To this solution at 0° C. was added 1-hydroxybenzotriazole hydrate (3.37 g, 22 mmol), water-soluble carbodiimide (3.46 g, 18 mmol), pyrrolidine (1.28 g, 18 mmol) and N-methylmorpholine (2.0 g, 20 mmol). After 18 h at 0° C. to room temperature the solvent was removed in vacuo and the residue was taken up in ethyl acetate (200 mL). The solution was washed with 0.3M KHSO$_4$ (2×50 mL), sat. NaHCO$_3$ (2×50 mL), water (2×50 mL) and brine (1×50 mL), dried (Na$_2$SO$_4$) and evaporated in vacuo. The residue was purified by flash chromatography on silica gel (eluant: 90% ethyl acetate, 10% pet. ether) to give a colourless oil identified as 1-[N$^\omega$-(benzyloxycarbonyl)-N$^\alpha$-(tert-butyloxycarbonyl)-L-ornithyl]pyrrolidine (5.15 g, 12.3 mmol, 82%).

B. 1-[N$^\alpha$-(tert-Butyloxycarbonyl)-L-ornithinyl]pyrrolidine

1-[N$^\omega$-(Benzyloxycarbonyl)-N$^\alpha$-(tert-butyloxycarbonyl)-L-ornithinyl]pyrrolidine (2.15 g, 5.13 mmol) was dissolved in methanol (80 mL). This solution was hydrogenated over 10% Pd/C (400 mg). After 2 h the catalyst was filtered off and washed with methanol (50 mL). The combined filtrates were evaporated in vacuo to give an off white solid identified as 1-[N$^\alpha$-(tert-butyloxycarbonyl)-L-ornithinyl]pyrrolidine (1.35 g, 4.74 mmol, 94%).

C. 1-(N$^\alpha$-(tert-Butyloxycarbonyl)-N$^\omega$-cyclohexylmethyl)-L-ornithinyl)pyrrolidine 1-[N$^\alpha$-(tert-Butyloxycarbonyl)-L-ornithinyl]pyrrolidine (100 mg, 0.35 mmol) was dissolved in methanol (25 mL). To this solution was added cyclohexanecarboxaldehyde (44 mg, 0.39 mmol). After 30 mins sodium triacetoxyborohydride (148 mg, 0.70 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 1% triethylamine, 5% methanol, 94% chloroform) to give a colourless oil identified as 1-(N$^\alpha$-(tert-Butyloxycarbonyl)-N$^\omega$-(cyclohexylmethyl)-L-ornithinyl)pyrrolidine (51 mg, 0.18 mmol, 52%).

D. 1-[N$^\omega$-(Cyclohexylmethyl)-L-ornithinyl]pyrrolidine dihydrochloride 1-(N$^\alpha$-(tert-Butyloxycarbonyl)-N$^\omega$-(cyclohexylmethyl)-L-ornithinyl)pyrrolidine (215 mg, 0.5 mmol) was dissolved in 4M HCl/dioxan (20 mL). After 1 h at room temperature the solvent was removed in vacuo. The residue was lyophilised from water to give a white solid identified as 1-[N$^\omega$-(cyclohexylmethyl)-L-ornithinyl]pyrrolidine dihydrochloride (160 mg, 0.40 mmol, 79%).

[M+H]$^+$=282.3

$^1$H NMR (CD$_3$OD): δ 0.93-1.24 (3H, m), 1.66-1.81 (15H, m), 2.50-2.70 (2H, m), 2.71-2.88 (2H, m), 3.2-3.48 (6H, m), 4.08 (1H, m), 8.35-8.38 (1H, m), 8.80-8.85 (1H, m) ppm.

Example 8

3-[N$^\omega$-Me-N$^\omega$-(2-napthylmethyl)-L-lysinyl]thiazolidine dihydrochloride

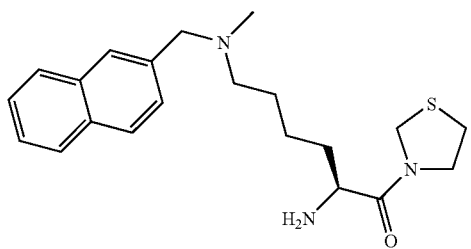

A. N$^\alpha$-(tert-Butyloxycarbonyl-N$^\omega$-benzyl-L-lysine methyl ester N$^\alpha$-(tert-Butyloxycarbonyl-L-lysine methyl ester (6.1 g, 22.2 mmol) was dissolved in methanol (100 mL). To this solution was added benzaldehyde (1.9 g, 17.5 mmol). After 2 hours sodium triacetoxyborohydride (5.8 g, 27.3 mmol) was added. After 18 h at room temperature the solvent was removed in vacuo and the residue was taken up in chloroform (200 mL). This solution was washed with sat Na HCO$_3$ (1×50 mL), water (12×50 mL) and brine (1×50 mL), dried (Na$_2$SO$_4$) and evaporated in vacuo to give a yellow oil. The residue was purified by flash chromatography on silica gel (eluant: 1% acetic acid, 5% methanol, 94% chloroform) to give a colourless oil identified as N$^\alpha$-(tert-butyloxycarbonyl-N$^\omega$-benzyl-L-lysine methyl ester (5.2 g, 14.2 mmol, 82%).

B. N$^\alpha$-tert-Butyloxycarbonyl-N$^\omega$-benzyl-N$^\omega$-methyl-L-lysine methyl ester N$^\alpha$-tert-Butyloxycarbonyl-N$^\omega$-benzyl-L-lysine methyl ester (5.0 g, 14.2 mmol) was dissolved in methanol (100 mL). To this solution was added formaldehyde (37% solution in water, 10 mL). After 2 hours sodium triacetoxyborohydride (3.9 g, 18.4 mmol) was added. After 18 h at room temperature the solvent was removed in vacuo and the residue was taken up in chloroform (200 mL). This solution was washed with sat. Na HCO$_3$ (1×50 mL), water (12×50 mL) and brine (1×50 mL), dried (Na$_2$SO$_4$) and evaporated in vacuo to give a colourless oil identified as N$^\alpha$-tert-butyloxycarbonyl-N$^\omega$-benzyl-N$^\omega$-methyl-L-lysine methyl ester (5.2 g, 14.2 mmol, 100%).

C. N$^\alpha$-tert-Butyloxycarbonyl-N$^\omega$-methyl-L-lysine methyl ester

N$^\alpha$-tert-Butyloxycarbonyl-N$^\omega$-benzyl-N$^\omega$-methyl-L-lysine methyl ester (5.0 g, 14.2 mmol) was dissolved in methanol/water (9:1, 100 mL). To this solution was added ammonium formate (1.6, 19.3 mmol) and 10% palladium on charcoal (2 g). After 3 hours at 60° C. the catalyst was filtered off through celite and the residue washed with methanol (50 mL). The combined filtrates were evaporated in vacuo and the residue was taken up in chloroform (200 mL). This solution was washed with sat Na HCO$_3$ (1×50 mL), water (12×50 mL) and brine (1×50 mL), dried (Na$_2$SO$_4$) and evaporated in vacuo to give a colourless oil identified as N$^\alpha$-(tert-butyloxycarbonyl-N$^\omega$-methyl-L-lysine methyl ester (3.48 g, 12.5 mmol, 93%).

D. N$^\alpha$-tert-Butyloxycarbonyl-N$^\omega$-(1,1-dimethyl-2,2,2-trichloroethoxycarbonyl)-N$^\omega$-methyl-L-lysine methyl ester N$^\alpha$-tert-Butyloxycarbonyl-N$^\omega$-methyl-L-lysine methyl ester (3.1 g, 11.1 mmol) was dissolved in dichloromethane (100 mL). To this solution was added 1,1-dimethyl-2,2,2-trichloroethyl chloroformate (3.0 g, 12.5 mmol) and triethylamine (2.3 g, 23 mmol). After 18 hours at room temperature the solvent was removed in vacuo and the residue was taken up in ethyl acetate (200 mL). This solution was washed with 0.3M KHSO$_4$ (1×50 mL), sat NaHCO$_3$ (1×50 mL), water (1×50 mL) and brine (1×50 mL), dried (Na$_2$SO$_4$) and evaporated in vacuo to give a yellow oil purified by flash chromatography on silica gel (eluant: 30% ethyl acetate, 70% pet. ether) to give colourless oil identified as N$^\alpha$-(tertbutyloxycarbonyl-N$^\omega$-(1,1-dimethyl-2,2,2-trichloroethoxycarbonyl)-N$^\omega$-methyl-L-lysine methyl ester (3.28 g, 6.98 mmol, 63%).

E. N$^{6\alpha}$-tert-Butyloxycarbonyl-N$^\omega$-(1,1-dimethyl-2, 2,2-trichloroethoxycarbonyl)-N$^\omega$-methyl-L-lysine N$^\alpha$-(tert-Butyloxycarbonyl-N$^\omega$-(1,1-dimethyl-2,2,2-trichloroethoxycarbonyl)-N$^\omega$-methyl-L-lysine methyl ester (3.1 g, 6.6 mmol) was dissolved in tetrahydrofuran (100 mL). 1M Lithium hydroxide (7 mL, 7.0 mmol) was added. After 3 hours at room temperature the reaction mixture was diluted with ethyl acetate (150 mL), washed with 1M HCl (1×50 mL), water (1×50 mL) and brine (1×50 mL), dried (Na$_2$SO$_4$) and evaporated in vacuo to give colourless oil identified as N$^\alpha$-(tert-butyloxycarbonyl-N$^\omega$-(1,1-dimethyl-2,2,2-trichloroethoxycarbonyl)-N$^\omega$-methyl-L-lysine (2.94 g, 6.45 mmol, 98%).

F. 3-(N$^\alpha$-tert-Butyloxycarbonyl-N$^\omega$-1,1-dimethyl-2, 2,2-trichloroethoxycarbonyl)-N$^\omega$-methyl-L-lysinyl) thiazoldine N$^{6\alpha}$-(tert-Butyloxycarbonyl-N$^\omega$-(1,1-dimethyl-2,2,2-trichloroethoxycarbonyl)-N$^\omega$-methyl-L-lysine (700 mg, 1.51 mmol) was dissolved in CH$_2$Cl$_2$/DMF (9:1, 20 mL). To this solution at 0° C. were added 1-hydroxybenzotriazole hydrate (410 mg, 3.0 mmol), water-soluble carbodiimide (250 mg, 1.3 mmol), thiazolidine (170 mg, 1.9 mmol) and N-methylmorpholine (1.0 g, 10 mmol). After 18 h at 0° C. to room temperature the solvent was removed in vacuo and the residue was taken up in ethyl acetate (70 mL). The solution was washed with 0.3M KHSO$_4$ (1×25 mL), sat. NaHCO$_3$ (1×25 mL), water (1×25 mL) and brine (1×25 mL), dried (Na$_2$SO$_4$) and evaporated in vacuo. The residue was purified by flash chromatography on silica gel (eluant: 50% ethyl acetate, 50% pet. ether) to give a white solid identified as 3-(N$^\alpha$-tert-butyloxycarbonyl-N$^\omega$-(1,1-dimethyl-2,2,2-trichloroethoxycarbonyl)-N$^\omega$-methyl-L-lysinyl)thiazolidine (758 mg, 1.42 mmol, 94%).

G. 3-(N$^\alpha$-tert-Butyloxycarbonyl-N$^\omega$-methyl-L-lysinyl)thiazolidine 3-(N$^\alpha$-tert-Butyloxycarbonyl-N$^\omega$-(1,1-dimethyl-2,2,2-trichloroethoxycarbonyl)-N$^\omega$-methyl-L-lysinyl)thiazolidine (730 mg, 1.36 mmol) was dissolved in acetic acid (30 mL). Zinc powder (200 mg) was added. After stirring at room temperature for 18 hours the solvent was removed in vacuo and the residue was taken up in chloroform (70 mL). The solution was washed with sat. NaHCO$_3$ (1×25 mL), water (1×25 mL) and brine (1×25 mL), dried (Na$_2$SO$_4$) and evaporated in vacuo to give a colourless oil identified as 3-(N$^\alpha$-tert-butyloxycarbonyl-N$^\omega$-methyl-L-lysinyl)thiazolidine (438 mg, 1.32 mmol, 97%).

H. 3-[N$^\alpha$-tert-Butyloxycarbonyl-N$^\omega$-methyl-N$^\omega$-(2-napthylmethyl)-L-lysinyl]thiazolidine 3-(N$^\alpha$-tert-Butyloxycarbonyl-N$^\omega$-methyl-L-lysinyl)thiazolidine (50 mg, 0.15 mmol) was dissolved in 1,2-dichloroethane (20 mL). To this solution was added 2-naphthaldehyde (26 mg, 0.17 mmol). After 2 hours sodium triacetoxyborohydride (36 mg, 0.17 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 4% methanol, 96% chloroform) to give a colourless oil identified as 3-[N$^\alpha$-tert-butyloxycarbonyl-N$^\omega$-methyl-N$^\omega$-(2-napthylmethyl)-L-lysinyl]thiazolidine (51 mg, 0.11 mmol, 72%).

I. 3-[N$^\omega$-Methyl-N$^\omega$-(2-napthylmethyl)-L-lysinyl]thiazolidine dihydrochloride 3-[N$^\alpha$-tert-Butyloxycarbonyl-N$^\omega$-methyl-N$^\omega$-(2-napthylmethyl)-L-lysinyl]thiazolidine (44 mg, 0.093 mmol) was dissolved in 4M HCl/dioxan (20 mL). After 1 h at room temperature the solvent was removed in vacuo. The residue was lyophilised from water to give a pale brown solid identified as 3-[N$^\omega$-methyl-N$^\omega$-(2-napthylmethyl)-L-lysinyl]thiazolidine dihydrochloride (37 mg, 0.083 mmol, 89%).

[M+H]$^+$=372.2

$^1$H NMR (CD$_3$OD): δ 1.50-1.53 (2H, m), 1.91-1.98 (4H, m), 2.82 (3H,s), 3.08-3.19 (4H, m), 3.36-3.75 (5H, m), 4.32-4.47 (2H, m), 4.60-4.71 (2H, m), 7.55-7.59 (2H, m), 7.65-7.68 (1H, m), 7.90-8.00 (3H, m), 8.10-8.12 (1H, m) ppm.

Example 9

3-[N$^\omega$-Methyl-N$^\omega$-(1-Napthylmethyl)-L-ornithyl]thiazolidine dihydrochloride

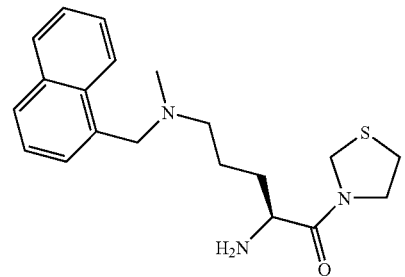

A. 3-[N-(tert-Butyloxycarbonyl)-O$^\omega$-methyl-L-glutamyl]thiazolidine

N-(tert-Butyloxycarbonyl)-O$^\omega$-methyl-L-glutamic acid (6.28 g, 24 mmol) was dissolved in CH$_2$Cl$_2$/DMF (9:1, 100 ml). To this solution at 0° C. were added 1-hydroxybenzotriazole hydrate (5.5 g, 36 mmol), water-soluble carbodiimide (5.38 g, 28 mmol), thiazolidine (2.48 g, 28 mmol) and N-methylmorpholine (3.0 g, 30 mmol). The mixture was stirred for 18 h at 0° C. to room temperature then the solvent was removed in vacuo and the residue was taken up in ethyl acetate (150 ml). The solution was washed with 0.3M KHSO$_4$ (2×30 ml), sat. NaHCO$_3$ (2×30 ml), water (2×30 ml) and brine (1×30 ml), dried (Na$_2$SO$_4$) and evaporated in vacuo. The residue was purified by flash chromatography on silica gel (eluant: 70% ethyl acetate, 30% pet. ether 60-80) to give a brown oil identified as 3-[N-(tert-butyloxycarbonyl)-O$^\omega$-methyl-L-glutamyl]thiazolidine (4.0 g, 12 mmol, 50%).

B. 3-[N,N-Di-(tert-butyloxycarbonyl)-O$^\omega$-methyl-L-glutamyl]thiazolidine 3-[N-(tert-Butyloxycarbonyl)-O$^\omega$-methyl-L-glutamyl]thiazolidine (3.2 g, 9.6 mmol) was dissolved in acetonitrile (20 mL). Di-tert-butyl dicarbonate (3.14 g, 14.4 mmol) and 4-dimethylaminopyridine (235 mg, 1.93 mmol) were added. After 18 hours at room temperature further di-tert-butyl dicarbonate (3.14 g, 14.4 mmol) was added. After a further 3 days at room temperature the solvent was evaporated in vacuo the residue was purified by flash chromatography on silica gel (eluant: 70% ethyl acetate, 30% pet. ether 60-80) to give a colourless oil identified as 3-[N,N-di-(tert-butyloxycarbonyl)-O$^\omega$-methyl-L-glutamyl]thiazolidine (2.0 g, 4.63 mmol, 48%).

C. 3-[N,N-Di-(tert-butyloxycarbonyl)-L-glutamyl]thiazolidine

3-[N,N-di-(tert-butyloxycarbonyl)-O$^\omega$-methyl-L-glutamyl]thiazolidine (950 mg, 2.22 mmol) was dissolved in THF (50 ml). 1M Lithium hydroxide (5.5 ml, 5.5 mmol) was added. The mixture was stirred for 1 hour at room temperature then the solvent was removed in vacuo and the residue was taken up in ethyl acetate (70 ml). The solution was washed with 0.3M KHSO$_4$ (2×20 ml), water (2×20 ml) and brine (1×20 ml), dried (Na$_2$SO$_4$) and evaporated in vacuo to give a colourless oil identified as 3-[N,N-di-(tert-butyloxycarbonyl)-L-glutamyl]thiazolidine (912 mg, 2.2 mmol, 98%).

D. 3-[2-(N,N-Di-(tert-butyloxycarbonyl)amino)-5-hydroxypentanoyl]thiazolidine 3-[N,N-Di-(tert-butyloxycarbonyl)-L-glutamyl]thiazolidine (912 mg, 2.2 mmol) was dissolved in tetrahydrofuran (30 mL). This solution was cooled to −20° C., N-methylmorpholine (300 mg, 2.96 mmol) and isobutyl chloroformate (387 mg, 2.83 mmol) were added. After 20 mins at −20° C. the reaction mixture was added to a solution of sodium borohydride (182 mg, 4.8 mmol) in water (5 mL) at 0° C. After 1 hour the reaction mixture was diluted with ethyl acetate (150 mL). This solution was washed with water (1×20 mL) and brine (1×20 mL), dried (Na$_2$SO$_4$) and evaporated in vacuo to give a colourless oil identified as 3-[2-(N,N-di-(tert-butyloxycarbonyl)amino-5-hydroxy-pentanoyl]thiazolidine (800 mg, 2.0 mmol, 92%).

E. 3-[2-(N,N-Di-(tert-butyloxycarbonyl)amino-5-oxopentanoyl]thiazolidine

3-[2-N,N-((Di-tert-butyloxycarbonyl)amino)-5-hydroxypentanoyl]thiazolidine (800 mg, 2.0 mmol) was dissolved in dichloromethane (50 mL). Dess-Martin periodinane (933 mg, 2.2 mmol) was added. After 1 hour at room temperature the reaction mixture was diluted with ethyl acetate (150 mL). This solution was washed with water (1×20 ml) and brine (1×20 ml), dried (Na$_2$SO$_4$) and evaporated in vacuo to give a colourless oil. Purified by flash chromatography on silica gel (eluant: 50% ethyl acetate, 50% pet. ether 60-80) to give a colourless oil identified as 3-[2-(N,N-di-(tert-butyloxycarbonyl)amino-5-oxopentanoyl]thiazolidine (210 mg, 0.52 mmol, 26%).

F. 3-[N,N-Di-(tert-butyloxycarbonyl-N$^\omega$-methyl-N$^\omega$-(1-napthylmethyl)-L-ornithyl]-thiazolidine 3-[N,N-Di-(tert-butyloxycarbonyl)amino-5-oxopentanoyl]thiazolidine was dissolved in 1,2-dichloroethane (20 mL). To this solution was added N-methyl-1-napthylmethylamine. After 2 hours sodium triacetoxyborohydride was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel to give a colourless oil identified as 3-[N,N-di-(tert-butyloxycarbonyl-N$^\omega$-methyl-N$^\omega$-(1-napthylmethyl)-L-ornithyl]thiazolidine.

G. 3-[N$^\omega$-Methyl-N$^\omega$-(1-Napthylmethyl)-L-ornithyl]thiazolidine dihydrochloride 3-[N,N-Di-(tert-butyloxycarbonyl-N$^\omega$-methyl-N$^\omega$-napthylmethyl)-L-ornithyl]thiazolidine was dissolved in 4M HCl/dioxan (20 mL). After 1 h at room temperature the solvent was removed in vacuo. The residue was lyophilised from water to give a pale brown solid identified as 3-[N$^\omega$-Me, N$^\omega$-(1-napthylmethyl)-L-ornithyl]thiazolidine dihydrochloride.

Example 10

3,3-Difluoro-1-[N$^\omega$-(2-methylbutyl)-L-lysinyl]pyrrolidine dihydrochloride

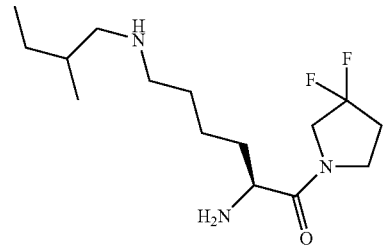

A. 1-(tert-Butyloxycarbonyl)-3-pyrrolidone (3R)-1-(tert-Butyloxycarbonyl)-3-hydroxypyrrolidine (980 mg, 5.3 mmol) was dissolved in CH$_2$Cl$_2$ (40 ml). Dess-Martin periodinane (2.5 g, 5.8 mmol) was added. The mixture was stirred for 3 hours at room temperature then the solvent was removed in vacuo and the residue was taken up in ethyl acetate (300 ml). The solution was washed with sat. NaHCO$_3$, water and brine, dried (Na$_2$SO$_4$) and evaporated in vacuo to give a colourless oil. The residue was purified by flash chromatography on silica gel (eluant: 20% ethyl acetate, 80% pet. ether 60-80) to give a colourless oil identified as 1-(tert-butyloxycarbonyl)-3-pyrrolidone (842 mg, 4.6 mmol, 87%).

B. 1-(tert-Butyloxycarbonyl)-3,3-difluoropyrrolidine 1-(tert-Butyloxycarbonyl)-3-pyrrolidone (810 mg, 4.4 mmol) was dissolved in CH$_2$Cl$_2$ (30 ml). (Diethylamino)sulphur trifluoride (2.2 g, 13.7 mmol) was added to this solution at 0° C. The mixture was stirred for 18 hours at 0° C. to room temperature then carefully poured into sat. NaHCO$_3$ (100 ml). The mixture was stirred for 15 min then extracted with CH$_2$Cl$_2$. The organic extract was washed with water and brine, dried (Na$_2$SO$_4$) and evaporated in vacuo to give an orange oil. The residue was purified by flash chromatography (eluant: 10% ethyl acetate, 90% pet. ether 60-80) to give a colourless oil identified as 1-(tert-butyloxycarbonyl)-3,3-difluoropyrrolidine (580 mg, 2.8 mmol, 64%).

C. 3,3-Difluoropyrrolidine hydrochloride 1-(tert-Butyloxycarbonyl)-3,3-difluoropyrrolidine (540 mg, 2.6 mmol) was dissolved in 4M HCl/dioxan (30 ml). The solution was stirred for 1 hour at room temperature then the solvent was removed in vacuo to give an off white solid identified as 3,3-difluoropyrrolidine hydrochloride (370 mg, 2.6 mmol, 100%).

D. 1-[N$^\alpha$-(tert-Butyloxycarbonyl)-N$^\omega$-(9-fluorenylmethyloxycarbonyl)-L-lysinyl]-3,3-difluoropyrrolidine N$^\alpha$-(tert-Butyloxycarbonyl)-N$^\omega$-(9-fluorenylmethyloxycarbonyl)-L-lysine (1.14 g, 2.4 mmol) was dissolved in CH$_2$Cl$_2$/DMF (9:1, 100 ml). To this solution at 0° C. were added 1-hydroxybenzotriazole hydrate (394 mg, 2.9 mmol), water-soluble carbodiimide (680 mg, 3.4 mmol), 3,3-difluoropyrrolidine hydrochloride (380 mg, 2.43 mmol) and N-methylmorpholine (400 mg, 4 mmol). The mixture was stirred for 18 h at 0° C. to room temperature then the solvent was removed in vacuo and the residue was taken up in ethyl acetate (200 ml). The solution was washed with 0.3M KHSO$_4$, sat. NaHCO$_3$, water and brine, dried (Na$_2$SO$_4$) and evaporated in vacuo. The residue was purified by flash chromatography on silica gel (eluant: 65% ethyl acetate, 35% pet. ether 60-80) to give a white solid identified as 1-[N$^\alpha$-(tert-butyloxycarbonyl)-N$^\omega$-(9-fluorenylmethyloxycarbonyl)-L-lysinyl]-3,3-difluoropyrrolidine (1.0 g, 1.8 mmol, 75%).

E. 1-[N$^\alpha$-tert-Butyloxycarbonyl)-L-lysinyl]-3,3-difluoropyrrolidine

1-[N$^\alpha$-(tert-Butyloxycarbonyl)-N$^\omega$-(9-fluorenylmethyloxycarbonyl)-L-lysinyl]-3,3-difluoro-pyrrolidine (1.01 g, 1.8 mmol) was dissolved in THF (20 ml). Diethylamine (5 ml) was added. The mixture was stirred for 3 hours at room temperature then the solvent was removed in vacuo and the residue was purified by flash chromatography on silica gel (eluant: 90% chloroform, 7% methanol, 3% triethylamine) to give a pale yellow oil identified as 1-[N$^\alpha$-(tert-butyloxycarbonyl)-L-lysinyl]-3,3-difluoropyrrolidine (598 mg, 1.78 mmol, 99%).

F. 1-[N$^\alpha$-(tert-Butyloxycarbonyl)-N$^\omega$-(2-methylbutyl)-L-lysinyl]-3-difluoro-pyrrolidine 1-[N$^\alpha$-(tert-Butyloxycarbonyl)-L-lysinyl]-3,3-difluoropyrrolidine was dissolved in 1,2-dichloroethane (20 mL). To this solution was added 2-methylbutanal. After 2 hours sodium triacetoxyborohydride was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel to give a colourless oil identified as 1-[N$^\alpha$-(tert-butyloxycarbonyl)-N$^\omega$-(2-methylbutyl)-L-lysinyl]-3,3-difluoropyrrolidine.

G. 3,3-Difluoro-1-[N$^\omega$-(2-methylbutyl)-L-lysinyl]pyrrolidine dihydrochloride 1-[N$^\alpha$-(tert-Butyloxycarbonyl)-N$^\omega$-(2-methylbutyl)-L-lysinyl]-3,3-difluoropyrrolidine was dissolved in 4M HCl/dioxan (20 ml). The mixture was stirred for 1 hour at room temperature then the solvent was removed in vacuo to give a colourless oil identified as 3,3-difluoro-1-[N$^\omega$-(2-methylbutyl)-L-lysinyl]pyrrolidine dihydrochloride.

Example 11

1-[N$^\omega$-(3-Cyclohexenylmethyl)-L-lysinyl]thiomorpholine dihydrochloride

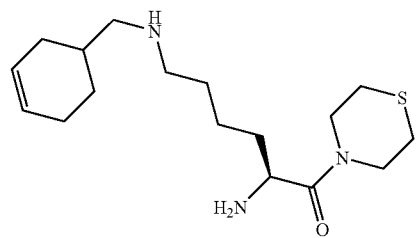

A. 3-[N$^\alpha$-(tert-Butyloxycarbonyl)-N$^\omega$-(9-fluorenylmethyloxycarbonyl)-L-lysinyl]thiomorpholine N$^\alpha$-(tert-Butyloxycarbonyl)-N$^\omega$-(9-fluorenylmethyloxycarbonyl)-L-lysine (2.5 g, 5.34 mmol) was dissolved in CH$_2$Cl$_2$/DMF (9:1, 100 mL). To this solution at 0° C. were added 1-hydroxybenzotriazole hydrate (1.44 g, 10.6 mmol), water-soluble carbodiimide (1.35 g, 6.5 mmol), thiomorpholine (710 mg, 6.9 mmol) and N-methylmorpholine (800 mg, 8 mmol). After 18 h at 0° C. to room temperature the solvent was removed in vacuo and the residue was taken up in ethyl acetate (100 mL). The solution was washed with 0.3M KHSO$_4$ (2×25 mL), sat. NaHCO$_3$ (2×25 mL), water (2×25 mL) and brine (1×25 mL), dried (Na$_2$SO$_4$) and evaporated in vacuo. The residue was purified by flash chromatography on silica gel (eluant: 75% ethyl acetate, 25% pet. ether) to give a white solid identified as 3-[N$^\alpha$-(tert-butyloxycarbonyl)-N$^\omega$-(9-fluorenylmethyloxycarbonyl)-L-lysinyl]thiomorpholine (2.70 g, 4.88 mmol, 91%).

B. 3-[N$^\alpha$-(tert-Butyloxycarbonyl)-L-lysinyl]thiomorpholine

3-[N$^\alpha$-(tert-Butyloxycarbonyl)-N$^\omega$-(9-fluorenylmethyloxycarbonyl)-L-lysinyl]thiomorpholine (2.6 g, 4.7 mmol) was dissolved in tetrahydrofuran (20 mL). Diethylamine (5 mL) was added. After 90 min at room temperature the solvent was removed in vacuo and the residue was purified by flash chromatography on silica gel (eluant: 90% chloroform, 7% methanol, 3% triethylamine) to give a pale yellow oil identified as 3-[N$^\alpha$-(tert-butyloxycarbonyl)-L-lysinyl]thiomorpholine (1.2 g, 3.637 mmol, 77%).

C. 3-[N$^\alpha$-(tert-Butyloxycarbonyl)-N$^\omega$-(3-cyclohexenylmethyl)-L-lysinyl]-thiomorpholine 3-(N$^\alpha$-(tert-Butyloxycarbonyl)-L-lysinyl)thiomorpholine (150 mg, 0.45 mmol) was dissolved in methanol (25 mL). To this solution was added 3-cyclohexenecarboxaldehyde (400 mg, 0.45 mmol). After 30 mins sodium triacetoxyborohydride (150 mg, 0.71 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 1% acetic acid, 9% methanol, 90% chloroform) to give a colourless oil identified as 3-(N$^\alpha$-(tert-butyloxycarbonyl)-N$^\omega$-(3-cyclohexenylmethyl)-L-lysinyl)thiomorpholine (66 mg, 0.12 mmol, 26%).

D. 1-[N$^\omega$-(3-Cyclohexenylmethyl)-L-lysinyl]thiomorpholine dihydrochloride 3-(N$^\alpha$-(tert-Butyloxycarbonyl)-N$^\omega$-(3-cyclohexenylmethyl)-L-lysinyl)thiomorpholine (66 mg, 0.12 mmol) was dissolved in 4M HCl/dioxan (20 mL). After 1 h at room temperature the solvent was removed in vacuo. The residue was lyophilised from water to give a white solid identified as 1-[N$^\omega$-(3-cyclohexenylmethyl)-L-lysinyl]thiomorpholine dihydrochloride (62 mg, 0.12 mmol, 100%).

[M+H]$^+$=326.2

Example 12

(2S)-1-[N$^\omega$-(2-(3'-trifluoromethylanilino)pyridyl-3-carbonyl)-L-ornithyl]thiazoldine dihydrochloride

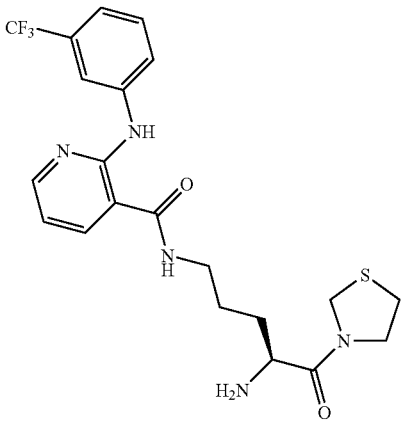

A. 3-[N$^{60}$-tert-Butyloxycarbonyl-N$^\omega$-(1,1-dimethyl-2,2,2-trichloroethoxycarbonyl)-L-ornithyl]thiazolidine N$^\alpha$-(tert-Butyloxycarbonyl-N$^{107}$-(1,1-dimethyl-2,2,2-trichloroethoxycarbonyl)-L-ornithine (2.5 g, 5.9 mmol) was dissolved in CH$_2$Cl$_2$/DMF (9:1, 30 mL). To this solution at 0° C. were added 1-hydroxybenzotriazole hydrate (1.6 g, 11.9 mmol), water-soluble carbodiimide (1.4 g, 7.6 mmol), thiazolidine (650 mg, 7.3 mmol) and N-methylmorpholine (2.0 g, 20 mmol). After 18 h at 0° C. to room temperature the solvent was removed in vacuo and the residue was taken up in ethyl acetate (70 mL). The solution was washed with 0.3M KHSO$_4$ (1×25 mL), sat. NaHCO$_3$ (1×25 mL), water (1×25 mL) and brine (1×25 mL), dried (Na$_2$SO$_4$) and evaporated in vacuo. The residue was purified by flash chromatography on silica gel (eluant: 70% ethyl acetate, 30% pet. ether) to give a colourless oil identified as 3-[N$^\alpha$-tert-butyloxycarbonyl-N$^\omega$-(1,1-dimethyl-2,2,2-trichloroethoxycarbonyl)-L-ornithyl]thiazolidine (758 mg, 1.42 mmol, 94%).

B. 3-(N$^\alpha$-tert-Butyloxycarbonyl-L-ornithinyl)thiazolidine

3-[N$^\alpha$-tert-Butyloxycarbonyl-N$^\omega$-(1,1-dimethyl-2,2,2-trichloroethoxycarbonyl)-L-ornithyl]thiazolidine (130 mg, 0.26 mmol) was dissolved in acetic acid (30 mL). Zinc powder (100 mg) was added. After stirring at room temperature for 18 hours the solvent was removed in vacuo and the residue was taken up in chloroform (70 mL). The solution was washed with sat. NaHCO$_3$ (1×25 mL), water (1×25 mL) and brine (1×25 mL), dried (Na$_2$SO$_4$) and evaporated in vacuo to give a colourless oil identified as 3-(N$^\alpha$-tert-butyloxycarbonyl-L-ornithinyl)thiazolidine (80 mg, 0.26 mmol, 100%).

C. 3-[N$^\alpha$-tert-Butyloxycarbonyl-N$^\omega$-(2-(3'-trifluoromethylanilino)pyridyl-3-carbonyl)-L-ornithinyl]thiazolidine 3-(N$^\alpha$-tert-Butyloxycarbonyl-L-ornithinyl)thiazolidine (80 mg, 0.26 mmol) was dissolved in CH$_2$Cl$_2$/DMF (9:1, 20 mL). To this solution at 0° C. was added 1-hydroxybenzotriazole hydrate (80 mg, 0.6 mmol), water-soluble carbodiimide (65 mg, 0.32 mmol), niflumic acid (82 mg, 0.29 mmol) and N-methylmorpholine (100 mg, 1.0 mmol). After 18 h at 0° C. to room temperature the solvent was removed in vacuo and the residue was taken up in ethyl acetate (70 mL). The solution was washed with 0.3M KHSO$_4$ (1×20 mL), sat. NaHCO$_3$ (1×20 mL), water (1×20 mL) and brine (1×20 mL), dried (Na$_2$SO$_4$) and evaporated in vacuo. The residue was purified by flash chromatography on silica gel (eluant: 75% ethyl acetate, 25% pet. ether) to give a yellow oil identified as 3-[N$^\alpha$-tert-butyloxycarbonyl-N$^\omega$-(2-(3'-trifluoromethylanilino)pyridyl-3-carbonyl)-L-ornithinyl]-thiazolidine (60 mg, 0.12 mmol, 45%).

D. (2S)-1-[N$^\omega$-(2-(3'-Trifluoromethylanilino)pyridyl-3-carbonyl)-L-ornithyl]-thiazolidine dihydrochloride 3-[N$^\alpha$-tert-Butyloxycarbonyl-N$^\omega$-(2-(3'-trifluoromethylanilino)pyridyl-3-carbonyl)-L-ornithinyl]thiazolidine (54 mg, 0.10 mmol) was dissolved in 4M HCl/dioxan (20 mL). After 1 h at room temperature the solvent was removed in vacuo. The residue was lyophilised from water to give a pale brown solid identified as (2S)-1-[N$^\omega$-(2-(3'-trifluoromethylanilino)pyridyl-3-carbonyl)-L-ornithyl]thiazolidine dihydrochloride (47 mg, 0.10 mmol, 100%).

[M+H]$^+$=468.0

$^1$H NMR (CD$_3$OD): δ1.77-1.82 (2H, m), 1.84-2.00 (2H, m), 3.03-3.15 (4H, m), 3.41-3.51 (2H, m), 3.65-3.71 (2H, m), 3.80-3.87 (1H, m), 4.46-4.49 (2H, m), 4.65-4.72 (2H, m), 7.06-7.11 (1H, m), 7.61-7.11 (3H, m), 7.95 (1H, s), 8.09 (1H, d, J=4.7 Hz), 8.49 (1H, d, J=4.2 Hz) ppm.

Example 13

3,3-Difluoro-1-[N$^\omega$-(2-(3'-chloroanilino)pyridyl-3-carbonyl)-L-ornithyl]pyrrolidine dihydrochloride

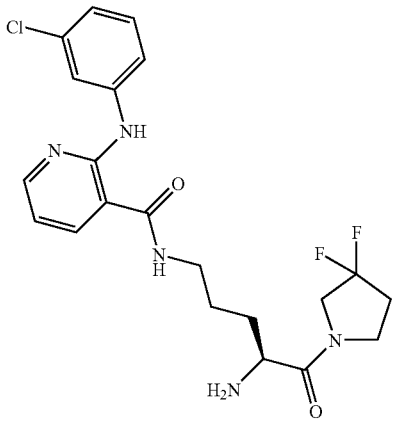

A. 1-[N$^\alpha$-(tert-Butyloxycarbonyl)-L-ornithyl]-3,3-difluoropyrrolidine 1-[N$^\alpha$-(tert-Butyloxycarbonyl)-L-ornithyl]-3,3-difluoropyrrolidine was prepared as described for the lysine derivative in Example 9.

B. 3-Chloroanilinonicotinic acid

3-Chloroaniline was dissolved in xylene. 2-Aminonicotinic acid was added. The reaction mixture was heated at 150° C. for 18 hours after which time the reaction mixture was diluted with ethyl acetate giving an off-white solid identified as 3-chloroanilinonicotinic acid.

C. 3,3-Difluoro-[N$^\alpha$-tert-butyloxycarbonyl-N$^\omega$-(2-(3'-chloroanilino)pyridyl-3-carbonyl)-L-ornithinyl]pyrrolidine 1-[N$^\alpha$-(tert-Butyloxycarbonyl)-L-ornithyl]-3,3-difluoropyrrolidine was dissolved in CH$_2$Cl$_2$/DMF (9:1, 20 mL). To this solution at 0° C. was added 1-hydroxybenzotriazole hydrate, water-soluble carbodiimide, 3-chloroanilinonicotinic acid and N-methylmorpholine.

After 18 h at 0° C. to room temperature the solvent was removed in vacuo and the residue was taken up in ethyl acetate (70 mL). The solution was washed with 0.3M KHSO$_4$ (1×20 mL), sat. NaHCO$_3$ (1×20 mL), water (1×20 mL) and brine (1×20 mL), dried (Na$_2$SO$_4$) and evaporated in vacuo. The residue was purified by flash chromatography on silica gel (eluant: 75% ethyl acetate, 25% pet. ether) to give a yellow oil identified as 3,3-difluoro-[N$^\alpha$-tert-butyloxycarbonyl-N$^\omega$-(2-(3'-chloroanilino)pyridyl-3-carbonyl)]-L-ornithinyl)pyrrolidine.

D. 3,3-Difluoro-1-[N$^\omega$-(2-(3'-chloroanilino)pyridyl-3-carbonyl)-L-ornithyl]pyrrolidine dihydrochloride 3,3-Difluoro-[N$^\alpha$-tert-butyloxycarbonyl-N$^\omega$-(2-(3'-chloroanilino)pyridyl-3-carbonyl)]-L-ornithinyl)pyrrolide was dissolved in 4M HCl/dioxan (20 mL). After 1 h at room temperature the solvent was removed in vacuo. The residue was lyophilised from water to give a pale brown solid identified as 3,3-difluoro-1-[N$^\omega$-(2-(3'-chloroanilino)pyridyl-3-carbonyl)-L-ornithyl]pyrrolidine dihydrochloride.

Example 14

3-[N$^\omega$-6-Chloro-4-(2',5'-dichloroanilino)-1,3,5-triazinyl)-L-lysinyl]thiazolidine dihydrochloride

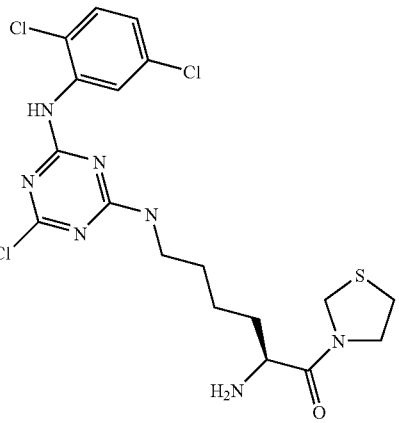

A. 4,6-Dichloro-2-(2',5'-dichloroanilino)-1,3,5-triazine

Cyanuric chloride (1.844 g, 10 mmol) was dissolved in acetonitrile (20 mL). The solution was cooled to −20° C. A solution of 2,5-dichloroaniline (1.62 g, 10 mmol) and triethylamine (1.0 g, 10 mmol) was slowly added. After 1 hour at −20° C. the solvent was removed in vacuo and the residue was taken up in ethyl acetate (150 mL). The solution was washed with water (1×50 mL) and brine (1×50 mL), dried (Na$_2$SO$_4$) and evaporated in vacuo. The residue was recrystallised from ethyl acetate/hexane to give an off white solid identified as 4,6-dichloro-2-(2',5'-dichloroanilino)-1,3,5-triazine (1.86 mg, 6.0 mmol, 60%).

B. 3-[N$^\alpha$-tert-Butyloxycarbonyl-N$^\omega$-chloro-4-(2',5'-dichloroanilino)-1,3,5-triazinyl)-L-lysinyl]thiazolidine 3-(N$^\alpha$-(tert-Butyloxycarbonyl)-L-lysinyl)thiazolidine (800 mg, 2.58 mmol) was dissolved in dichloromethane (30 mL). To this solution was added 4,6-dichloro-2-(2',5'-dichloroanilino)-1,3,5-triazine (810 mg, 2.6 mmol) and triethylamine (300 mg, 3.0 mmol). After 2 hours at room temperature the solvent was removed in vacuo and the residue was taken up in ethyl acetate (150 mL). This solution was washed with water (2×30 mL) and brine (1×30 mL), dried (Na$_2$SO$_4$) and evaporated in vacuo to give a yellow oil. The residue was purified by flash chromatography (eluant: 60% ethyl acetate, 40% pet. ether) to give a white solid identified as 3-[N$^\alpha$-tert-butyloxycarbonyl-N$^\omega$-chloro-4-(2',5'-dichloroanilino)-1,3,5-triazinyl)-L-lysinyl]thiazolidine (1.33 g, 2.23 mmol, 86%).

C. 3-[N$^\omega$-6-Chloro-4-(2',5'-dichloroanilino)-1,3,5-triazinyl)-L-lysinyl]thiazolidine dihydrochloride 3-[N$^\alpha$-tert-Butyloxycarbonyl-N$^\omega$-6-chloro-4-(2',5'-dichloroanilino)-1,3,5-triazinyl)-L-lysinyl]thiazolidine (59 mg, 0.10 mmol) was dissolved in 4M HCl/dioxan (20 mL). After 1 h at room temperature the solvent was removed in vacuo. The residue was lyophilised from water to give a white solid identified as 3-[N$^\omega$-6-chloro-4-(2',5'-dichloroanilino)-1,3,5-triazinyl)-L-lysinyl]thiazolidine dihydrochloride (55 mg, 0.098 mmol, 98%).

[M+H]$^+$=492.2, 494.4

$^1$H NMR (CD$_3$OD): δ1.46-1.51 (2H, m), 1.65-1.67 (2H, m), 1.80-1.96 (2H, m), 3.05-3.14 (2H, m), 3.38-3.42 (2H, m), 3.55-3.75 (4H, m), 4.31-4.36 (2H, m0, 4.40-4.52 (1H, m), 4.63-4.95 (2H, m), 7.15-7.18 (1H, m), 7.40-7.45 (1H, m), 8.15-8.25 (1H, m) ppm.

Example 15

3-[N$^\omega$-4-(2',5'-Dichloroanilino)-6-hydroxy-1,3,5-triazinyl)-L-lysinyl]thiazolidine bis(trifluoroacetate)

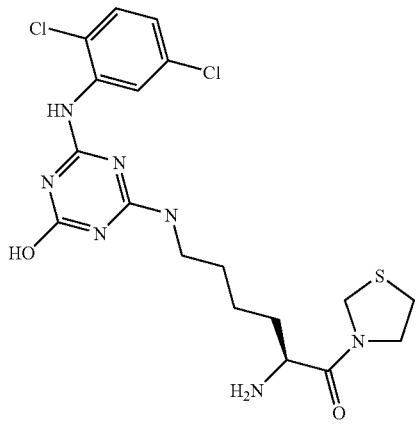

A. 3-[N$^\omega$-4-(2',5'-Dichloroanilino)-6-hydroxy-1,3,5-triazinyl)-L-lysinyl]thiazolidine bis(trifluoroacetate)

3-[N$^\alpha$-tert-Butyloxycarbonyl-N$^\omega$-6-chloro-4-(2',5'-dichloroanilino)-1,3,5-triazinyl)]-L-ornithinyl)thiazolidine (54 mg, 0.09 mmol) was dissolved in trifluoroacetic acid (20 mL) and water (2 mL). After 2 hours at 70° C. the solvent was removed in vacuo. The residue was lyophilised from water to give a white solid identified as 3-[N$^\omega$-4-(2',5'-dichloroanilino)-6-hydroxy-1,3,5-triazinyl-L-lysinyl]thiazolidine bis(trifluoroacetate) (63 mg, 0.089 mmol, 97%).

[M+H]$^+$=472.1, 474.2

$^1$H NMR (CD$_3$OD): δ1.42-1.47 (2H, m), 1.62-1.67 (2H, m), 1.82-1.89 (2H, m), 3.04-3.16 (4H, m), 3.70-3.75 (2H, m), 3.84-3.91 (1H, m), 4.25-4.32 (2H, m), 4.45-4.54 (2H, m), 4.64-4.70 (2H, m), 7.05-7.15 (1H, m), 7.34-7.38 (1H, m), 7.49-7.55 (1H, m), 7.80-7.92 (1H, m) ppm.

Example 16

3-[N$^\omega$-4-(2',5'-Dichloroanilino)-6-methylamino-1,3,5-triazinyl)-L-lysinyl]thiazolidine dihydrochloride

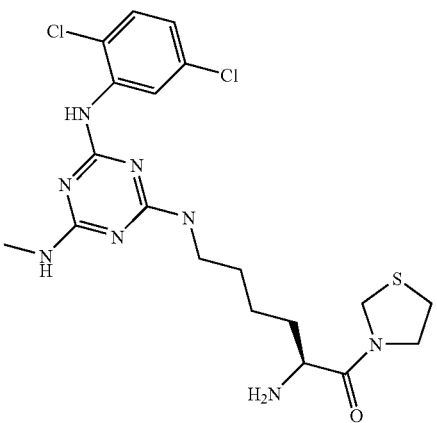

A. 3-[N$^\alpha$-tert-Butyloxycarbonyl-N$^\omega$-4-(2',5'-dichloroanilino)-6-dimethylamino-1,3,5-triazinyl)-L-lysinyl]thiazolidine 3-[N$^\alpha$-tert-Butyloxycarbonyl-N$^\omega$-3-chloro-5-(2',5'-dichloroanilino)-2,4,6-triazinyl)]-L-ornithinyl)thiazolidine (120 mg, 0.20 mmol) was dissolved in 1M dimethylamine in tetrahydrofuran (25 mL). After 18 hours at room temperature the solvent was removed in vacuo and the residue was purified by flash chromatography on silica gel (eluant: 70% ethyl acetate, 30% pet. ether) to give a white solid identified as 3-[N$^\alpha$-tert-butyloxycarbonyl-N$^\omega$-4-(2',5'-dichloroanilino)-6-dimethylamino-1,3,5-triazinyl)-L-lysinyl]thiazolidine (110 mg, 0.18 mmol, 90%).

B. 3-[N$^\omega$-4-(2',5'-Dichloroanilino)-6-dimethylamino-1,3,5-triazinyl)-L-lysinyl]-thiazolidine dihydrochloride 3-[N$^\alpha$-tert-Butyloxycarbonyl-N$^\omega$-4-(2',5'-dichloroanilino)-6-dimethylamino-1,3,5-triazinyl)-L-lysinyl]thiazolidine (110 mg, 0.18 mmol) was dissolved in 4M HCl/dioxan (20 mL). After 1 h at room temperature the solvent was removed in vacuo. The residue was lyophilised from water to give a white solid identified as 3-[N$^\omega$-4-(2',5'-dichloroanilino)-6-dimethylamino-1,3,5-triazinyl)-L-lysinyl]thiazolidine dihydrochloride (105 mg, 0.18 mmol, 100%).

[M+H]$^+$=499.1, 501.1

$^1$H NMR (CD$_3$OD): δ1.52-1.55 (2H, m), 1.69-1.71 (2H, m), 1.90-1.98 (2H, m), 3.13-3.22 (8H, m), 3.42-3.62 (2H, m), 3.65-3.69 (4H, m), 4.37-4.39 (2H, m), 4.46-4.49 (1H, m), 4.57-4.77 (2H, m), 7.20-7.22 (1H, m), 7.45-7.50 (1H, m), 8.09-8.12 (1H, m) ppm.

The following compounds were prepared by analogous methods.
TABLE 1
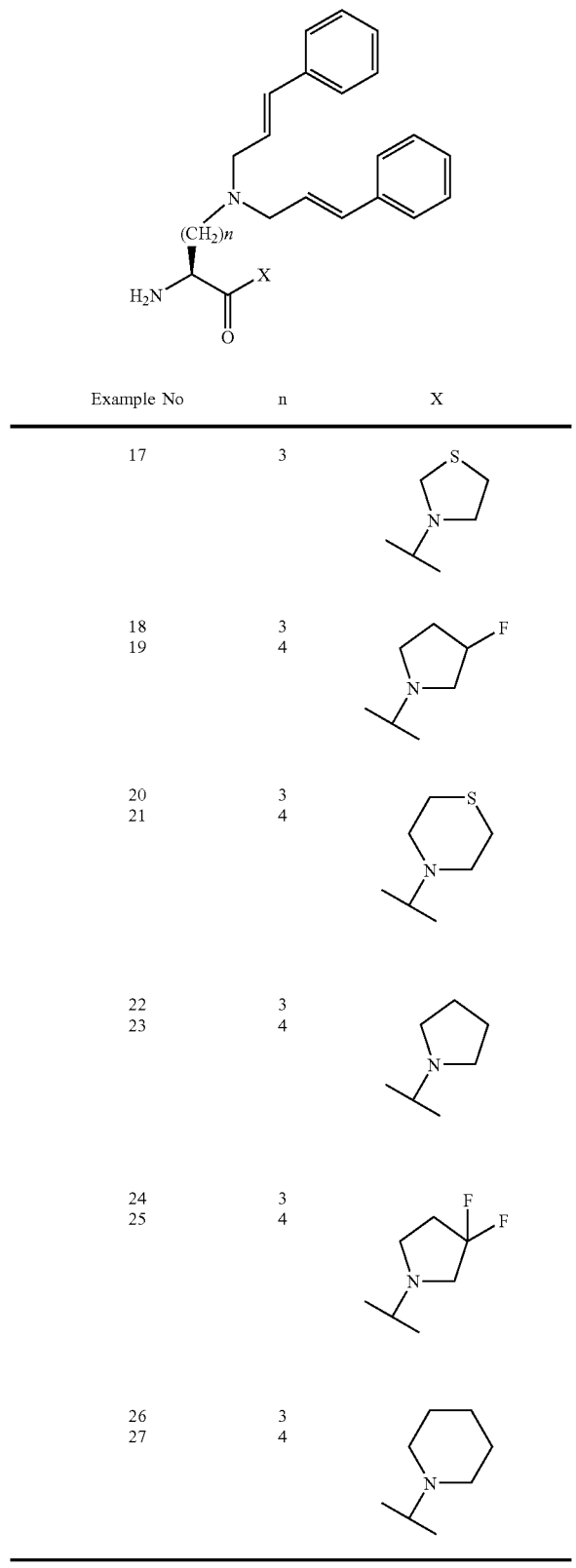
| Example No | n | X |
|---|---|---|
| 17 | 3 | thiazolidine |
| 18 | 3 | 3-fluoropyrrolidine |
| 19 | 4 | |
| 20 | 3 | thiomorpholine |
| 21 | 4 | |
| 22 | 3 | pyrrolidine |
| 23 | 4 | |
| 24 | 3 | 3,3-difluoropyrrolidine |
| 25 | 4 | |
| 26 | 3 | piperidine |
| 27 | 4 | |
TABLE 2
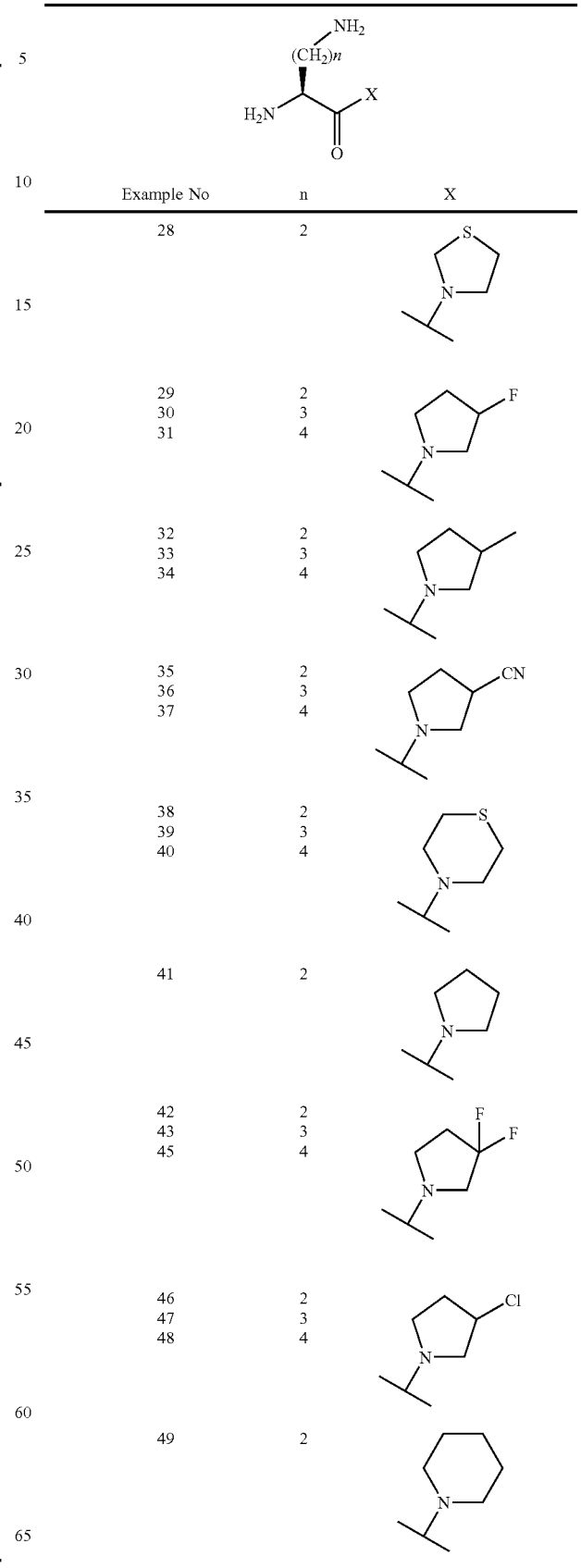
| Example No | n | X |
|---|---|---|
| 28 | 2 | thiazolidine |
| 29 | 2 | 3-fluoropyrrolidine |
| 30 | 3 | |
| 31 | 4 | |
| 32 | 2 | 3-methylpyrrolidine |
| 33 | 3 | |
| 34 | 4 | |
| 35 | 2 | 3-cyanopyrrolidine |
| 36 | 3 | |
| 37 | 4 | |
| 38 | 2 | thiomorpholine |
| 39 | 3 | |
| 40 | 4 | |
| 41 | 2 | pyrrolidine |
| 42 | 2 | 3,3-difluoropyrrolidine |
| 43 | 3 | |
| 45 | 4 | |
| 46 | 2 | 3-chloropyrrolidine |
| 47 | 3 | |
| 48 | 4 | |
| 49 | 2 | piperidine |

TABLE 2-continued

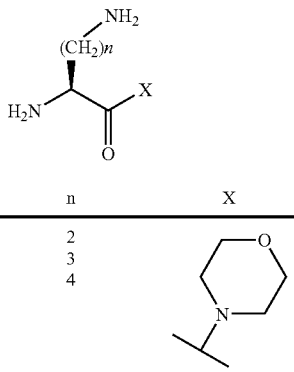

| Example No | n | X |
|---|---|---|
| 50 | 2 | |
| 51 | 3 | (4-isopropylmorpholine shown at right) |
| 52 | 4 | |

TABLE 3

Structure:

R³\N/R⁴
  |
 (CH₂)ᵦ
  |
H₂N–CH–C(O)–N(ring with (CH₂)ₐ and X)

| Ex No | a | b | X | R³ | R⁴ |
|---|---|---|---|---|---|
| 53 | 1 | 3 | S | H | CH₃CH₂CH₂ |
| 54 | 1 | 4 | | H | |
| 55 | 1 | 3 | CH₂ | H | |
| 56 | 1 | 4 | | H | |
| 57 | 1 | 3 | CF₂ | H | |
| 58 | 1 | 4 | | H | |
| 59 | 1 | 4 | S | CH₃ | |
| 60 | 1 | 4 | | CH(CH₃)₂ | |
| 61 | 1 | 4 | CH₂ | CH₃ | |
| 62 | 1 | 4 | | CH(CH₃)₂ | |
| 63 | 1 | 3 | S | CH(CH₃)₂ | |
| 64 | 1 | 3 | CH₂ | CH(CH₃)₂ | |
| 65 | 2 | 3 | S | H | |
| 66 | 2 | 4 | | H | |
| 67 | 2 | 3 | CH₂ | H | |
| 68 | 2 | 4 | | H | |
| 69 | 1 | 3 | S | H | CH₃CH₂CH₂CH₂ |
| 70 | 1 | 4 | | H | |
| 71 | 1 | 3 | CH₂ | H | |
| 72 | 1 | 4 | | H | |
| 73 | 1 | 3 | CF₂ | H | |
| 74 | 1 | 4 | | H | |
| 75 | 1 | 4 | S | CH₃ | |
| 76 | 1 | 4 | | CH(CH₃)₂ | |
| 77 | 1 | 4 | CH₂ | CH₃ | |
| 78 | 1 | 4 | | CH(CH₃)₂ | |
| 79 | 1 | 3 | S | CH(CH₃)₂ | |
| 80 | 1 | 3 | CH₂ | CH(CH₃)₂ | |
| 81 | 2 | 3 | S | H | |
| 82 | 2 | 4 | | H | |
| 83 | 2 | 3 | CH₂ | H | |
| 84 | 2 | 4 | | H | |
| 85 | 1 | 3 | S | H | (CH₃)₂CHCH₂ (isobutyl) |

TABLE 3-continued

| Ex No | a | b | X | R³ | R⁴ |
|---|---|---|---|---|---|
| 86 | 1 | 4 | | H | |
| 87 | 1 | 3 | CH₂ | H | |
| 88 | 1 | 4 | | H | |
| 89 | 1 | 3 | CF₂ | H | |
| 90 | 1 | 4 | | H | |
| 91 | 1 | 4 | S | CH₃ | |
| 92 | 1 | 4 | | CH(CH₃)₂ | |
| 93 | 1 | 4 | CH₂ | CH₃ | |
| 94 | 1 | 4 | | CH(CH₃)₂ | |
| 95 | 1 | 3 | S | CH(CH₃)₂ | |
| 96 | 1 | 3 | CH₂ | CH(CH₃)₂ | |
| 97 | 2 | 3 | S | H | |
| 98 | 2 | 4 | | H | |
| 99 | 2 | 3 | CH₂ | H | |
| 100 | 2 | 4 | | H | |
| 101 | 1 | 3 | S | H | (CH₃)CH(CH₃)CH₂ (sec-butyl/isopentyl) |
| 102 | 1 | 4 | | H | |
| 103 | 1 | 3 | CH₂ | H | |
| 104 | 1 | 4 | | H | |
| 105 | 1 | 3 | CF₂ | H | |
| 106 | 1 | 4 | S | CH₃ | |
| 107 | 1 | 4 | | CH(CH₃)₂ | |
| 108 | 1 | 4 | CH₂ | CH₃ | |
| 109 | 1 | 4 | | CH(CH₃)₂ | |
| 110 | 1 | 3 | S | CH(CH₃)₂ | |
| 111 | 1 | 3 | CH₂ | CH(CH₃)₂ | |
| 112 | 2 | 3 | S | H | |
| 113 | 2 | 4 | | H | |
| 114 | 2 | 3 | CH₂ | H | |
| 115 | 2 | 4 | | H | |
| 116 | 1 | 3 | S | H | (CH₃)₃CCH₂ (neopentyl) |
| 117 | 1 | 4 | | H | |
| 118 | 1 | 3 | CH₂ | H | |
| 119 | 1 | 4 | | H | |
| 120 | 1 | 3 | CF₂ | H | |
| 121 | 1 | 4 | | H | |
| 122 | 1 | 4 | S | CH₃ | |
| 123 | 1 | 4 | | CH(CH₃)₂ | |
| 124 | 1 | 4 | CH₂ | CH₃ | |
| 125 | 1 | 4 | | CH(CH₃)₂ | |
| 126 | 1 | 3 | S | CH(CH₃)₂ | |
| 127 | 1 | 3 | CH₂ | CH(CH₃)₂ | |
| 128 | 2 | 3 | S | H | |
| 129 | 2 | 4 | | H | |
| 130 | 2 | 3 | CH₂ | H | |
| 131 | 2 | 4 | | H | |
| 132 | 1 | 3 | S | H | (CH₃)₂CH (isopropyl) |
| 133 | 1 | 4 | | H | |
| 134 | 1 | 3 | CH₂ | H | |
| 135 | 1 | 4 | | H | |

TABLE 3-continued

| Ex No | a | b | X | R³ | R⁴ |
|---|---|---|---|---|---|
| 136 | 1 | 3 | CF₂ | H | |
| 137 | 1 | 4 | | H | |
| 138 | 1 | 4 | S | CH₃ | |
| 139 | 1 | 4 | | CH(CH₃)₂ | |
| 140 | 1 | 4 | CH₂ | CH₃ | |
| 141 | 1 | 4 | | CH(CH₃)₂ | |
| 142 | 1 | 3 | S | CH(CH₃)₂ | |
| 143 | 1 | 3 | CH₂ | CH(CH₃)₂ | |
| 144 | 2 | 3 | S | H | |
| 145 | 2 | 4 | | H | |
| 146 | 2 | 3 | CH₂ | H | |
| 147 | 2 | 4 | | H | |
| 148 | 1 | 3 | S | | |

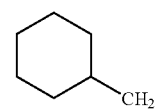

| 149 | 1 | 4 | | | |
| 150 | 1 | 4 | CH₂ | | |
| 151 | 1 | 3 | CF₂ | | |
| 152 | 1 | 4 | | | |
| 153 | 1 | 4 | S | CH₃ | |
| 154 | 1 | 4 | | CH(CH₃)₂ | |
| 155 | 1 | 4 | CH₂ | CH₃ | |
| 156 | 1 | 4 | | CH(CH₃)₂ | |
| 157 | 1 | 3 | S | CH(CH₃)₂ | |
| 158 | 1 | 3 | CH₂ | CH(CH₃)₂ | |
| 159 | 2 | 3 | S | H | |
| 160 | 2 | 4 | | H | |
| 161 | 2 | 3 | CH₂ | H | |
| 162 | 2 | 4 | | H | |
| 163 | 1 | 3 | S | | |

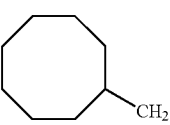

| 164 | 1 | 4 | | H | |
| 165 | 1 | 3 | CH₂ | H | |
| 166 | 1 | 4 | | H | |
| 167 | 1 | 3 | CF₂ | H | |
| 168 | 1 | 4 | | H | |
| 169 | 1 | 4 | S | CH₃ | |
| 170 | 1 | 4 | | CH(CH₃)₂ | |
| 171 | 1 | 4 | CH₂ | CH₃ | |
| 172 | 1 | 4 | | CH(CH₃)₂ | |
| 173 | 1 | 3 | S | CH(CH₃)₂ | |
| 174 | 1 | 3 | CH₂ | CH(CH₃)₂ | |
| 175 | 2 | 3 | S | H | |
| 176 | 2 | 4 | | H | |
| 177 | 2 | 3 | CH₂ | H | |
| 178 | 2 | 4 | | H | |
| 179 | 1 | 3 | S | H | 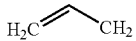 |
| 180 | 1 | 4 | | H | |
| 181 | 1 | 3 | CH₂ | H | |
| 182 | 1 | 4 | | H | |
| 183 | 1 | 3 | CF₂ | H | |
| 184 | 1 | 4 | | H | |
| 185 | 1 | 4 | S | CH₃ | |

TABLE 3-continued

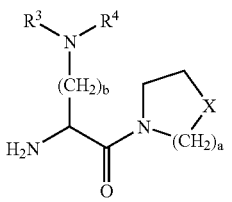

| Ex No | a | b | X | R³ | R⁴ |
|---|---|---|---|---|---|
| 186 | 1 | 4 | | CH(CH₃)₂ | |
| 187 | 1 | 4 | CH₂ | CH₃ | |
| 188 | 1 | 4 | | CH(CH₃)₂ | |
| 189 | 1 | 3 | S | CH(CH₃)₂ | |
| 190 | 1 | 3 | CH₂ | CH(CH₃)₂ | |
| 191 | 2 | 3 | S | H | |
| 192 | 2 | 4 | | H | |
| 193 | 2 | 3 | CH₂ | H | |
| 194 | 2 | 4 | | H | |
| 195 | 1 | 3 | S | H | 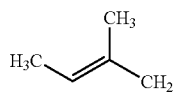 |
| 196 | 1 | 4 | | H | |
| 197 | 1 | 3 | CH₂ | H | |
| 198 | 1 | 4 | | H | |
| 199 | 1 | 3 | CF₂ | H | |
| 200 | 1 | 4 | | H | |
| 201 | 1 | 4 | S | CH₃ | |
| 202 | 1 | 4 | | CH(CH₃)₂ | |
| 203 | 1 | 4 | CH₂ | CH₃ | |
| 204 | 1 | 4 | | CH(CH₃)₂ | |
| 205 | 1 | 3 | S | CH(CH₃)₂ | |
| 206 | 1 | 3 | CH₂ | CH(CH₃)₂ | |
| 207 | 2 | 3 | S | H | |
| 208 | 2 | 4 | | H | |
| 209 | 2 | 3 | CH₂ | H | |
| 210 | 2 | 4 | | H | |
| 211 | 1 | 3 | S | H | 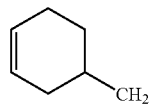 |
| 212 | 1 | 4 | | H | |
| 213 | 1 | 3 | CH₂ | H | |
| 214 | 1 | 4 | | H | |
| 215 | 1 | 3 | CF₂ | H | |
| 216 | 1 | 4 | | H | |
| 217 | 1 | 4 | S | CH₃ | |
| 218 | 1 | 4 | | CH(CH₃)₂ | |
| 219 | 1 | 4 | CH₂ | CH₃ | |
| 220 | 1 | 4 | | CH(CH₃)₂ | |
| 221 | 1 | 3 | S | CH(CH₃)₂ | |
| 222 | 1 | 3 | CH₂ | CH(CH₃)₂ | |
| 223 | 2 | 3 | S | H | |
| 224 | 2 | 3 | CH₂ | H | |
| 225 | 2 | 4 | | H | |
| 226 | 1 | 3 | S | H | 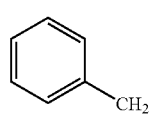 |
| 227 | 1 | 4 | | H | |
| 228 | 1 | 3 | CH₂ | H | |
| 229 | 1 | 4 | | H | |
| 230 | 1 | 3 | CF₂ | H | |
| 231 | 1 | 4 | | H | |
| 232 | 1 | 4 | S | CH₃ | |
| 233 | 1 | 4 | | CH(CH₃)₂ | |

TABLE 3-continued

| Ex No | a | b | X | R³ | R⁴ |
|---|---|---|---|---|---|
| 234 | 1 | 4 | CH₂ | CH₃ | |
| 235 | 1 | 4 | | CH(CH₃)₂ | |
| 236 | 1 | 3 | S | CH(CH₃)₂ | |
| 237 | 1 | 3 | CH₂ | CH(CH₃)₂ | |
| 238 | 2 | 3 | S | H | |
| 239 | 2 | 4 | | H | |
| 240 | 2 | 3 | CH₂ | H | |
| 241 | 2 | 4 | | H | |
| 242 | 1 | 3 | S | H | 3-F-C₆H₄-CH₂ |
| 243 | 1 | 4 | | H | |
| 244 | 1 | 3 | CH₂ | H | |
| 245 | 1 | 4 | | H | |
| 246 | 1 | 3 | CF₂ | H | |
| 247 | 1 | 4 | | H | |
| 248 | 1 | 4 | S | CH₃ | |
| 249 | 1 | 4 | | CH(CH₃)₂ | |
| 250 | 1 | 4 | CH₂ | CH₃ | |
| 251 | 1 | 4 | | CH(CH₃)₂ | |
| 252 | 1 | 3 | S | CH(CH₃)₂ | |
| 253 | 1 | 3 | CH₂ | CH(CH₃)₂ | |
| 254 | 2 | 3 | S | H | |
| 255 | 2 | 4 | | H | |
| 256 | 2 | 3 | CH₂ | H | |
| 257 | 2 | 4 | | H | |
| 258 | 1 | 3 | S | H | 2-Cl-C₆H₄-CH₂ |
| 259 | 1 | 4 | | H | |
| 260 | 1 | 3 | CH₂ | H | |
| 261 | 1 | 4 | | H | |
| 262 | 1 | 3 | CF₂ | H | |
| 263 | 1 | 4 | | H | |
| 264 | 1 | 4 | S | CH₃ | |
| 265 | 1 | 4 | | CH(CH₃)₂ | |
| 266 | 1 | 4 | CH₂ | CH₃ | |
| 267 | 1 | 4 | | CH(CH₃)₂ | |
| 268 | 1 | 3 | S | CH(CH₃)₂ | |
| 269 | 1 | 3 | CH₂ | CH(CH₃)₂ | |
| 270 | 2 | 3 | S | H | |
| 271 | 2 | 4 | | H | |
| 272 | 2 | 3 | CH₂ | H | |
| 273 | 2 | 4 | | H | |
| 274 | 1 | 3 | S | H | 3-Cl-C₆H₄-CH₂ |
| 275 | 1 | 4 | | H | |
| 276 | 1 | 3 | CH₂ | H | |
| 277 | 1 | 4 | | H | |
| 278 | 1 | 3 | CF₂ | H | |
| 279 | 1 | 4 | | H | |
| 280 | 1 | 4 | S | CH₃ | |
| 281 | 1 | 4 | | CH(CH₃)₂ | |
| 282 | 1 | 4 | CH₂ | CH₃ | |
| 283 | 1 | 4 | | CH(CH₃)₂ | |
| 284 | 1 | 3 | S | CH(CH₃)₂ | |
| 285 | 1 | 3 | CH₂ | CH(CH₃)₂ | |
| 286 | 2 | 3 | S | H | |
| 287 | 2 | 4 | | H | |
| 288 | 2 | 3 | CH₂ | H | |
| 289 | 2 | 4 | | H | |
| 290 | 1 | 3 | S | H | 4-Cl-C₆H₄-CH₂ |
| 291 | 1 | 4 | | H | |
| 292 | 1 | 3 | CH₂ | H | |
| 293 | 1 | 4 | | H | |
| 294 | 1 | 3 | CF₂ | H | |
| 295 | 1 | 4 | | H | |
| 296 | 1 | 4 | S | CH₃ | |
| 297 | 1 | 4 | | CH(CH₃)₂ | |
| 298 | 1 | 4 | CH₂ | CH₃ | |
| 299 | 1 | 4 | | CH(CH₃)₂ | |
| 300 | 1 | 3 | S | CH(CH₃)₂ | |
| 301 | 1 | 3 | CH₂ | CH(CH₃)₂ | |
| 302 | 2 | 3 | S | H | |
| 303 | 2 | 4 | | H | |
| 304 | 2 | 3 | CH₂ | H | |
| 305 | 2 | 4 | | H | |
| 306 | 1 | 3 | S | H | 3-CH₃O-C₆H₄-CH₂ |
| 307 | 1 | 4 | | H | |
| 308 | 1 | 3 | CH₂ | H | |
| 309 | 1 | 4 | | H | |
| 310 | 1 | 3 | CF₂ | H | |
| 311 | 1 | 4 | | H | |
| 312 | 1 | 4 | S | CH₃ | |
| 313 | 1 | 4 | | CH(CH₃)₂ | |
| 314 | 1 | 4 | CH₂ | CH₃ | |
| 315 | 1 | 4 | | CH(CH₃)₂ | |
| 316 | 1 | 3 | S | CH(CH₃)₂ | |
| 317 | 1 | 3 | CH₂ | CH(CH₃)₂ | |
| 318 | 2 | 3 | S | H | |
| 319 | 2 | 4 | | H | |
| 320 | 2 | 3 | CH₂ | H | |
| 321 | 2 | 4 | | H | |
| 322 | 1 | 3 | S | H | 4-CH₃O-C₆H₄-CH₂ |
| 323 | 1 | 4 | | H | |
| 324 | 1 | 3 | CH₂ | H | |
| 325 | 1 | 4 | | H | |
| 326 | 1 | 3 | CF₂ | H | |

TABLE 3-continued

| Ex No | a | b | X | R³ | R⁴ |
|---|---|---|---|---|---|
| 327 | 1 | 4 | | H | |
| 328 | 1 | 4 | S | CH₃ | |
| 329 | 1 | 4 | | CH(CH₃)₂ | |
| 330 | 1 | 4 | CH₂ | CH₃ | |
| 331 | 1 | 4 | | CH(CH₃)₂ | |
| 332 | 1 | 3 | S | CH(CH₃)₂ | |
| 333 | 1 | 3 | CH₂ | CH(CH₃)₂ | |
| 334 | 2 | 3 | S | H | |
| 335 | 2 | 4 | | H | |
| 336 | 2 | 3 | CH₂ | H | |
| 337 | 2 | 4 | | H | |
| 338 | 1 | 3 | S | H | 3-acetoxybenzyl (H₃C-C(O)-O-C₆H₄-CH₂, meta) |
| 339 | 1 | 4 | | H | |
| 340 | 1 | 3 | CH₂ | H | |
| 341 | 1 | 4 | | H | |
| 342 | 1 | 3 | CF₂ | H | |
| 343 | 1 | 4 | | H | |
| 344 | 1 | 4 | S | CH₃ | |
| 345 | 1 | 4 | | CH(CH₃)₂ | |
| 346 | 1 | 4 | CH₂ | CH₃ | |
| 347 | 1 | 4 | | CH(CH₃)₂ | |
| 348 | 1 | 3 | S | CH(CH₃)₂ | |
| 349 | 1 | 3 | CH₂ | CH(CH₃)₂ | |
| 350 | 2 | 3 | S | H | |
| 351 | 2 | 4 | | H | |
| 352 | 2 | 3 | CH₂ | H | |
| 353 | 2 | 4 | | H | |
| 354 | 1 | 3 | S | H | 4-acetoxybenzyl |
| 355 | 1 | 4 | | H | |
| 356 | 1 | 3 | CH₂ | H | |
| 357 | 1 | 4 | | H | |
| 358 | 1 | 3 | CF₂ | H | |
| 359 | 1 | 4 | | H | |
| 360 | 1 | 4 | S | CH₃ | |
| 361 | 1 | 4 | | CH(CH₃)₂ | |
| 362 | 1 | 4 | CH₂ | CH₃ | |
| 363 | 1 | 4 | | CH(CH₃)₂ | |
| 364 | 1 | 3 | S | CH(CH₃)₂ | |
| 365 | 1 | 3 | CH₂ | CH(CH₃)₂ | |
| 366 | 2 | 3 | S | H | |
| 367 | 2 | 4 | | H | |
| 368 | 2 | 3 | CH₂ | H | |
| 369 | 2 | 4 | | H | |
| 370 | 1 | 3 | S | H | 4-(dimethylamino)benzyl |
| 371 | 1 | 4 | | H | |
| 372 | 1 | 3 | CH₂ | H | |
| 373 | 1 | 4 | | H | |
| 374 | 1 | 3 | CF₂ | H | |
| 375 | 1 | 4 | | H | |
| 376 | 1 | 4 | S | CH₃ | |
| 377 | 1 | 4 | | CH(CH₃)₂ | |
| 378 | 1 | 4 | CH₂ | CH₃ | |
| 379 | 1 | 4 | | CH(CH₃)₂ | |
| 380 | 1 | 3 | S | CH(CH₃)₂ | |
| 381 | 1 | 3 | CH₂ | CH(CH₃)₂ | |
| 382 | 2 | 3 | S | H | |
| 383 | 2 | 4 | | H | |
| 384 | 2 | 3 | CH₂ | H | |
| 385 | 2 | 4 | | H | |
| 386 | 1 | 3 | S | H | 4-acetamidobenzyl |
| 387 | 1 | 4 | | H | |
| 388 | 1 | 3 | CH₂ | H | |
| 389 | 1 | 4 | | H | |
| 390 | 1 | 3 | CF₂ | H | |
| 391 | 1 | 4 | | H | |
| 392 | 1 | 4 | S | CH₃ | |
| 393 | 1 | 4 | | CH(CH₃)₂ | |
| 394 | 1 | 4 | CH₂ | CH₃ | |
| 395 | 1 | 4 | | CH(CH₃)₂ | |
| 396 | 1 | 3 | S | CH(CH₃)₂ | |
| 397 | 1 | 3 | CH₂ | CH(CH₃)₂ | |
| 398 | 2 | 3 | S | H | |
| 399 | 2 | 4 | | H | |
| 400 | 2 | 3 | CH₂ | H | |
| 401 | 2 | 4 | | H | |
| 402 | 1 | 3 | S | H | 3-(methoxycarbonyl)benzyl |
| 403 | 1 | 4 | | H | |
| 404 | 1 | 3 | CH₂ | H | |
| 405 | 1 | 4 | | H | |
| 406 | 1 | 3 | CF₂ | H | |
| 407 | 1 | 4 | | H | |
| 408 | 1 | 4 | S | CH₃ | |
| 409 | 1 | 4 | | CH(CH₃)₂ | |
| 410 | 1 | 4 | CH₂ | CH₃ | |
| 411 | 1 | 4 | | CH(CH₃)₂ | |
| 412 | 1 | 3 | S | CH(CH₃)₂ | |
| 413 | 1 | 3 | CH₂ | CH(CH₃)₂ | |
| 414 | 2 | 3 | S | H | |
| 415 | 2 | 4 | | H | |
| 416 | 2 | 3 | CH₂ | H | |
| 417 | 2 | 4 | | H | |

TABLE 3-continued

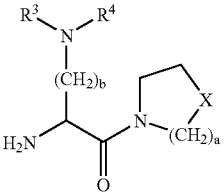

| Ex No | a | b | X | R³ | R⁴ |
|---|---|---|---|---|---|
| 418 | 1 | 3 | S | H | 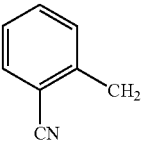 (2-CN-benzyl, CH₂) |
| 419 | 1 | 4 | | H | |
| 420 | 1 | 3 | CH₂ | H | |
| 421 | 1 | 4 | | H | |
| 422 | 1 | 3 | CF₂ | H | |
| 423 | 1 | 4 | | H | |
| 424 | 1 | 4 | S | CH₃ | |
| 425 | 1 | 4 | | CH(CH₃)₂ | |
| 426 | 1 | 4 | CH₂ | CH₃ | |
| 427 | 1 | 4 | | CH(CH₃)₂ | |
| 428 | 1 | 3 | S | CH(CH₃)₂ | |
| 429 | 1 | 3 | CH₂ | CH(CH₃)₂ | |
| 450 | 2 | 3 | S | H | |
| 451 | 2 | 4 | | H | |
| 452 | 2 | 3 | CH₂ | H | |
| 453 | 2 | 4 | | H | |
| 454 | 1 | 3 | S | H | 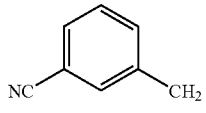 (3-CN-benzyl, CH₂) |
| 455 | 1 | 4 | | H | |
| 456 | 1 | 3 | CH₂ | H | |
| 457 | 1 | 4 | | H | |
| 458 | 1 | 3 | CF₂ | H | |
| 459 | 1 | 4 | | H | |
| 460 | 1 | 4 | S | CH₃ | |
| 461 | 1 | 4 | | CH(CH₃)₂ | |
| 462 | 1 | 4 | CH₂ | CH₃ | |
| 463 | 1 | 4 | | CH(CH₃)₂ | |
| 464 | 1 | 3 | S | CH(CH₃)₂ | |
| 465 | 1 | 3 | CH₂ | CH(CH₃)₂ | |
| 466 | 2 | 3 | S | H | |
| 467 | 2 | 4 | | H | |
| 468 | 2 | 3 | CH₂ | H | |
| 469 | 2 | 4 | | H | |
| 470 | 1 | 3 | S | H | 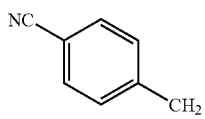 (4-CN-benzyl, CH₂) |
| 471 | 1 | 4 | | H | |
| 472 | 1 | 3 | CH₂ | H | |
| 473 | 1 | 4 | | H | |
| 474 | 1 | 3 | CF₂ | H | |
| 475 | 1 | 4 | | H | |
| 476 | 1 | 4 | S | CH₃ | |
| 477 | 1 | 4 | | CH(CH₃)₂ | |
| 478 | 1 | 4 | CH₂ | CH₃ | |
| 479 | 1 | 4 | | CH(CH₃)₂ | |
| 480 | 1 | 3 | S | CH(CH₃)₂ | |
| 481 | 1 | 3 | CH₂ | CH(CH₃)₂ | |
| 482 | 2 | 3 | S | H | |
| 483 | 2 | 4 | | H | |

TABLE 3-continued

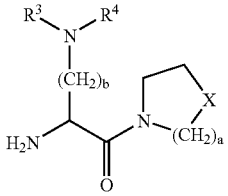

| Ex No | a | b | X | R³ | R⁴ |
|---|---|---|---|---|---|
| 484 | 2 | 3 | CH₂ | H | |
| 485 | 2 | 4 | | H | |
| 486 | 1 | 3 | S | H | 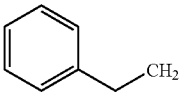 (phenethyl, CH₂) |
| 487 | 1 | 4 | | H | |
| 488 | 1 | 3 | CH₂ | H | |
| 489 | 1 | 4 | | H | |
| 490 | 1 | 3 | CF₂ | H | |
| 491 | 1 | 4 | | H | |
| 492 | 1 | 4 | S | CH₃ | |
| 493 | 1 | 4 | | CH(CH₃)₂ | |
| 494 | 1 | 4 | CH₂ | CH₃ | |
| 495 | 1 | 4 | | CH(CH₃)₂ | |
| 496 | 1 | 3 | S | CH(CH₃)₂ | |
| 497 | 1 | 3 | CH₂ | CH(CH₃)₂ | |
| 498 | 2 | 3 | S | H | |
| 499 | 2 | 4 | | H | |
| 500 | 2 | 3 | CH₂ | H | |
| 501 | 2 | 4 | | H | |
| 502 | 1 | 3 | S | H | 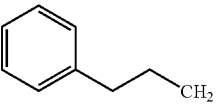 (3-phenylpropyl, CH₂) |
| 503 | 1 | 4 | | H | |
| 504 | 1 | 3 | CH₂ | H | |
| 505 | 1 | 4 | | H | |
| 506 | 1 | 3 | CF₂ | H | |
| 507 | 1 | 4 | | H | |
| 508 | 1 | 4 | S | CH₃ | |
| 509 | 1 | 4 | | CH(CH₃)₂ | |
| 510 | 1 | 4 | CH₂ | CH₃ | |
| 511 | 1 | 4 | | CH(CH₃)₂ | |
| 512 | 1 | 3 | S | CH(CH₃)₂ | |
| 513 | 1 | 3 | CH₂ | CH(CH₃)₂ | |
| 514 | 2 | 3 | S | H | |
| 515 | 2 | 4 | | H | |
| 516 | 2 | 3 | CH₂ | H | |
| 517 | 2 | 4 | | H | |
| 518 | 1 | 3 | S | H | 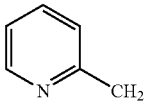 (2-pyridylmethyl, CH₂) |
| 519 | 1 | 4 | | H | |
| 520 | 1 | 3 | CH₂ | H | |
| 521 | 1 | 4 | | H | |
| 522 | 1 | 3 | CF₂ | H | |
| 523 | 1 | 4 | | H | |
| 524 | 1 | 4 | S | CH₃ | |
| 525 | 1 | 4 | | CH(CH₃)₂ | |
| 526 | 1 | 4 | CH₂ | CH₃ | |
| 527 | 1 | 4 | | CH(CH₃)₂ | |
| 528 | 1 | 3 | S | CH(CH₃)₂ | |
| 529 | 1 | 3 | CH₂ | CH(CH₃)₂ | |
| 530 | 2 | 3 | S | H | |
| 531 | 2 | 4 | | H | |

TABLE 3-continued

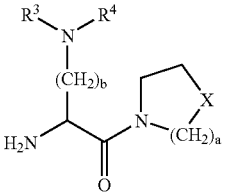

| Ex No | a | b | X | R³ | R⁴ |
|---|---|---|---|---|---|
| 532 | 2 | 3 | CH₂ | H | |
| 533 | 2 | 4 | | H | |
| 534 | 1 | 3 | S | H | 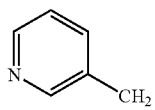 3-pyridyl-CH₂ |
| 535 | 1 | 4 | | H | |
| 536 | 1 | 3 | CH₂ | H | |
| 537 | 1 | 4 | | H | |
| 538 | 1 | 3 | CF₂ | H | |
| 539 | 1 | 4 | | H | |
| 540 | 1 | 4 | S | CH₃ | |
| 541 | 1 | 4 | | CH(CH₃)₂ | |
| 542 | 1 | 4 | CH₂ | CH₃ | |
| 543 | 1 | 4 | | CH(CH₃)₂ | |
| 544 | 1 | 3 | S | CH(CH₃)₂ | |
| 545 | 1 | 3 | CH₂ | CH(CH₃)₂ | |
| 546 | 2 | 3 | S | H | |
| 547 | 2 | 4 | | H | |
| 548 | 2 | 3 | CH₂ | H | |
| 549 | 2 | 4 | | H | |
| 550 | 1 | 3 | S | H | 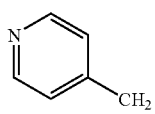 4-pyridyl-CH₂ |
| 551 | 1 | 4 | | H | |
| 552 | 1 | 3 | CH₂ | H | |
| 553 | 1 | 4 | | H | |
| 554 | 1 | 3 | CF₂ | H | |
| 555 | 1 | 4 | | H | |
| 556 | 1 | 4 | S | CH₃ | |
| 557 | 1 | 4 | | CH(CH₃)₂ | |
| 558 | 1 | 4 | CH₂ | CH₃ | |
| 559 | 1 | 4 | | CH(CH₃)₂ | |
| 560 | 1 | 3 | S | CH(CH₃)₂ | |
| 561 | 1 | 3 | CH₂ | CH(CH₃)₂ | |
| 562 | 2 | 3 | S | H | |
| 563 | 2 | 4 | | H | |
| 564 | 2 | 3 | CH₂ | H | |
| 565 | 2 | 4 | | H | |
| 566 | 1 | 3 | S | H | 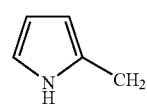 1H-pyrrol-2-yl-CH₂ |
| 567 | 1 | 4 | | H | |
| 568 | 1 | 3 | CH₂ | H | |
| 569 | 1 | 4 | | H | |
| 570 | 1 | 3 | CF₂ | H | |
| 571 | 1 | 4 | | H | |
| 572 | 1 | 4 | S | CH₃ | |
| 573 | 1 | 4 | | CH(CH₃)₂ | |
| 574 | 1 | 4 | CH₂ | CH₃ | |
| 575 | 1 | 4 | | CH(CH₃)₂ | |
| 576 | 1 | 3 | S | CH(CH₃)₂ | |
| 577 | 1 | 3 | CH₂ | CH(CH₃)₂ | |
| 578 | 2 | 3 | S | H | |
| 579 | 2 | 4 | | H | |
| 580 | 2 | 3 | CH₂ | H | |
| 581 | 2 | 4 | | H | |
| 582 | 1 | 3 | S | H | 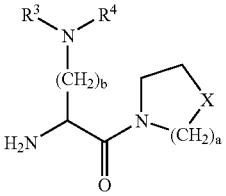 1-methyl-1H-pyrrol-2-yl-CH₂ |
| 583 | 1 | 4 | | H | |
| 584 | 1 | 3 | CH₂ | H | |
| 585 | 1 | 4 | | H | |
| 586 | 1 | 3 | CF₂ | H | |
| 587 | 1 | 4 | | H | |
| 588 | 1 | 4 | S | CH₃ | |
| 589 | 1 | 4 | | CH(CH₃)₂ | |
| 590 | 1 | 4 | CH₂ | CH₃ | |
| 591 | 1 | 4 | | CH(CH₃)₂ | |
| 592 | 1 | 3 | S | CH(CH₃)₂ | |
| 593 | 1 | 3 | CH₂ | CH(CH₃)₂ | |
| 594 | 2 | 3 | S | H | |
| 595 | 2 | 4 | | H | |
| 596 | 2 | 3 | CH₂ | H | |
| 597 | 2 | 4 | | H | |
| 598 | 1 | 3 | S | H | thiophen-2-yl-CH₂ |
| 599 | 1 | 4 | | H | |
| 600 | 1 | 3 | CH₂ | H | |
| 601 | 1 | 4 | | H | |
| 602 | 1 | 3 | CF₂ | H | |
| 603 | 1 | 4 | | H | |
| 604 | 1 | 4 | S | CH₃ | |
| 605 | 1 | 4 | | CH(CH₃)₂ | |
| 606 | 1 | 4 | CH₂ | CH₃ | |
| 607 | 1 | 4 | | CH(CH₃)₂ | |
| 608 | 1 | 3 | S | CH(CH₃)₂ | |
| 609 | 1 | 3 | CH₂ | CH(CH₃)₂ | |
| 610 | 2 | 3 | S | H | |
| 611 | 2 | 4 | | H | |
| 612 | 2 | 3 | CH₂ | H | |
| 613 | 2 | 4 | | H | |
| 614 | 1 | 3 | S | H | thiophen-3-yl-CH₂ |
| 615 | 1 | 4 | | H | |
| 616 | 1 | 3 | CH₂ | H | |
| 617 | 1 | 4 | | H | |
| 618 | 1 | 3 | CF₂ | H | |
| 619 | 1 | 4 | | H | |
| 620 | 1 | 4 | S | CH₃ | |
| 621 | 1 | 4 | | CH(CH₃)₂ | |
| 622 | 1 | 4 | CH₂ | CH₃ | |
| 623 | 1 | 4 | | CH(CH₃)₂ | |
| 624 | 1 | 3 | S | CH(CH₃)₂ | |
| 625 | 1 | 3 | CH₂ | CH(CH₃)₂ | |
| 626 | 2 | 3 | S | H | |
| 627 | 2 | 4 | | H | |
| 628 | 2 | 3 | CH₂ | H | |

TABLE 3-continued

| Ex No | a | b | X | R³ | R⁴ |
|---|---|---|---|---|---|
| 629 | 2 | 4 | | H | |
| 630 | 1 | 3 | S | H | 1-naphthylmethyl |
| 631 | 1 | 4 | | H | |
| 632 | 1 | 3 | CH₂ | H | |
| 633 | 1 | 4 | | H | |
| 634 | 1 | 3 | CF₂ | H | |
| 635 | 1 | 4 | | H | |
| 636 | 1 | 4 | S | CH₃ | |
| 637 | 1 | 4 | | CH(CH₃)₂ | |
| 638 | 1 | 4 | CH₂ | CH₃ | |
| 639 | 1 | 4 | | CH(CH₃)₂ | |
| 640 | 1 | 3 | S | CH(CH₃)₂ | |
| 641 | 1 | 3 | CH₂ | CH(CH₃)₂ | |
| 642 | 2 | 3 | S | H | |
| 643 | 2 | 4 | | H | |
| 644 | 2 | 3 | CH₂ | H | |
| 645 | 2 | 4 | | H | |
| 646 | 1 | 3 | S | H | 2-naphthylmethyl |
| 647 | 1 | 4 | | H | |
| 648 | 1 | 3 | CH₂ | H | |
| 649 | 1 | 4 | | H | |
| 650 | 1 | 3 | CF₂ | H | |
| 651 | 1 | 4 | | H | |
| 652 | 1 | 4 | S | CH(CH₃)₂ | |
| 653 | 1 | 4 | CH₂ | CH₃ | |
| 654 | 1 | 4 | | CH(CH₃)₂ | |
| 655 | 1 | 3 | S | CH(CH₃)₂ | |
| 656 | 1 | 3 | CH₂ | CH(CH₃)₂ | |
| 657 | 2 | 3 | S | H | |
| 658 | 2 | 4 | | H | |
| 659 | 2 | 3 | CH₂ | H | |
| 660 | 2 | 4 | | H | |
| 661 | 1 | 3 | S | H | quinolin-2-ylmethyl |
| 662 | 1 | 4 | | H | |
| 663 | 1 | 3 | CH₂ | H | |
| 664 | 1 | 4 | | H | |
| 665 | 1 | 3 | CF₂ | H | |
| 666 | 1 | 4 | | H | |
| 667 | 1 | 4 | S | CH₃ | |
| 668 | 1 | 4 | | CH(CH₃)₂ | |
| 669 | 1 | 4 | CH₂ | CH₃ | |
| 670 | 1 | 4 | | CH(CH₃)₂ | |
| 671 | 1 | 3 | S | CH(CH₃)₂ | |
| 672 | 1 | 3 | CH₂ | CH(CH₃)₂ | |
| 673 | 2 | 3 | S | H | |
| 674 | 2 | 4 | | H | |
| 675 | 2 | 3 | CH₂ | H | |
| 676 | 2 | 4 | | H | |
| 677 | 1 | 3 | S | H | quinolin-3-ylmethyl |
| 678 | 1 | 4 | CH₂ | H | |
| 679 | 1 | 3 | CF₂ | H | |
| 680 | 1 | 4 | | H | |
| 681 | 1 | 4 | S | CH₃ | |
| 682 | 1 | 4 | | CH(CH₃)₂ | |
| 683 | 1 | 4 | CH₂ | CH₃ | |
| 684 | 1 | 4 | | CH(CH₃)₂ | |
| 685 | 1 | 3 | S | CH(CH₃)₂ | |
| 686 | 1 | 3 | CH₂ | CH(CH₃)₂ | |
| 687 | 2 | 3 | S | H | |
| 688 | 2 | 4 | CH₂ | H | |
| 689 | 1 | 3 | S | H | quinolin-4-ylmethyl |
| 690 | 1 | 4 | | H | |
| 691 | 1 | 3 | CH₂ | H | |
| 692 | 1 | 4 | | H | |
| 693 | 1 | 3 | CF₂ | H | |
| 694 | 1 | 4 | | H | |
| 695 | 1 | 4 | S | CH₃ | |
| 696 | 1 | 4 | | CH(CH₃)₂ | |
| 697 | 1 | 4 | CH₂ | CH₃ | |
| 698 | 1 | 4 | | CH(CH₃)₂ | |
| 699 | 1 | 3 | S | CH(CH₃)₂ | |
| 700 | 1 | 3 | CH₂ | CH(CH₃)₂ | |
| 701 | 2 | 3 | S | H | |
| 702 | 2 | 4 | | H | |
| 703 | 2 | 3 | CH₂ | H | |
| 704 | 2 | 4 | | H | |
| 705 | 1 | 3 | S | H | 1H-indol-3-ylmethyl |
| 706 | 1 | 4 | | H | |
| 707 | 1 | 3 | CH₂ | H | |
| 708 | 1 | 4 | | H | |
| 709 | 1 | 3 | CF₂ | H | |
| 710 | 1 | 4 | | H | |
| 711 | 1 | 4 | S | CH₃ | |
| 712 | 1 | 4 | | CH(CH₃)₂ | |
| 713 | 1 | 4 | CH₂ | CH₃ | |
| 714 | 1 | 4 | | CH(CH₃)₂ | |
| 715 | 1 | 3 | S | CH(CH₃)₂ | |
| 716 | 1 | 3 | CH₂ | CH(CH₃)₂ | |

TABLE 3-continued

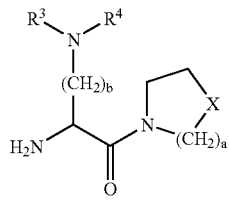

| Ex No | a | b | X | R³ | R⁴ |
|---|---|---|---|---|---|
| 717 | 2 | 3 | S | H | |
| 718 | 2 | 4 | | H | |
| 719 | 2 | 3 | CH₂ | H | |
| 720 | 2 | 4 | | H | |
| 721 | 1 | 3 | S | H | 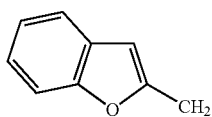 |
| 722 | 1 | 4 | | H | |
| 723 | 1 | 3 | CH₂ | H | |
| 724 | 1 | 4 | | H | |
| 725 | 1 | 3 | CF₂ | H | |
| 726 | 1 | 4 | | H | |
| 727 | 1 | 4 | S | CH₃ | |
| 728 | 1 | 4 | | CH(CH₃)₂ | |
| 729 | 1 | 4 | CH₂ | CH₃ | |
| 730 | 1 | 4 | | CH(CH₃)₂ | |
| 731 | 1 | 3 | S | CH(CH₃)₂ | |
| 732 | 1 | 3 | CH₂ | CH(CH₃)₂ | |
| 733 | 2 | 3 | S | H | |
| 734 | 2 | 4 | | H | |
| 735 | 2 | 3 | CH₂ | H | |
| 736 | 2 | 4 | | H | |
| 737 | 1 | 3 | S | H | 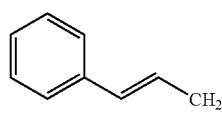 |
| 738 | 1 | 3 | CH₂ | H | |
| 739 | 1 | 4 | | H | |
| 740 | 1 | 3 | CH₂ | H | |
| 741 | 1 | 4 | | H | |
| 742 | 1 | 4 | S | CH₃ | |
| 743 | 1 | 4 | | CH(CH₃)₂ | |
| 744 | 1 | 4 | CH₂ | CH₃ | |
| 745 | 1 | 4 | | CH(CH₃)₂ | |
| 746 | 1 | 3 | S | CH(CH₃)₂ | |
| 747 | 1 | 3 | CH₂ | CH(CH₃)₂ | |
| 748 | 2 | 3 | S | H | |
| 749 | 2 | 4 | | H | |
| 750 | 2 | 3 | CH₂ | H | |
| 751 | 2 | 4 | | H | |
| 752 | 1 | 3 | S | H | 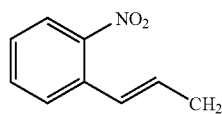 |
| 753 | 1 | 4 | | H | |
| 754 | 1 | 3 | CH₂ | H | |
| 755 | 1 | 4 | | H | |
| 756 | 1 | 3 | CF₂ | H | |
| 757 | 1 | 4 | | H | |
| 758 | 1 | 4 | S | CH₃ | |
| 759 | 1 | 4 | | CH(CH₃)₂ | |
| 760 | 1 | 4 | CH₂ | CH₃ | |
| 761 | 1 | 4 | | CH(CH₃)₂ | |
| 762 | 1 | 3 | S | CH(CH₃)₂ | |
| 763 | 1 | 3 | CH₂ | CH(CH₃)₂ | |

TABLE 3-continued

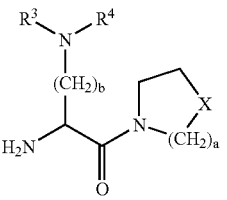

| Ex No | a | b | X | R³ | R⁴ |
|---|---|---|---|---|---|
| 764 | 2 | 3 | S | H | |
| 765 | 2 | 4 | | H | |
| 766 | 2 | 3 | CH₂ | H | |
| 767 | 2 | 4 | | H | |
| 768 | 1 | 3 | S | H | 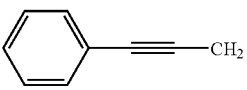 |
| 769 | 1 | 4 | | H | |
| 770 | 1 | 3 | CH₂ | H | |
| 771 | 1 | 4 | | H | |
| 772 | 1 | 3 | CF₂ | H | |
| 773 | 1 | 4 | | H | |
| 774 | 1 | 4 | S | CH₃ | |
| 775 | 1 | 4 | | CH(CH₃)₂ | |
| 776 | 1 | 4 | CH₂ | CH₃ | |
| 777 | 1 | 4 | | CH(CH₃)₂ | |
| 778 | 1 | 3 | S | CH(CH₃)₂ | |
| 779 | 1 | 3 | CH₂ | CH(CH₃)₂ | |
| 780 | 2 | 3 | S | H | |
| 781 | 2 | 4 | | H | |
| 782 | 2 | 3 | CH₂ | H | |
| 783 | 2 | 4 | | H | |
| 784 | 1 | 3 | S | H | |
| 785 | 1 | 4 | | H | |
| 786 | 1 | 3 | CH₂ | H | |
| 787 | 1 | 4 | | H | |
| 788 | 1 | 3 | CF₂ | H | |
| 789 | 1 | 4 | | H | |
| 790 | 1 | 4 | S | CH₃ | |
| 791 | 1 | 4 | | CH(CH₃)₂ | |
| 792 | 1 | 4 | CH₂ | CH₃ | |
| 793 | 1 | 4 | | CH(CH₃)₂ | |
| 794 | 1 | 3 | S | CH(CH₃)₂ | |
| 795 | 1 | 3 | CH₂ | CH(CH₃)₂ | |
| 796 | 2 | 3 | S | H | |
| 797 | 2 | 4 | | H | |
| 798 | 2 | 3 | CH₂ | H | |
| 799 | 2 | 4 | | H | |

TABLE 4

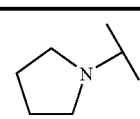

| Example No | X | R |
|---|---|---|
| 800 | S | |
| 801 | CH₂ | |

TABLE 4-continued
| Example No | X | R |
|---|---|---|
| 802 | S | 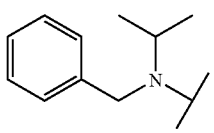 |
| 803 | CH₂ | |
| 804 | S | 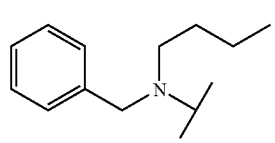 |
| 805 | CH₂ | |
| 806 | S | 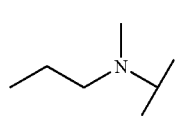 |
| 807 | CH₂ | |
| 808 | S | 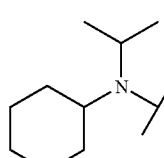 |
| 809 | CH₂ | |
| 810 | S | 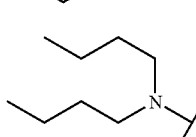 |
| 811 | CH₂ | |
| 812 | S | 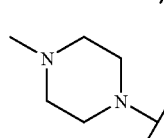 |
| 813 | CH₂ | |
| 814 | S | 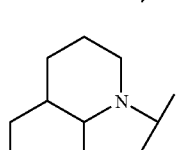 |
| 815 | CH₂ | |
| 816 | S | 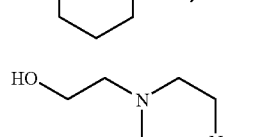 |
| 817 | CH₂ | |
| 818 | S | 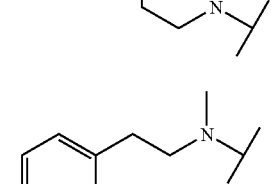 |
| 819 | CH₂ | |
TABLE 4-continued
| Example No | X | R |
|---|---|---|
| 820 | S | 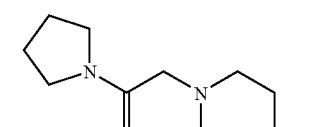 |
| 821 | CH₂ | |
| 822 | S | 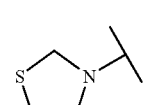 |
| 823 | CH₂ | |
| 824 | S | 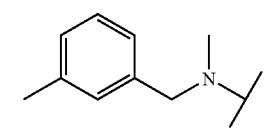 |
| 825 | CH₂ | |
| 826 | S | 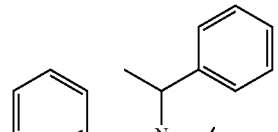 |
| 827 | CH₂ | |
| 828 | | CH₂ 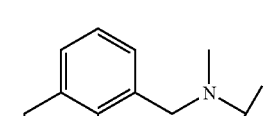 |
| 829 | | |
| 830 | S | 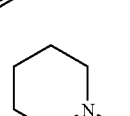 |
| 831 | CH₂ | |
| 832 | S | 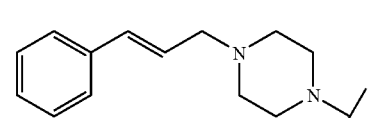 |
| 833 | CH₂ | |
| 834 | S | 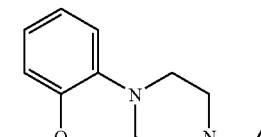 |
| 835 | CH₂ | |

TABLE 4-continued

| Example No | X | R |
|---|---|---|
| 836 | S | (diphenylmethyl)(methyl)amino |
| 837 | CH₂ | |
| 838 | S | 4-phenylpiperazin-1-yl |
| 839 | CH₂ | |
| 841 | S | dibenzylamino |
| 842 | CH₂ | |
| 843 | S | benzyl(methyl)amino |
| 844 | CH₂ | |
| 845 | S | 3,4-dihydroisoquinolin-2(1H)-yl |
| 846 | CH₂ | |
| 847 | CH₂ | hexyl(methyl)amino |
| 848 | S | diethylamino |
| 849 | CH₂ | |
| 850 | S | butyl(methyl)amino |
| 851 | CH₂ | |
| 852 | S | azepan-1-yl |
| 853 | CH₂ | |
| 854 | S | decahydroisoquinolin-2-yl |
| 855 | CH₂ | |
| 856 | S | 4-(ethoxycarbonyl)piperidin-1-yl |
| 857 | CH₂ | |
| 858 | S | (ethoxycarbonylmethyl)(phenethyl)amino |
| 859 | CH₂ | |
| 860 | S | 4-(pyridin-2-yl)piperazin-1-yl |
| 861 | CH₂ | |
| 862 | S | (2-methylbenzyl)(methyl)amino |
| 863 | CH₂ | |
| 864 | S | (2-chlorobenzyl)(methyl)amino |
| 865 | CH₂ | |
| 866 | S | benzyl(2-(dimethylamino)ethyl)amino |
| 867 | CH₂ | |

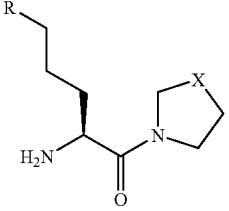

TABLE 4-continued

Structure: R-CH2-CH2-C(NH2)(H)-C(=O)-N(ring with X)

| Example No | X | R |
|---|---|---|
| 868 | S | N,N-diallyl-amino group |
| 869 | CH₂ | N,N-diallyl-amino group |
| 870 | S | N-methyl-N-(2-(pyridin-2-yl)ethyl)amino |
| 871 | CH₂ | N-methyl-N-(2-(pyridin-2-yl)ethyl)amino |
| 872 | S | 4-(3,4-dichlorophenyl)piperazin-1-yl |
| 873 | CH₂ | 4-(3,4-dichlorophenyl)piperazin-1-yl |
| 874 | S | 4-benzylpiperidin-1-yl |
| 875 | CH₂ | 4-benzylpiperidin-1-yl |
| 876 | S | N-methyl-N-(indan-1-yl)amino |
| 877 | CH₂ | N-methyl-N-(indan-1-yl)amino |

TABLE 5

Structure: 2-R-pyridin-3-yl-C(=O)-NH-CH(-(CH2)n-ring with X)-C(NH2)(H)-C(=O)-

| Example No | n | X | R |
|---|---|---|---|
| 878 | 3 | S | 4-methoxyphenylamino |
| 879 | 4 | CH₂ | 4-methoxyphenylamino |
| 880 | 3 | | 4-methoxyphenylamino |
| 881 | 4 | | 4-methoxyphenylamino |

TABLE 5-continued

| Example No | n | X | R |
|---|---|---|---|
| 882 | 3 | S | 3-chlorophenylamino |
| 883 | 4 | CH₂ | 3-chlorophenylamino |
| 884 | 3 | | 3-chlorophenylamino |
| 885 | 4 | | 3-chlorophenylamino |
| 886 | 3 | S | phenylamino |
| 887 | 4 | CH₂ | phenylamino |
| 888 | 3 | | phenylamino |
| 889 | 4 | | phenylamino |
| 890 | 3 | S | 4-methylphenylamino |
| 891 | 4 | CH₂ | 4-methylphenylamino |
| 892 | 3 | | 4-methylphenylamino |
| 893 | 4 | | 4-methylphenylamino |
| 894 | 3 | S | 4-nitrophenylamino |
| 895 | 4 | CH₂ | 4-nitrophenylamino |
| 896 | 3 | | 4-nitrophenylamino |
| 897 | 4 | | 4-nitrophenylamino |
| 898 | 3 | S | 4-tert-butylphenylamino |
| 899 | 4 | CH₂ | 4-tert-butylphenylamino |
| 900 | 3 | | 4-tert-butylphenylamino |
| 901 | 4 | | 4-tert-butylphenylamino |
| 902 | 3 | S | 3,5-dimethylphenylamino |
| 903 | 4 | CH₂ | 3,5-dimethylphenylamino |
| 904 | 3 | | 3,5-dimethylphenylamino |
| 905 | 4 | | 3,5-dimethylphenylamino |
| 906 | 3 | S | 3,4-dichlorophenylamino |
| 907 | 4 | CH₂ | 3,4-dichlorophenylamino |
| 908 | 3 | | 3,4-dichlorophenylamino |
| 909 | 4 | | 3,4-dichlorophenylamino |
| 910 | 3 | S | 2,5-dichlorophenylamino |
| 911 | 4 | CH₂ | 2,5-dichlorophenylamino |
| 912 | 3 | | 2,5-dichlorophenylamino |
| 913 | 4 | | 2,5-dichlorophenylamino |

TABLE 5-continued
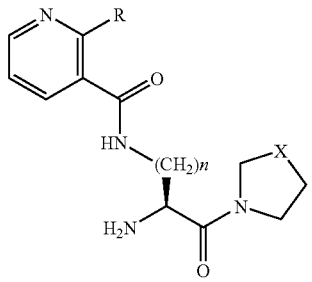
| Example No | n | X | R |
|---|---|---|---|
| 914 | 3 | S | ![benzodioxole-NH] |
| 915 | 4 | CH₂ | |
| 916 | 3 | | |
| 917 | 4 | | |
| 918 | 3 | S | 4-CF₃O-C₆H₄-NH- |
| 919 | 4 | CH₂ | |
| 920 | 3 | | |
| 0 | 4 | | |
| 921 | 3 | S | 3-Et-C₆H₄-NH- |
| 922 | 4 | CH₂ | |
| 923 | 3 | | |
| 924 | 4 | | |
| 925 | 3 | S | PhO-CH-NH- (phenoxy) |
| 926 | 4 | CH₂ | |
| 927 | 3 | | |
| 928 | 4 | | |
| 929 | 3 | S | Me |
| 930 | 4 | | |
| 931 | 3 | CH₂ | |
| 932 | 4 | | |
| 933 | 3 | S | 4-Cl-C₆H₄-NH- |
| 934 | 4 | CH₂ | |
| 935 | 3 | | |
| 936 | 4 | | |
| 937 | 3 | S | 2-Cl-C₆H₄-NH- |
| 938 | 4 | CH₂ | |
| 939 | 3 | | |
| 940 | 4 | | |
| 941 | 3 | S | 3,4-diMe-C₆H₃-NH- |
| 942 | 4 | CH₂ | |
| 943 | 3 | | |
| 944 | 4 | | |
| 945 | 3 | S | 4-F-C₆H₄-NH- |
| 946 | 4 | CH₂ | |
TABLE 5-continued
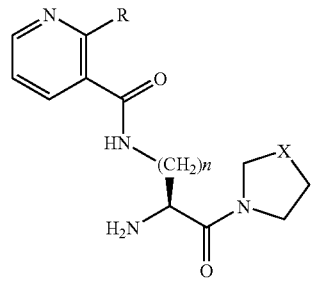
| Example No | n | X | R |
|---|---|---|---|
| 947 | 3 | S | 3-NO₂-C₆H₄-NH- |
| 948 | 4 | CH₂ | |
| 949 | 3 | | |
| 950 | 4 | | |
| 951 | 3 | S | 3-Me-C₆H₄-NH- |
| 952 | 4 | CH₂ | |
| 953 | 3 | | |
| 954 | 4 | | |
| 955 | 3 | S | 3-MeO-C₆H₄-NH- |
| 956 | 4 | CH₂ | |
| 957 | 3 | | |
| 958 | 4 | | |
| 959 | 3 | S | 3,5-diCl-C₆H₃-NH- |
| 960 | 4 | CH₂ | |
| 961 | 3 | | |
| 962 | 4 | | |
| 963 | 3 | S | 2,3-diCl-C₆H₃-NH- |
| 964 | 4 | CH₂ | |
| 965 | 3 | | |
| 966 | 4 | | |
| 967 | 3 | S | tetrahydroquinolin-1-yl |
| 968 | 4 | CH₂ | |
| 969 | 3 | | |
| 970 | 4 | | |
| 971 | 3 | S | 3-iPr-C₆H₄-NH- |
| 972 | 4 | CH₂ | |
| 973 | 3 | | |
| 974 | 4 | | |
| 975 | 4 | S | 3-CF₃-C₆H₄-NH- |
| 976 | 3 | CH₂ | |
| 977 | 4 | | |
| 978 | | | |
| 979 | 3 | S | MeS |
| 980 | 4 | | |
| 981 | 3 | CH₂ | |

TABLE 5-continued

| Example No | n | X | R |
|---|---|---|---|
| 982 | 4 | | |
| 983 | 3 | S | MeO |
| 984 | 4 | | |
| 985 | 3 | CH₂ | |
| 986 | 4 | | |

TABLE 6

| Example No | n | X | R |
|---|---|---|---|
| 987 | 3 | S | 4-methoxyphenyl-NH-CH(CH₃)- |
| 988 | 4 | CH₂ | |
| 989 | 3 | | |
| 990 | 4 | | |
| 991 | 4 | S | 3-chlorophenyl-NH-CH(CH₃)- |
| 992 | 3 | CH₂ | |
| 993 | 4 | | |
| 994 | | | |
| 995 | 3 | S | phenyl-NH-CH(CH₃)- |
| 996 | 4 | CH₂ | |
| 997 | 3 | | |
| 998 | 4 | | |
| 999 | 3 | S | 4-methylphenyl-NH-CH(CH₃)- |
| 1000 | 4 | CH₂ | |
| 1001 | 3 | | |
| 1002 | 4 | | |
| 1003 | 3 | S | 4-nitrophenyl-NH-CH(CH₃)- |
| 1004 | 4 | CH₂ | |
| 1005 | 3 | | |
| 1006 | 4 | | |

TABLE 6-continued

| Example No | n | X | R |
|---|---|---|---|
| 1007 | 3 | S | 4-tert-butylphenyl-NH-CH(CH₃)- |
| 1008 | 4 | CH₂ | |
| 1009 | 3 | | |
| 1010 | 4 | | |
| 1011 | 3 | S | 3,5-dimethylphenyl-NH-CH(CH₃)- |
| 1012 | 4 | CH₂ | |
| 1013 | 3 | | |
| 1014 | 4 | | |
| 1015 | 3 | S | 3,4-dichlorophenyl-NH-CH(CH₃)- |
| 1016 | 4 | CH₂ | |
| 1017 | 3 | | |
| 1018 | 4 | | |
| 1019 | 3 | S | 2,5-dichlorophenyl-NH-CH(CH₃)- |
| 1020 | 4 | CH₂ | |
| 1021 | 3 | | |
| 1022 | 4 | | |
| 1023 | 3 | S | benzo[1,3]dioxol-5-yl-NH-CH(CH₃)- |
| 1024 | 4 | CH₂ | |
| 1025 | 3 | | |
| 1026 | 4 | | |
| 1027 | 3 | S | 4-trifluoromethoxyphenyl-NH-CH(CH₃)- |
| 1028 | 4 | CH₂ | |
| 1029 | 3 | | |
| 1030 | 4 | | |
| 1031 | 3 | S | 3-ethylphenyl-NH-CH(CH₃)- |
| 1032 | 4 | CH₂ | |
| 1033 | 3 | | |
| 1034 | 4 | | |
| 1035 | 3 | S | phenoxy-CH(CH₃)- |
| 1036 | 4 | CH₂ | |
| 1037 | 3 | | |
| 1038 | 4 | | |

TABLE 6-continued
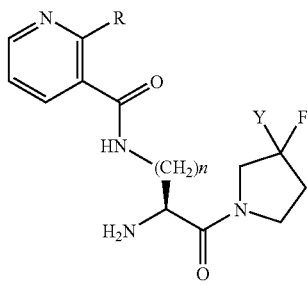
| Example No | n | X | R |
|---|---|---|---|
| 1039 | 3 | S | Me |
| 1040 | 4 | | |
| 1041 | 3 | CH₂ | |
| 1042 | 4 | | |
| 1044 | 3 | S | 4-Cl-C₆H₄-NH- |
| 1045 | 4 | CH₂ | |
| 1046 | 3 | | |
| 1047 | 4 | | |
| 1048 | 3 | S | 2-Cl-C₆H₄-NH- |
| 1049 | 4 | CH₂ | |
| 1050 | 3 | | |
| 1051 | 4 | | |
| 1052 | 3 | S | 3,4-diMe-C₆H₃-NH- |
| 1053 | 4 | CH₂ | |
| 1054 | 3 | | |
| 1055 | 4 | | |
| 1056 | 3 | S | 4-F-C₆H₄-NH- |
| 1057 | 4 | CH₂ | |
| 1058 | 3 | S | 3-NO₂-C₆H₄-NH- |
| 1059 | 4 | CH₂ | |
| 1060 | 3 | | |
| 1061 | 4 | | |
| 1062 | 3 | S | 3-Me-C₆H₄-NH- |
| 1063 | 4 | CH₂ | |
| 1064 | 3 | | |
| 1065 | 4 | | |
| 1066 | 3 | S | 3-MeO-C₆H₄-NH- |
| 1067 | 4 | CH₂ | |
| 1068 | 3 | | |
| 1069 | 4 | | |
TABLE 6-continued
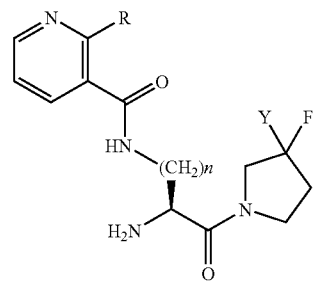
| Example No | n | X | R |
|---|---|---|---|
| 1070 | 3 | S | 3,5-diCl-C₆H₃-NH- |
| 1071 | 4 | CH₂ | |
| 1072 | 3 | | |
| 1073 | 4 | | |
| 1074 | 3 | S | 2,3-diCl-C₆H₃-NH- |
| 1075 | 4 | CH₂ | |
| 1076 | 3 | | |
| 1077 | 4 | | |
| 1078 | 3 | S | 1,2,3,4-tetrahydroquinolin-1-yl |
| 1079 | 4 | CH₂ | |
| 1080 | 3 | | |
| 1081 | 4 | | |
| 1082 | 3 | S | 3-iPr-C₆H₄-NH- |
| 1083 | 4 | CH₂ | |
| 1084 | 3 | | |
| 1085 | 4 | | |
| 1086 | 3 | S | 3-CF₃-C₆H₄-NH- |
| 1087 | 4 | CH₂ | |
| 1088 | 3 | | |
| 1089 | 4 | | |
| 1090 | 3 | S | MeS |
| 1091 | 4 | | |
| 1092 | 3 | CH₂ | |
| 1093 | 4 | | |
| 1094 | 3 | S | MeO |
| 1095 | 4 | | |
| 1096 | 3 | CH₂ | |
| 1097 | 4 | | |

TABLE 7

[Structure: triazine with Cl, R, and NH-CH(CH2NH2 side)-(CH2)n-X-ring where X is in a 5-membered ring with N connected to C(=O)]

| Example No | n | X | R |
|---|---|---|---|
| 1098 | 3 | S | benzo[1,3]dioxol-5-yl-NH-CH< |
| 1099 | 4 | CH2 | |
| 1100 | 3 | | |
| 1101 | 4 | | |
| 1102 | 3 | S | 3,5-dichlorophenyl-NH-CH< |
| 1103 | 4 | CH2 | |
| 1104 | 3 | | |
| 1105 | 4 | | |
| 1106 | 3 | S | 4-fluorophenyl-NH-CH< |
| 1107 | 4 | CH2 | |
| 1108 | 3 | | |
| 1109 | 4 | | |
| 1110 | 3 | S | phenyl-N(CH3)-CH< |
| 1111 | 4 | CH2 | |
| 1112 | 3 | | |
| 1113 | 4 | | |
| 1114 | 3 | S | 3-nitrophenyl-NH-CH< |
| 1115 | 4 | CH2 | |
| 1116 | 3 | | |
| 1117 | 4 | | |
| 1118 | 3 | S | 2,3-dichlorophenyl-NH-CH< |
| 1119 | 4 | CH2 | |
| 1120 | 3 | | |
| 1121 | 4 | | |
| 1122 | 3 | S | benzo[1,3]dioxol-5-yl-N(Et)-CH< |
| 1123 | 4 | CH2 | |
| 1124 | 3 | | |
| 1125 | 4 | | |

TABLE 7-continued

| Example No | n | X | R |
|---|---|---|---|
| 1125a | 3 | S | 4-chloro-2-methoxy-5-methylphenyl-NH-CH< |
| 1126 | 4 | CH2 | |
| 1127 | 3 | | |
| 1128 | 4 | | |
| 1129 | 3 | S | 4-methyl-3-nitrophenyl-NH-CH< |
| 1130 | 4 | CH2 | |
| 1131 | 3 | | |
| 1132 | 4 | | |
| 1133 | 3 | S | 2-methoxyphenyl-NH-CH< |
| 1134 | 4 | CH2 | |
| 1135 | 3 | | |
| 1136 | 4 | | |
| 1137 | 3 | S | 2-methylphenyl-NH-CH< |
| 1138 | 4 | CH2 | |
| 1139 | 3 | | |
| 1140 | 4 | | |
| 1141 | 3 | S | 2,5-dichlorophenyl-NH-CH< |
| 1142 | 4 | CH2 | |
| 1143 | 3 | | |
| 1144 | 4 | | |
| 1145 | 3 | S | 3,4-dichlorophenyl-NH-CH< |
| 1146 | 4 | CH2 | |
| 1147 | 3 | | |
| 1148 | 4 | | |
| 1149 | 3 | S | 4-chlorophenyl-NH-CH< |
| 1150 | 4 | CH2 | |
| 1151 | 3 | | |
| 1152 | 4 | | |
| 1153 | 3 | S | 4-nitrophenyl-NH-CH< |
| 1154 | 4 | CH2 | |
| 1155 | 3 | | |
| 1156 | 4 | | |

TABLE 7-continued
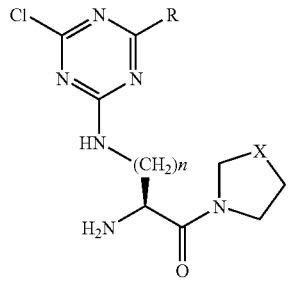
| Example No | n | X | R |
|---|---|---|---|
| 1157 | 3 | S | 3-F-C6H4-NH-CH(CH3)- |
| 1158 | 4 | CH2 | |
| 1159 | 3 | S | 2-Cl-C6H4-NH-CH(CH3)- |
| 1160 | 4 | CH2 | |
| 1161 | 3 | | |
| 1162 | 4 | | |
| 1163 | 3 | S | 2-F-C6H4-NH-CH(CH3)- |
| 1164 | 4 | CH2 | |
| 1165 | 3 | | |
| 1166 | 4 | | |
| 1167 | 3 | S | 2-Cl-4-Me-C6H3-NH-CH(CH3)- |
| 1168 | 4 | CH2 | |
| 1169 | 3 | | |
| 1170 | 4 | | |
| 1171 | 3 | S | 4-Cl-C6H4-N(CH3)-CH(CH3)- |
| 1172 | 4 | CH2 | |
| 1173 | 3 | | |
| 1174 | 4 | | |
| 1175 | 3 | S | 4-MeO-C6H4-NH-CH(CH3)- |
| 1176 | 4 | CH2 | |
| 1177 | 3 | | |
| 1178 | 4 | | |
| 1179 | 3 | S | 4-Me-C6H4-NH-CH(CH3)- |
| 1180 | 4 | CH2 | |
| 1181 | 3 | | |
| 1182 | 4 | | |
| 1183 | 3 | S | C6H5-NH-CH(CH3)- |
| 1184 | 4 | CH2 | |
| 1185 | 3 | | |
| 1186 | 4 | | |
TABLE 8
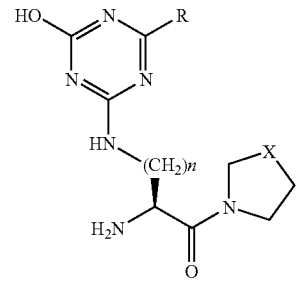
| Example No | n | X | R |
|---|---|---|---|
| 1187 | 3 | S | 1,3-benzodioxol-5-yl-NH-CH(CH3)- |
| 1188 | 4 | CH2 | |
| 1189 | 3 | | |
| 1190 | 4 | | |
| 1191 | 3 | S | 3,5-Cl2-C6H3-NH-CH(CH3)- |
| 1192 | 4 | CH2 | |
| 1193 | 3 | | |
| 1194 | 4 | | |
| 1195 | 3 | S | 4-F-C6H4-NH-CH(CH3)- |
| 1196 | 4 | CH2 | |
| 1197 | 3 | | |
| 1198 | 4 | | |
| 1199 | 3 | S | C6H5-N(CH3)-CH(CH3)- |
| 1200 | 4 | CH2 | |
| 1201 | 3 | | |
| 1202 | 4 | | |
| 1203 | 3 | S | 3-NO2-C6H4-NH-CH(CH3)- |
| 1204 | 4 | CH2 | |
| 1205 | 3 | | |
| 1206 | 4 | | |
| 1207 | 3 | S | 2,3-Cl2-C6H3-NH-CH(CH3)- |
| 1208 | 4 | CH2 | |
| 1209 | 3 | | |
| 1210 | 4 | | |
| 1211 | 3 | S | 1,3-benzodioxol-5-yl-N(Et)-CH(CH3)- |
| 1212 | 4 | CH2 | |
| 1213 | 3 | | |
| 1214 | 4 | | |

TABLE 8-continued
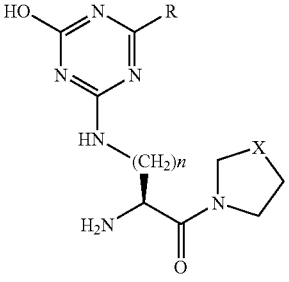
| Example No | n | X | R |
|---|---|---|---|
| 1215 | 3 | S | |
| 1216 | 4 | CH₂ | |
| 1217 | 3 | | |
| 1218 | 4 | | 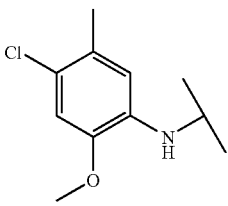 |
| 1219 | 3 | S | |
| 1220 | 4 | CH₂ | |
| 1221 | 3 | | |
| 1222 | 4 | | 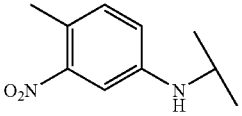 |
| 1223 | 3 | S | |
| 1224 | 4 | CH₂ | |
| 1225 | 3 | | |
| 1226 | 4 | | 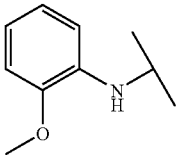 |
| 1227 | 3 | S | |
| 1228 | 4 | CH₂ | |
| 1229 | 3 | | |
| 1230 | 4 | | 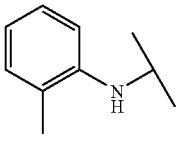 |
| 1231 | 3 | S | |
| 1232 | 3 | CH₂ | |
| 1233 | 4 | | |
| 1235 | | | 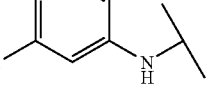 |
| 1235 | 3 | S | |
| 1236 | 4 | CH₂ | |
| 1237 | 3 | | |
| 1238 | 4 | | 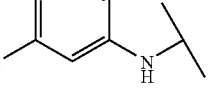 |
| 1239 | 3 | S | |
| 1240 | 4 | CH₂ | |
| 1241 | 3 | | |
| 1242 | 4 | | 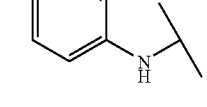 |
| 1243 | 3 | S | |
| 1244 | 4 | CH₂ | |
| 1245 | 3 | | |
| 1246 | 4 | | 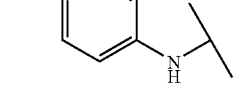 |
TABLE 8-continued
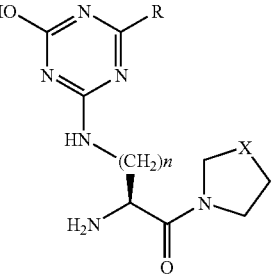
| Example No | n | X | R |
|---|---|---|---|
| 1247 | 3 | S | |
| 1248 | 4 | CH₂ | 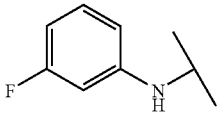 |
| 1249 | 3 | S | |
| 1250 | 4 | CH₂ | |
| 1251 | 3 | | |
| 1252 | 4 | | 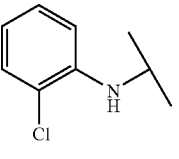 |
| 1253 | 3 | S | |
| 1254 | 4 | CH₂ | |
| 1255 | 3 | | |
| 1256 | 4 | | 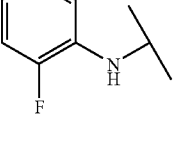 |
| 1257 | 3 | S | |
| 1258 | 4 | CH₂ | |
| 1259 | 3 | | |
| 1260 | 4 | | 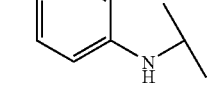 |
| 1261 | 3 | S | |
| 1262 | 4 | CH₂ | |
| 1263 | 3 | | |
| 1264 | 4 | | 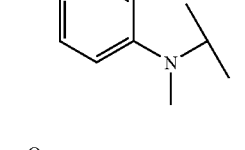 |
| 1265 | 3 | S | |
| 1266 | 4 | CH₂ | |
| 1267 | 3 | | |
| 1268 | 4 | | 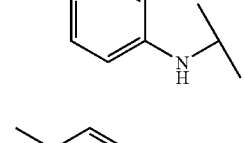 |
| 1269 | 3 | S | |
| 1270 | 4 | CH₂ | |
| 1271 | 3 | | |
| 1272 | 4 | | 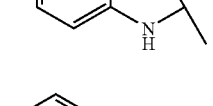 |
| 1273 | 3 | S | |
| 1274 | 4 | CH₂ | |
| 1275 | 3 | | |
| 1276 | 4 | | 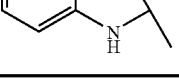 |

Example 1277

1-[2-(S)-Amino-4-(cyclohexylmethylamino)butanoyl]thiomorpholine dihydrochloride

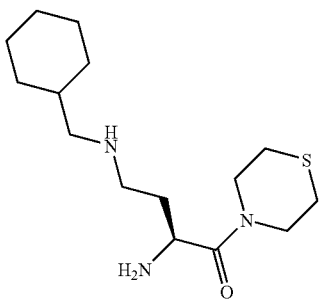

A. 1-[2-(S)-N-(tert-Butyloxycarbonyl)amino-4-(9-fluorenylmethyloxycarbonylamino)-butanoyl]thiomorpholine 1-[2-(S)-N-(tert-Butyloxycarbonyl)amino-4-(9-fluorenylmethyloxycarbonylamino)-butanoic acid (1.0 g, 2.27 mmol) was dissolved in $CH_2Cl_2$/DMF (9:1, 20 mL). To this solution at 0° C. were added 1-hydroxybenzotriazole hydrate (461 mg, 3.41 mmol), water-soluble carbodiimide (521 mg, 2.72 mmol), thiomorpholine (281 mg, 2.72 mmol) and triethylamine (340 mg, 3.4 mmol). After 18 h at 0° C. to room temperature the solvent was removed in vacuo and the residue was taken up in ethyl acetate (100 mL). The solution was washed with 0.3M $KHSO_4$ (2×25 mL), sat. $NaHCO_3$ (2×25 mL), water (2×25 mL) and brine (1×25 mL), dried ($Na_2SO_4$) and evaporated in vacuo. The residue was purified by flash chromatography on silica gel (eluant: 75% ethyl acetate, 25% pet. ether) to give a white solid identified as 1-(2-(S)-N-(tert-butyloxycarbonyl)amino-4-(9-fluorenylmethyloxycarbonylamino)-butanoyl]thiomorpholine (516 mg, 0.98 mmol, 43%).

B. 1-[2-(S)-N-(tert-Butyloxycarbonyl)-4-amino)-butanoyl]thiomorpholine

1-[2-(S)-N-(tert-Butyloxycarbonyl)amino-4-(9-fluorenylmethyloxycarbonylamino)-butanoyl thiomorpholine (500 mg, 0.95 mmol) was dissolved in tetrahydrofuran (20 mL). Diethylamine (5 mL) was added. After 90 min at room temperature the solvent was removed in vacuo and the residue was purified by flash chromatography on silica gel (eluant: 90% chloroform, 7% methanol, 3% triethylamine) to give a pale yellow oil identified as 1-[2-(S)-N-(tert-butyloxycarbonyl)-4-amino)-butanoyl]thiomorpholine (162 mg, 0.54 mmol, 56%).

C. 1-[2-(S)-N-(tert-Butyloxycarbonyl)-amino-4-(cyclohexylmethylamino)butanoyl]thiomorpholine 1-[2-(S)-N-(tert-Butyloxycarbonyl)-4amino)-butanoyl]thiomorpholine (41 mg, 0.135 mmol) was dissolved in dichloroethane (10 mL). To this solution was added cyclohexanecarboxaldehyde (15 mg, 0.135 mmol). After 30 mins sodium triacetoxyborohydride (32 mg, 0.15 mmol) was added. After 18 h at room temperature the solvent was removed in vacuo and the residue was taken up in chloroform (70 mL). This solution was washed with water (2×20 mL) and brine (1×20 mL), dried ($Na_2SO_4$) and evaporated in vacuo to give a yellow oil. The residue was purified by flash chromatography on silica gel (eluant: 1% acetic acid, 9% methanol, 90% chloroform) to give a colourless oil identified as 1-[2-(S)-N-(tert-butyloxycarbonyl)-amino-4-(cyclohexylmethylamino)butanoyl]thiomorpholine (25 mg, 0.063 mmol, 47%).

D. 1-[2-(S)-Amino-4-(cyclohexylmethylamino)butanoyl]thiomorpholine dihydrochloride 1-[2-(S)-N-(tert-Butyloxycarbonyl)-amino-4-(cyclohexylmethylamino)butanoyl]thiomorpholine (25 mg, 0.063 mmol) was dissolved in 4M HCl/dioxan (20 mL). After 1 h at room temperature the solvent was removed in vacuo. The residue was lyophilised from water to give a white solid identified as 1-[2-(S)-amino-4-(cyclohexylmethylamino)butanoyl]thiomorpholine dihydrochloride (23 mg, 0.063 mmol, 100%).

$[M+H]^+=300.3$

Example 1278

1-[2-(S)-Amino-4-((quinolin-2-ylmethyl)amino)butanoyl]thiomorpholine dihydrochloride

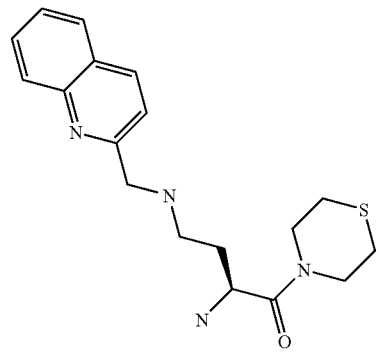

A. 1-[2-(S)-N-(tert-Butyloxycarbonyl)-amino-4-((quinolin-2-ylmethyl)amino)butanoyl thiomorpholine 1-[2-(S)-N-(tert-Butyloxycarbonyl)-4-amino)-butanoyl] thiomorpholine (41 mg, 0.135 mmol) was dissolved in 1,2-dichloroethane (10 mL). To this solution was added 2-quinolinecarboxaldehyde (32 mg, 0.15 mmol). After 30 mins sodium triacetoxyborohydride (36 mg, 0.17 mmol) was added. After 18 h at room temperature the solvent was removed in vacuo and the residue was taken up in chloroform (70 mL). This solution was washed with water (2×20 mL) and brine (1×20 mL), dried ($Na_2SO_4$) and evaporated in vacuo to give a yellow oil. The residue was purified by flash chromatography on silica gel (eluant: 1% acetic acid, 9% methanol, 90% chloroform) to give a colourless oil identified as 1-[2-(S)-N-(tert-butyloxycarbonyl)-amino-4-((quinolin-2-ylmethyl)amino)butanoyl thiomorpholine (32 mg, 0.072 mmol, 53%).

B. 1-[2-(S)-Amino-4-((quinolin-2-ylmethyl)amino)butanoyl]thiomorpholine dihydrochloride 1-[2-(S)-N-(tert-Butyloxycarbonyl)-amino-4-((quinolin-2-ylmethyl)amino)butanoyl]thiomorpholine (12 mg, 0.027 mmol) was dissolved in 4M HCl/dioxan (20 mL). After 4 h at room temperature the solvent was removed in vacuo. The residue was lyophilised from water to give a white solid identified as 1-[2-(S)-amino-4-((quinolin-2-ylmethyl)amino)butanoyl]thiomorpholine dihydrochloride (11.3 mg, 0.027 mmol, 100%).

[M+H]$^+$=345.3

Example 1279

1-[2-(S)-Amino-4-(cyclohexylmethylamino)butanoyl]piperidine dihydrochloride

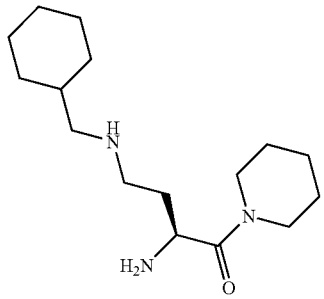

A. 1-[2-(S)-N-(tert-Butyloxycarbonyl)amino-4-(9-fluorenylmethyloxycarbonylamino)-butanoyl]piperidine 1-[2-(S)-N-(tert-Butyloxycarbonyl)amino-4-(9-fluorenylmethyloxycarbonylamino)-butanoic acid (947 mg, 2.154 mmol) was dissolved in CH$_2$Cl$_2$/DMF (9:1, 20 mL). To this solution at 0° C. were added 1-hydroxybenzotriazole hydrate (436 mg, 3.2 mmol), water-soluble carbodiimide (495 g, 2.58 mmol), piperidine (220 g, 2.58 mmol) and triethylamine (320 mg, 3.2 mmol). After 18 h at 0° C. to room temperature the solvent was removed in vacuo and the residue was taken up in ethyl acetate (100 mL). The solution was washed with 0.3M KHSO$_4$ (2×25 mL), sat. NaHCO$_3$ (2×25 mL), water (2×25 mL) and brine (1×25 mL), dried (Na$_2$SO$_4$) and evaporated in vacuo. The residue was purified by flash chromatography on silica gel (eluant: 75% ethyl acetate, 25% pet. ether) to give a white solid identified as 1-[2-(S)-N-(tert-butyloxycarbonyl)amino-4-(9-fluorenylmethyloxycarbonylamino)-butanoyl]piperidine (556 mg, 1.1 mmol, 51%).

B. 1-[2-(S)-N-(tert-Butyloxycarbonyl)-4-amino)-butanoyl]piperidine

1-[2-(S)-N-(tert-Butyloxycarbonyl)amino-4-(9-fluorenylmethyloxycarbonylamino)-butanoyl]piperidine (540 g, 1.1 mmol) was dissolved in tetrahydrofuran (20 mL). Diethylamine (5 mL) was added. After 90 min at room temperature the solvent was removed in vacuo and the residue was purified by flash chromatography on silica gel (eluant: 90% chloroform, 7% methanol, 3% triethylamine) to give a pale yellow oil identified as 1-[2-(S)-N-(tert-butyloxycarbonyl)-4-amino)-butanoyl]piperidine (171 mg, 0.6 mmol, 57%).

C. 1-[2-(S)-N-(tert-Butyloxycarbonyl)-amino-4-(cyclohexylmethylamino)butanoyl]piperidine 1-[2-(S)-N-(tert-Butyloxycarbonyl)-4-amino)-butanoyl]piperidine (43 mg, 0.15 mmol) was dissolved in 1,2-dichloroethane (20 mL). To this solution was added cyclohexanecarboxaldehyde (17 mg, 0.15 mmol). After 30 mins sodium triacetoxyborohydride (36 mg, 0.17 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 1% acetic acid, 9% methanol, 90% chloroform) to give a colourless oil identified as 1-[2-(S)-N-(tert-butyloxycarbonyl)-amino-4-(cyclohexylmethylamino)butanoyl]piperidine (38 mg, 0.1 mmol, 66%).

D. 1-[2-(S)-Amino-4-(cyclohexylmethylamino)butanoyl]piperidine dihydrochloride 1-[2-(S)-N-(tert-Butyloxycarbonyl)-amino-4-(cyclohexylmethylamino)butanoyl]piperidine (38 mg, 0.1 mmol) was dissolved in 4M HCl/dioxan (2 mL). After 1 h at room temperature the solvent was removed in vacuo. The residue was lyophilised from water to give a white solid identified as 1-[2-(S)-amino-4-(cyclohexylmethylamino)butanoyl]piperidine dihydrochloride (33 mg, 0.093 mmol, 93%).

[M+H]$^+$=282.3

Example 1280

1-[2-(S)-Amino-4-((quinolin-2-ylmethyl)amino)butanoyl]piperidine dihydrochloride

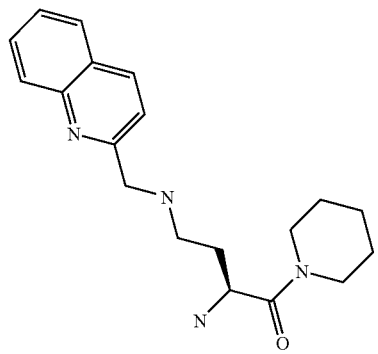

A. 1-[2-(S)-N-(tert-Butyloxycarbonyl)-amino-4-((quinolin-2-ylmethyl)amino)butanoyl]piperidine 1-[2-(S)-N-(tert-Butyloxycarbonyl)-4-amino)-butanoyl]piperidine (24 mg, 0.15 mmol) was dissolved in 1,2-dichloroethane (25 mL). To this solution was added 2-quinolinecarboxaldehyde (24 mg, 0.15 mmol). After 30 mins sodium triacetoxyborohydride (36 mg, 0.17 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 1% acetic acid, 9% methanol, 90% chloroform) to give a colourless oil identified as 1-[2-(S)-N-(tert-butyloxycarbonyl)-amino-4-((quinolin-2-ylmethyl)amino)butanoyl]piperidine (35 mg, 0.082 mmol, 55%).

B. 1-[2-(S)-Amino-4-((quinolin-2-ylmethyl)amino)butanoyl]piperidine dihydrochloride 1-[2-(S)-N-(tert-Butyloxycarbonyl)-amino-4-((quinolin-2-ylmethyl)amino)butanoyl]piperidine (35 mg, 0.082 mmol) was dissolved in 4M HCl/dioxan (2 mL). After 1 h at room temperature the solvent was removed in vacuo. The residue was lyophilised from water to give a white solid identified as 1-[2-(S)-amino-4-((quinolin-2-ylmethyl)amino)butanoyl]piperidine dihydrochloride (26 mg, 0.065 mmol, 79%).

[M+H]$^+$=327.3

Example 1281

3-Fluoro-1-[2-(S)-amino-4-(cyclohexenylmethylamino)butanoyl]pyrrolidine dihydrochloride

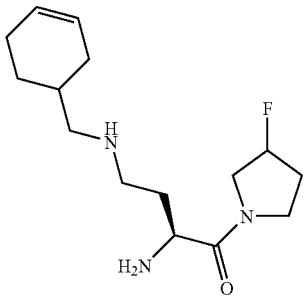

A. 1-(tert-Butyloxycarbonyl)-3-fluoropyrrolidine

N-(tert-Butyloxycarbonyl)-3-hydroxypyrrolidine (21.0 g, 10.7 mmol) was dissolved in CH$_2$Cl$_2$ (30 ml). (Diethylamino)sulphur trifluoride (1.72 g, 10.7 mmol) was added to this solution at −78° C. The mixture was stirred for 18 hours at −78° C. to room temperature then the reaction mixture was carefully poured into sat. NaHCO$_3$ (100 ml) and stirred for 15 min and extracted with CH$_2$Cl$_2$. The organic extract was washed with water and brine, dried (Na$_2$SO$_4$) and evaporated in vacuo to give an orange oil. The residue was purified by flash chromatography (eluant: 28% ethyl acetate, 72% pet. ether 60-80) to give a colourless oil identified as 1-(tert-butyloxycarbonyl)-3-fluoropyrrolidine (1.14 g, 5.34 mmol, 50%).

B. 3-Fluoropyrrolidine hydrochloride 1-(tert-Butyloxycarbonyl)-3-fluoropyrrolidine (1.14 g, 5.34 mmol) was dissolved in 4M HCl/dioxan (30 ml). The mixture was stirred for 1 hour at room temperature then the solvent was removed in vacuo to give an off-white solid identified as 3-fluoropyrrolidine hydrochloride (640 mg, 5.2 mmol, 95%).

C. 3-Fluoro-1-[2-(S)-N-(tert-butyloxycarbonyl)amino-4-(9-fluorenylmethyloxycarbonylamino)-butanoyl]pyrrolidine 1-[2-(S)-N-(tert-Butyloxycarbonyl)amino-4-(9-fluorenylmethyloxycarbonylamino)-butanoic acid (950 mg, 2.15 mmol) was dissolved in CH$_2$Cl$_2$/DMF (9:1, 20 mL). To this solution at 0° C. were added 1-hydroxybenzotriazole hydrate (395 mg, 2.6 mmol), water-soluble carbodiimide (572 mg, 3.0 mmol), 3-fluoropyrrolidine hydrochloride (270 g, 2.15 mmol) and triethylamine (320 mg, 3.2 mmol). After 18 h at 0° C. to room temperature the solvent was removed in vacuo and the residue was taken up in ethyl acetate (100 mL). The solution was washed with 0.3M KHSO$_4$ (2×25 mL), sat. NaHCO$_3$ (2×25 mL), water (2×25 mL) and brine (1×25 mL), dried (Na$_2$SO$_4$) and evaporated in vacuo. The residue was purified by flash chromatography on silica gel (eluant: 75% ethyl acetate, 25% pet. ether) to give a white solid identified as 3-fluoro1-[2-(S)-N-(tert -butyloxycarbonyl)amino-4-(9-fluorenylmethyloxycarbonylamino)-butanoyl]pyrrolidine (808 mg, 1.58 mmol, 73%).

D. 3-Fluoro-1-[2-(S)-N-(tert-butyloxycarbonyl)-4-amino)-butanoyl]pyrrolidine 3-Fluoro-1-[2-(S)-N-(tert-butyloxycarbonyl)amino-4-(9-fluorenylmethyloxycarbonylamino)-butanoyl]pyrrolidine (800 mg, 1.58 mmol) was dissolved in tetrahydrofuran (20 mL). Diethylamine (5 mL) was added. After 90 min at room temperature the solvent was removed in vacuo and the residue was purified by flash chromatography on silica gel (eluant: 90% chloroform, 7% methanol, 3% triethylamine) to give a pale yellow oil identified as 3-fluoro-1-[2-(S)-N-(tert-butyloxycarbonyl)-4-amino)-butanoyl]pyrrolidine (316 mg, 1.04 mmol, 66%).

E. 3-Fluoro-1-[2-(S)-N-(tert-butyloxycarbonyl)-amino-4-(cyclohexenylmethylamino)butanoyl]pyrrolidine 3-Fluoro-1-(2-(S)-N-(tert-butyloxycarbonyl)-4-amino)-butanoyl]pyrrolidine (150 mg, 0.52 mmol) was dissolved in methanol (20 mL). To this solution was added 3-cyclohexenecarboxaldehyde (63 mg, 0.57 mmol). After 30 mins sodium triacetoxyborohydride (220 mg, 1.04 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 1% acetic acid, 9% methanol, 90% chloroform) to give a colourless oil identified as 3-fluoro-1-[2-(S)-N-(tert-butyloxycarbonyl)-amino-4-(cyclohexenylmethylamino)butanoyl]pyrrolidine (176 mg, 0.46 mmol, 77%).

F. 3-Fluoro-1-[2-(S)-amino-4-(cyclohexenylmethylamino)butanoyl]pyrrolidine dihydrochloride 3-Fluoro-1-[2-(S)-N-(tert-butyloxycarbonyl)-amino-4-(cyclohexenylmethylamino)butanoyl]pyrrolidine (176 mg, 0.46 mmol) was dissolved in 4M HCl/dioxan (2 mL). After 1 h at room temperature the solvent was removed in vacuo. The residue was lyophilised from water to give a white solid identified as 3-fluoro-1-[2-(S)-amino-4-(cyclohexenylmethylamino)butanoyl]pyrrolidine dihydrochloride (140 mg, 0.39 mmol, 963%).

[M+H]$^+$=284.3

Example 1282

1-[2-(S)-Amino-4-(N-methyl-N-(2-methylbenzyl)amino)butanoyl]piperidine dihydrochloride

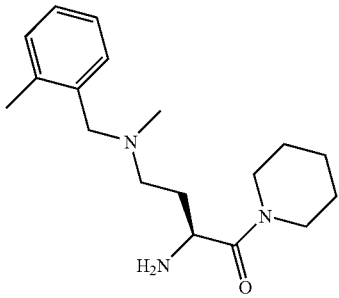

A. N-(tert-Butyloxycarbonyl)-L-homoserine lactone

L-Homoserine lactone 1.76 g, 12.8 mmol) was dissolved in DMF (30 mL). This solution was cooled to 0° C., triethylamine (1.41, 14.1 mmol) di-tert-butyl dicarbonate (3.35 g, 15.35 mmol) was added. After 18 hours at room temperature the solvent was evaporated in vacuo, the residue was taken up in dichloromethane (200 mL). This solution was washed with 1M KHSO$_4$ (2×50 mL) and brine (1×50 mL), dried (Na$_2$SO$_4$) and evaporated in vacuo to give a white solid, recrystallised from EtOAc/pet.ether to give a white solid identified as N-(tert-butyloxycarbonyl)-L-homoserine lactone (2.25 mg, 11.2 mmol, 87%).

B. 1-[2-(S)-(N-(tert-Butyloxycarbonyl)amino)-4-hydroxybutanoyl]piperidine

N-(tert-Butyloxycarbonyl)-L-homoserine lactone (100 mg, 0.5 mmol) was dissolved in tetrahydrofuran (30 mL). Piperidine (42 mg, 0.5 mmol) was added. After 72 hours at room temperature the reaction mixture was diluted with ethyl acetate (150 mL). This solution was washed with water (1×20 mL) and brine (1×20 mL), dried (Na$_2$SO$_4$) and evaporated in vacuo to give a yellow oil identified as 1-[2-(S)-(N-(tert-butyloxycarbonyl)amino)-4-hydroxybutanoyl]piperidine (142 mg, 0.5 mmol, 100%).

C. 1-[2-(S)-(N-(tert-Butyloxycarbonyl)amino)-4-oxobutanoyl]piperidine

1-[2-(S)-(N-(tert-Butyloxycarbonyl)amino)-4-hydroxybutanoyl]piperidine (142 mg, 0.5 mmol) was dissolved in dichloromethane (50 mL). Dess-Martin periodinane (232 mg, 0.5 mmol) was added. After 1 hour at room temperature the reaction mixture was diluted with ethyl acetate (150 mL). This solution was washed with water (1×20 ml) and brine (1×20 ml), dried (Na$_2$SO$_4$) and evaporated in vacuo to give a colourless oil. Purified by flash chromatography on silica gel (eluant: 50% ethyl acetate, 50% pet. ether 60-80) to give a colourless oil identified as 1-[2-(S)-(N-(tert-butyloxycarbonyl)amino)-4-oxobutanoyl]piperidine (40 mg, 0.14 mmol, 27%).

D. 1-[2-(S)-(N-(tert-butyloxycarbonyl)amino-4-(N-methyl-N-(2-methylbenzyl)amino)butanoyl]piperidine 1-[2-(S)-(N-(tert-Butyloxycarbonyl)amino)-4-oxobutanoyl]piperidine (40 mg, 14 mmol) was dissolved in methanol (20 mL). To this solution was added N-methyl-2-methylbenzylamine (19 mg, 0.14 mmol). After 2 hours sodium triacetoxyborohydride (64 mg, 0.3 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel to give a colourless oil identified as 1-[2-(S)-(N-(tert-butyloxycarbonyl)amino-4-(N-methyl-N-(2-methylbenzyl)amino)butanoyl]piperidine (36 mg, 0.09 mmol, 64%).

E. 1-[2-(S)-Amino-4-(N-methyl-N-(2-methylbenzyl)amino)butanoyl]piperidine dihydrochloride 1-[2-(S)-(N-(tert-Butyloxycarbonyl)amino-4-(N-methyl-N-(2-methylbenzyl)amino)butanoyl]piperidine (36 mg, 0.09 mmol) was dissolved in 4M HCl/dioxan (20 mL). After 1 h at room temperature the solvent was removed in vacuo. The residue was lyophilised from water to give a pale brown solid identified as 1-[2-(S)-amino-4-(N-methyl-N-(2-methylbenzyl)amino)butanoyl]piperidine dihydrochloride (43 mg, 0.09 mmol, 100%)

Example 1283

1-[N-(2"-(Cyclohexylmethylaminoethyl)glycinyl)]thiomorpholine dihydrochloride

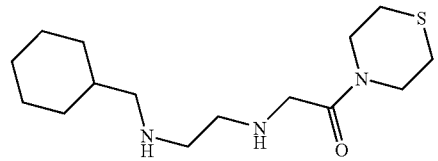

A. 1-[N-2'-(tert-Butyloxycarbonyl)-N-(2"-(9-fluorenylmethyloxycarbonyl aminoethyl)-glycinyl]thiomorpholine N-2'-(tert-Butyloxycarbonyl)-N-(2"-(9-fluorenylmethyloxycarbonyl aminoethyl)-glycine (2.5 g, 5.7 mmol) was dissolved in CH$_2$Cl$_2$/DMF (9:1, 100 mL). To this solution at 0° C. were added 1-hydroxybenzotriazole hydrate (833 mg, 6.3 mmol), water-soluble carbodilmide (974 mg, 6.3 mmol), thiomorpholine (617 mg, 6.0 mmol) and N-methylmorpholine (800 mg, 8 mmol). After 18 h at 0° C. to room temperature the solvent was removed in vacuo and the residue was taken up in ethyl acetate (100 mL). The solution was washed with 0.3M KHSO$_4$ (2×25 mL), sat. NaHCO$_3$ (2×25 mL), water (2×25 mL) and brine (1×25 mL), dried (Na$_2$SO$_4$) and evaporated in vacuo. The residue was purified by flash chromatography on silica gel (eluant: 75% ethyl acetate, 25% pet. ether) to give a white solid identified as 1-[N-2'-(tert-butyloxycarbonyl)-N-(2"-(9-fluorenylmethyloxycarbonyl aminoethyl)-glycinyl]thiomorpholine (2.7 g, 5.1 mmol, 90%).

B. 1-[N-2'-(tert-Butyloxycarbonyl)-(2"-aminoethyl)-glycinyl]thiomorpholine

1-[N-2'-(tert-Butyloxycarbonyl)-N-(2"-(9-fluorenylmethyloxycarbonyl aminoethyl)-glycinyl]thiomorpholine (2.7 g, 5.1 mmol) was dissolved in tetrahydrofuran (20 mL). Diethylamine (5 mL) was added. After 90 min at room temperature the solvent was removed in vacuo and the residue was purified by flash chromatography on silica gel (eluant: 90% chloroform, 7% methanol, 3% triethylamine) to give a pale yellow oil identified as 1-[N-2'-(tert-butyloxycarbonyl)-(2"-aminoethyl)-glycinyl]thiomorpholine (1.44 g, 4.7 mmol, 92%).

C. 1-[2'-N-(tert-Butyloxycarbonyl N-(2"-(cyclohexylmethylaminoethyl)-glycinyl]thiomorpholine 1-[N-2'-(tert-Butyloxycarbonyl)-(2"-aminoethyl)-glycinyl]thiomorpholine (100 mg, 0.3 mmol) was dissolved in methanol (25 mL). To this solution was added cyclohexanecarboxaldehyde (34 mg, 0.3 mmol). After 30 mins sodium triacetoxyborohydride (126 mg, 0.6 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 1% acetic acid, 9% methanol, 90% chloroform) to give a colourless oil identified as 1-[2'-N-(tert-Butyloxycarbonyl N-(2"-(cyclohexylmethylaminoethyl)-glycinyl]thiomorpholine (33 mg, 0.08 mmol, 27%).

D. 1-[N-(2"-(Cyclohexylmethylaminoethyl)glycinyl)]thiomorpholine dihydrochloride 1-[2'-N-(tert-Butyloxycarbonyl-N-(2"-(cyclohexylmethylaminoethyl)-glycinyl]thiomorpholine (33 mg, 0.081 mmol) was dissolved in 4M HCl/dioxan (20 mL). After 1 h at room temperature the solvent was removed in vacuo. The residue was lyophilised from water to give a white solid identified as 1-[N-(2"-(cyclohexylmethylaminoethyl)glycinyl)]thiomorpholine dihydrochloride (31 mg, 0.08 mmol, 100%).
[M+H]$^+$=300.3

Example 1284

1-[N-(2"-((Quinolin-2-ylmethyl)aminoethyl)glycinyl)]pyrrolidine dihydrochloride

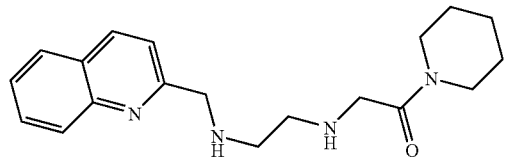

A. 1-[N-2'-(tert-Butyloxycarbonyl)-N-(2"-(9-fluorenylmethyloxycarbonyl aminoethyl)-glycinyl]piperidine N-2'-(tert-Butyloxycarbonyl)-N-(2"-(9-fluorenylmethyloxycarbonyl aminoethyl)-glycine (2.5 g, 5.7 mmol) was dissolved in CH$_2$Cl$_2$/DMF (9:1, 100 mL). To this solution at 0° C. were added 1-hydroxybenzotriazole hydrate (1.5 g, 11.1 mmol), water-soluble carbodiimide (1.3 g, 6.8 mmol), piperidine (484 mg, 5.69 mmol) and N-methylmorpholine (800 mg, 8 mmol). After 18 h at 0° C. to room temperature the solvent was removed in vacuo and the residue was taken up in ethyl acetate (100 mL). The solution was washed with 0.3M KHSO$_4$ (2×25 mL), sat. NaHCO$_3$ (2×25 mL), water (2×25 mL) and brine (1×25 mL), dried (Na$_2$SO$_4$) and evaporated in vacuo. The residue was purified by flash chromatography on silica gel (eluant: 75% ethyl acetate, 25% pet. ether) to give a white solid identified as 1-[N-2'-(tert-butyloxycarbonyl)-N-(2"-(9-fluorenylmethyloxycarbonyl aminoethyl)-glycinyl]piperidine (2.8 g, 5.5 mmol, 96%).

B. 1-[N-2'-(tert-Butyloxycarbonyl)-(2"-aminoethyl)-glycinyl]piperidine

1-[N-2'-(tert-Butyloxycarbonyl)-N-(2"-(9-fluorenylmethyloxycarbonyl aminoethyl)-glycinyl]piperidine (2.8 g, 5.5 mmol) was dissolved in tetrahydrofuran (20 mL). Diethylamine (5 mL) was added. After 90 min at room temperature the solvent was removed in vacuo and the residue was purified by flash chromatography on silica gel (eluant: 90% chloroform, 7% methanol, 3% triethylamine) to give a pale yellow oil identified as 1-[N-2'-(tert-butyloxycarbonyl)-(2"-aminoethyl)-glycinyl]piperidine (1.4 g, 4.9 mmol, 89%).

C. 1-[2'-N-(tert-Butyloxycarbonyl N-(2"-((quinolin-2-ylmethyl)aminoethyl)-glycinyl]piperidine 1-[N-2'-(tert-Butyloxycarbonyl)-(2"-aminoethyl)-glycinyl]piperidine was dissolved in methanol (25 mL). To this solution was added 2-quinolinecarboxaldehyde. After 30 mins sodium triacetoxyborohydride was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 1% acetic acid, 9% methanol, 90% chloroform) to give a colourless oil identified as 1-[2'-N-(tert-butyloxycarbonyl N-(2"-((quinolin-2-ylmethyl)aminoethyl)-glycinyl]piperidine.

D. 1-[N-(2"-((Quinolin-2-ylmethyl)aminoethyl)glycinyl)]piperidine dihydrochloride 1-2'-N-(tert-Butyloxycarbonyl-N-(2"-((quinolin-2-ylmethyl)aminoethyl)-glycinyl]piperidine was dissolved in 4M HCl/dioxan (20 mL). After 1 h at room temperature the solvent was removed in vacuo. The residue was lyophilised from water to give a white solid identified as 1-[N-(2"-((quinolin-2-ylmethyl)aminoethyl)glycinyl)]piperidine dihydrochloride.

Example 1285

1-[N,N-(2",2"-((Dicinnamyl)aminoethyl)glycinyl)]thiomorpholine dihydrochloride

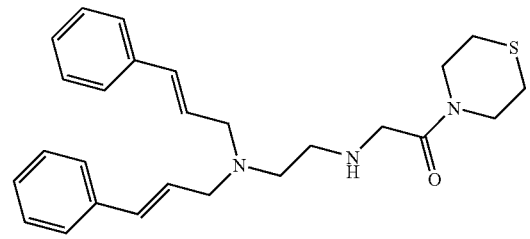

A. 1-[2'-N-(tert-Butyloxycarbonyl N,N-(2",2"-((dicinnamyl)aminoethyl)-glycinyl]thiomorpholine (2S)-1-(N$^\alpha$-(tert-Butyloxycarbonyl)-L-lysinyl)-pyrrolidine-2-carbonitrile (250 mg, 0.83 mmol) was dissolved in dichloroethane (25 mL). To this solution was added trans-cinnamaldehyde (108 mg, 0.83 mmol). After 30 mins sodium triacetoxyborohydride (350 mg, 1.6 mmol) was added. After 18 h at room temperature the solvent was removed in vacuo and the residue was taken up in chloroform (70 mL). This solution was washed with water (2×20 mL) and brine (1×20 mL), dried (Na$_2$SO$_4$) and evaporated in vacuo to give a yellow oil. The residue was purified by flash chromatography on silica gel (eluant: 2% methanol, 98% chloroform) to give a colourless oil identified as 1-[2'-N-(tert-butyloxycarbonyl N,N-(2",2"-((dicinnamyl)aminoethyl)-glycinyl]thiomorpholine. Further elution with 9% methanol, 90% chloroform and 1% acetic acid gave a colourless oil identified as 1-[2'-N-(tert-butyloxycarbonyl N,-(2"-((cinnamyl)aminoethyl)glycinyl]thiomorpholine (180 mg, 0.43 mmol, 52%)

B. 1-[N,N-(2",2"-((Dicinnamyl)aminoethyl)glycinyl)]thiomorpholine dihydrochloride 1-[2'-N-(tert-Butyloxycarbonyl N,N-(2",2"-((dicinnamyl) aminoethyl)-glycinyl]thiomorpholine was dissolved in 4M HCl/dioxan (20 mL). After 1 h at room temperature the solvent was removed in vacuo. The residue was lyophilised from water to give a white solid identified as 1-[N,N-(2", 2"-((dicinnamyl)aminoethyl)glycinyl)]thiomorpholine dihydrochloride.

Example 1286

1-[N-(2"-((Cinnamyl)aminoethyl)glycinyl)]thiomorpholine dihydrochloride

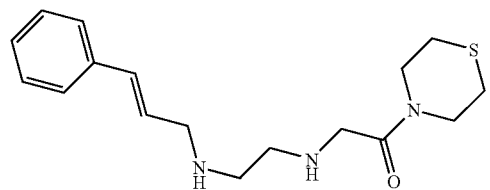

A. 1-[N-(2"-((Cinnamyl)aminoethyl)glycinyl)]thiomorpholine dihydrochloride

1-[2'-N-(tert-Butyloxycarbonyl N-(2"-((cinnamyl)aminoethyl)-glycinyl]thiomorpholine (180 mg, 0.43 mmol) was dissolved in 4M HCl/dioxan (20 mL). After 1 h at room temperature the solvent was removed in vacuo. The residue was lyophilised from water to give a white solid identified as 1-[N-(2"-((cinnamyl)aminoethyl)glycinyl)]thiomorpholine dihydrochloride (168 mg, 0.43 mmol, 100%).

[M+H]$^+$=320.3

Example 1287

3,3-Difluoro-1-[N-2"-(3'-trifluoromethylanilino)pyridyl-3-carbonyl aminoethyl)glycinyl)]pyrrolidine dihydrochloride

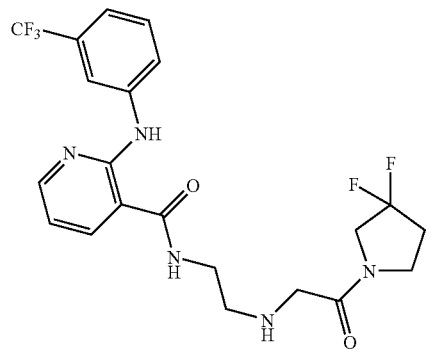

A. 3,3-Difluoro-1-[N-2'-(tert-butyloxycarbonyl)-N-(2"-(9-fluorenylmethyloxycarbonyl aminoethyl)-glycinyl]pyrrolidine N-2'-(tert-Butyloxycarbonyl)-N-(2"-(9-fluorenylmethyloxycarbonyl aminoethyl)-glycine (1.0 g, 2.27 mmol) was dissolved in CH$_2$Cl$_2$/DMF (9:1, 100 mL). To this solution at 0° C. were added 1-hydroxybenzotriazole hydrate (620 mg, 4.6 mmol), water-soluble carbodiimide (560 mg, 2.8 mmol), 3,3-difluoropyrrolidine hydrochloride (360 mg, 2.5 mmol) and N-methylmorpholine (800 mg, 8 mmol). After 18 h at 0° C. to room temperature the solvent was removed in vacuo and the residue was taken up in ethyl acetate (100 mL). The solution was washed with 0.3M KHSO$_4$ (2×25 mL), sat. NaHCO$_3$ (2×25 mL), water (2×25 mL) and brine (1×25 mL), dried (Na$_2$SO$_4$) and evaporated in vacuo. The residue was purified by flash chromatography on silica gel (eluant: 60% ethyl acetate, 40% pet. ether) to give a white solid identified as 3,3-difluoro-1-[N-2'-(tert-butyloxycarbonyl)-N-(2"-(9-fluorenylmethyloxycarbonyl aminoethyl)-glycinyl]pyrrolidine (934 g, 1.7 mmol, 77%).

B. 3,3-Difluoro-1-[N-2'-(tert-butyloxycarbonyl)aminoethyl)-glycinyl]pyrrolidine 3,3-Difluoro-1-[N-2'-(tert-butyloxycarbonyl)-N-(2"-(9-fluorenylmethyloxycarbonyl aminoethyl)-glycinyl]pyrrolidine (890 g, 1.68 mmol) was dissolved in tetrahydrofuran (20 mL). Diethylamine (5 mL) was added. After 90 min at room temperature the solvent was removed in vacuo and the residue was purified by flash chromatography on silica gel (eluant: 90% chloroform, 7% methanol, 3% triethylamine) to give a pale yellow oil identified as 3,3-difluoro-1-[N-2'-(tert-butyloxycarbonyl)aminoethyl)-glycinyl]pyrrolidine (470 mg, 1.5 mmol, 91%).

C. 3,3-Difluoro-1-N-2'-(tert-butyloxycarbonyl)-N-2"-(3'-trifluoromethylanilino)pyridyl-3-carbonyl aminoethyl)glycinyl)]pyrrolidine 3,3-Difluoro-1-[N-2'-(tert-butyloxycarbonyl)aminoethyl)-glycinyl]pyrrolidine (50 mg, 0.16 mmol) was dissolved in CH$_2$Cl$_2$/DMF (9:1, 20 mL). To this solution at 0° C. was added 1-hydroxybenzotriazole hydrate (46 mg, 0.34 mmol), water-soluble carbodiimide (40 mg, 0.2 mmol), niflumic acid (49 mg, 0.17 mmol) and N-methylmorpholine (40 mg, 0.4 mmol). After 18 h at 0° C. to room temperature the solvent was removed in vacuo and the residue was taken up in ethyl acetate (70 mL). The solution was washed with 0.3M $KHSO_4$ (1×20 mL), sat. $NaHCO_3$ (1×20 mL), water (1×20 mL) and brine (1×20 mL), dried ($Na_2SO_4$) and evaporated in vacuo. The residue was purified by flash chromatography on silica gel (eluant: 75% ethyl acetate, 25% pet. ether) to give a yellow oil identified as 3,3-difluoro-1-[N-2'-(tert-butyloxycarbonyl)-N-2"-(3'-trifluoromethylanilino)pyridyl-3-carbonyl aminoethyl)glycinyl)]pyrrolidine (63 mg, 0.11 mmol, 67%).

D. 3,3-Difluoro-1-[N-2"-(3'-trifluoromethylanilino)pyridyl-3-carbonyl aminoethyl) glycinyl)]pyrrolidine dihydrochloride 3,3-Difluoro-1-[N-2'-(tert-butyloxycarbonyl)-N-2"-(3'-trifluoromethylanilino)pyridyl-3-carbonyl aminoethyl)glycinyl)]pyrrolidine (55 mg, 0.10 mmol) was dissolved in 4M HCl/dioxan (20 mL). After 1 h at room temperature the solvent was removed in vacuo. The residue was lyophilised from water to give a pale brown solid identified as 3,3-difluoro-1-[N-2"-(3'-trifluoromethylanilino)pyridyl-3-carbonyl aminoethyl)glycinyl)]pyrrolidine dihydrochloride (52 mg, 0.10 mmol, 100%).
$[M+H]^+=472.3$

Example 1288

3,3-Difluoro-[N-2"-(6-Chloro-4-(4'-fluoroanilino)-1,3,5-triazinyl)aminoethyl) glycinyl)]thiomorpholine dihydrochloride

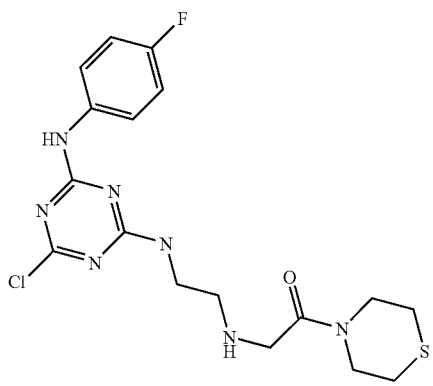

A. 4,6-Dichloro-2-(4'-fluoroanilino)-1,3,5-triazine

Cyanuric chloride (1.844 g, 10 mmol) was dissolved in acetonitrile (20 mL). The solution was cooled to −20° C. A solution of 4-fluoroaniline (1.1 g, 10 mmol) and triethylamine (1.0 g, 10 mmol) was slowly added. After 1 hour at −20° C. the solvent was removed in vacuo and the residue was taken up in ethyl acetate (150 mL). The solution was washed with water (1×50 mL) and brine (1×50 mL), dried ($Na_2SO_4$) and evaporated in vacuo. The residue was recrystallised from ethyl acetate/hexane to give an off white solid identified as 4,6-dichloro-2-(4'-fluoroanilino)-1,3,5-triazine 1.7 g, 6.0 mmol, 60%).

B. 1-[N-2'-(tert-butyloxycarbonyl)-N-2"-(6-Chloro-4-(4'-fluoroanilino)-1,3,5-triazinyl aminoethyl)glycinyl)]thiomorpholine 1-[N-2'-(tert-butyloxycarbonyl)aminoethyl)-glycinyl]thiomorpholine (100 mg, 0.3 mmol) was dissolved in dichloromethane (30 mL). To this solution was added 4,6-dichloro-2-(4'-fluoroanilino)-1,3,5-triazine (90 mg, 0.3 mmol) and triethylamine (50 mg, 0.5 mmol). After 2 hours at room temperature the solvent was removed in vacuo and the residue was taken up in ethyl acetate (150 mL). This solution was washed with water (2×30 mL) and brine (1×30 mL), dried ($Na_2SO_4$) and evaporated in vacuo to give a yellow oil. The residue was purified by flash chromatography (eluant: 60% ethyl acetate, 40% pet. ether) to give a white solid identified as 1-[N-2'-(tert-butyloxycarbonyl)-N-2"-(6-chloro-4-(4'-fluoroanilino)1,3,5-triazinyl aminoethyl)glycinyl)]thiomorpholine (20 mg, 0.032 mmol, 11%).

C. 1-[N-2"-(6-Chloro-4-(4'-fluoroanilino)-1,3,5-triazinyl)aminoethyl)glycinyl)]thiomorpholine dihydrochloride 1-[N-2'-(tert-butyloxycarbonyl)-N-2"-(6-chloro-4-(4'-fluoroanilino)-1,3,5-triazinyl aminoethyl)glycinyl)]thiomorpholine (18.8 mg, 0.03 mmol) was dissolved in 4M HCl/dioxan (20 mL). After 1 h at room temperature the solvent was removed in vacuo. The residue was lyophilised from water to give a white solid identified as 1-[N-2"-(6-Chloro-4-(4'-fluoroanilino)-1,3,5-triazinyl)aminoethyl)glycinyl)]thiomorpholine dihydrochloride (18 mg, 0.03 mmol, 100%).
$[M+H]^+=526.4$

TABLE 9

| Ex No | X | a | R |
|---|---|---|---|
| 1289 | S | 1 | isobutyl |
| 1290 | $CF_2$ | | |
| 1291 | CHF | 2 | |
| 1292 | S | | |
| 1293 | $CH_2$ | | |
| 1294 | O | | |
| 1295 | S | 1 | 2-ethylhexyl |
| 1296 | $CF_2$ | | |
| 1297 | CHF | 2 | |
| 1298 | S | | |
| 1299 | $CH_2$ | | |
| 1300 | O | | |
| 1311 | S | 1 | 2-phenylethyl |
| 1312 | $CF_2$ | | |
| 1313 | CHF | 2 | |
| 1314 | S | | |
| 1315 | $CH_2$ | | |
| 1316 | O | | |
| 1317 | S | 1 | 2-cyclohexylethyl |
| 1318 | $CF_2$ | | |
| 1319 | CHF | 2 | |
| 1320 | O | | |

TABLE 9-continued
| Ex No | X | a | R |
|---|---|---|---|
| 1321 | S | 1 | 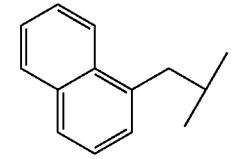 |
| 1322 | CF₂ | | |
| 1323 | CHF | 2 | |
| 1324 | S | | |
| 1325 | CH₂ | | |
| 1326 | O | | |
| 1327 | S | 1 | 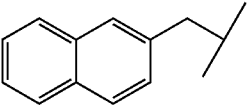 |
| 1328 | CF₂ | | |
| 1329 | CHF | 2 | |
| 1330 | S | | |
| 1331 | CH₂ | | |
| 1332 | O | | |
| 1333 | S | 1 | 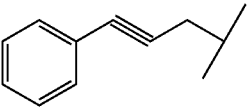 |
| 1334 | CF₂ | | |
| 1335 | CHF | 2 | |
| 1336 | S | | |
| 1337 | CH₂ | | |
| 1338 | O | | |
| 1339 | S | 1 | 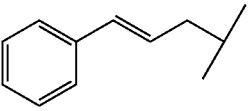 |
| 1340 | CF₂ | | |
| 1341 | CHF | 2 | |
| 1342 | S | | |
| 1343 | CH₂ | | |
| 1344 | O | | |
| 1345 | S | 1 | 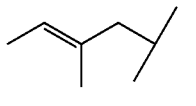 |
| 1346 | CF₂ | | |
| 1347 | CHF | 2 | |
| 1348 | S | | |
| 1349 | CH₂ | | |
| 1350 | O | | |
| 1351 | S | 1 | 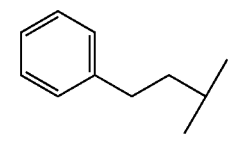 |
| 1352 | CF₂ | | |
| 1353 | CHF | 2 | |
| 1354 | S | | |
| 1355 | CH₂ | | |
| 1356 | O | | |
| 1357 | S | 1 | 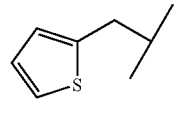 |
| 1358 | CF₂ | | |
| 1359 | CHF | 2 | |
| 1360 | S | | |
| 1361 | CH₂ | | |
| 1362 | O | | |
| 1363 | S | 1 | 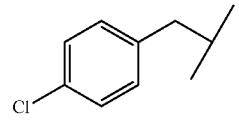 |
| 1364 | CF₂ | | |
| 1365 | CHF | 2 | |
| 1366 | S | | |
| 1367 | CH₂ | | |
| 1368 | O | | |
| 1369 | S | 1 | 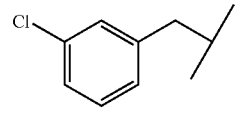 |
| 1370 | CF₂ | | |
| 1371 | CHF | 2 | |
| 1372 | S | | |
| 1373 | CH₂ | | |
| 1374 | O | | |
| 1375 | S | 1 | 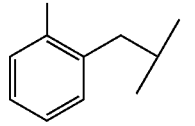 |
| 1376 | CF₂ | | |
| 1377 | CHF | 2 | |
| 1378 | S | | |
| 1379 | CH₂ | | |
| 1380 | O | | |
| 1381 | S | 1 | 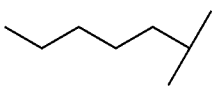 |
| 1382 | CF₂ | | |
| 1383 | CHF | 2 | |
| 1384 | S | | |
| 1385 | CH₂ | | |
| 1386 | O | | |
| 1387 | S | 1 | 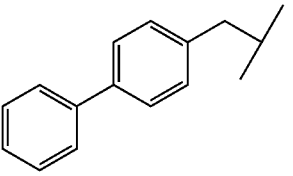 |
| 1388 | CF₂ | | |
| 1389 | CHF | 2 | |
| 1390 | S | | |
| 1391 | CH₂ | | |
| 1392 | O | | |
| 1393 | S | 1 | 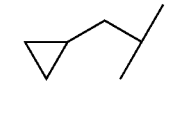 |
| 1394 | CF₂ | | |
| 1395 | CHF | 2 | |
| 1396 | S | | |
| 1397 | CH₂ | | |
| 1398 | O | | |
| 1399 | S | 1 | 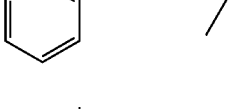 |
| 1400 | CF₂ | | |
| 1401 | CHF | 2 | |
| 1402 | S | | |
| 1403 | CH₂ | | |
| 1404 | O | | |
| 1405 | S | 1 | 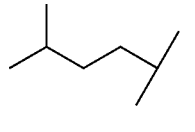 |
| 1406 | CF₂ | | |
| 1407 | CHF | 2 | |
| 1408 | S | | |
| 1409 | CH₂ | | |
| 1410 | O | | |
| 1411 | S | 1 |  |
| 1412 | CF₂ | | |
| 1413 | CHF | 2 | |
| 1414 | S | | |
| 1415 | CH₂ | | |
| 1416 | O | | |
| 1417 | S | 1 | 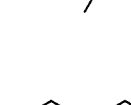 |
| 1418 | CF₂ | | |
| 1419 | CHF | 2 | |
| 1420 | S | | |
| 1421 | CH₂ | | |
| 1422 | O | | |
| 1423 | S | 1 | 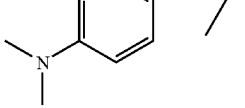 |
| 1424 | CF₂ | | |
| 1425 | CHF | 2 | |
| 1426 | S | | |
| 1427 | CH₂ | | |
| 1428 | O | | |

TABLE 9-continued

Structure: H₂N-CH(CH₂CH₂-NHR)-C(=O)-N(ring with (CH₂)ₐ and X)

| Ex No | X | a | R |
|---|---|---|---|
| 1429 | S | 1 | 4-(acetyloxy)benzyl-CH(CH₃)- |
| 1430 | CF₂ | 2 | |
| 1431 | CHF | 2 | |
| 1432 | S | | |
| 1433 | CH₂ | | |
| 1434 | O | | |

TABLE 10

Structure: RHN-CH₂CH₂-NH-CH₂-C(=O)-N(ring with (CH₂)ₐ and X)

| Ex No | X | a | R |
|---|---|---|---|
| 1614 | S | 1 | sec-pentyl branched |
| 1615 | CF₂ | 2 | |
| 1616 | S | | |
| 1617 | CH₂ | | |
| 1618 | S | 1 | 3-ethyl-branched alkyl |
| 1619 | CF₂ | 2 | |
| 1620 | S | | |
| 1621 | CH₂ | | |
| 1622 | S | 1 | phenyl-CH₂-CH(CH₃)- |
| 1623 | CF₂ | 2 | |
| 1624 | S | | |
| 1625 | CH₂ | | |
| 1626 | S | 1 | cyclohexyl-CH₂-CH(CH₃)- |
| 1627 | CF₂ | 2 | |
| 1628 | S | | |
| 1629 | CH₂ | | |
| 1630 | S | 1 | naphthalen-1-yl-CH₂-CH(CH₃)- |
| 1631 | CF₂ | 2 | |
| 1632 | S | | |
| 1633 | CH₂ | | |
| 1634 | S | 1 | naphthalen-2-yl-CH₂-CH(CH₃)- |
| 1635 | CF₂ | 2 | |
| 1636 | S | | |
| 1637 | CH₂ | | |
| 1638 | S | 1 | phenyl-C≡C-CH₂-CH(CH₃)- |
| 1639 | CF₂ | 2 | |
| 1640 | S | | |
| | CH₂ | | |

TABLE 10-continued

| Ex No | X | a | R |
|---|---|---|---|
| 1642 | S | 1 | phenyl-CH=CH-CH₂-CH(CH₃)- |
| 1643 | CF₂ | 2 | |
| 1644 | S | | |
| 1645 | CH₂ | | |
| 1646 | S | 1 | (CH₃)CH=C(CH₃)-CH₂-CH(CH₃)- |
| 1647 | CF₂ | 2 | |
| 1648 | S | | |
| 1649 | CH₂ | | |
| 1650 | S | 1 | phenyl-CH₂CH₂-CH(CH₃)- |
| 1651 | CF₂ | 2 | |
| 1652 | S | | |
| 1653 | CH₂ | | |
| 1654 | S | 1 | thiophen-2-yl-CH₂-CH(CH₃)- |
| 1655 | CF₂ | 2 | |
| 1656 | S | | |
| 1657 | CH₂ | | |
| 1658 | S | 1 | 4-chlorophenyl-CH₂-CH(CH₃)- |
| 1659 | CF₂ | 2 | |
| 1660 | S | | |
| 1661 | CH₂ | | |
| 1662 | S | 1 | 3-chlorophenyl-CH₂-CH(CH₃)- |
| 1663 | CF₂ | 2 | |
| 1664 | S | | |
| 1665 | CH₂ | | |
| 1666 | S | 1 | 2-chlorophenyl-CH₂-CH(CH₃)- |
| 1667 | CF₂ | 2 | |
| 1668 | S | | |
| 1669 | CH₂ | | |
| 1670 | S | 1 | n-hexyl-CH(CH₃)- (sec-heptyl) |
| 1671 | CF₂ | 2 | |
| 1672 | S | | |
| 1673 | CH₂ | | |
| 1674 | S | 1 | 4-biphenyl-CH₂-CH(CH₃)- |
| 1675 | CF₂ | 2 | |
| 1676 | S | | |
| 1677 | CH₂ | | |
| 1678 | S | 1 | cyclopropyl-CH₂-CH(CH₃)- |
| 1679 | CF₂ | 2 | |
| 1680 | S | | |
| 1681 | CH₂ | | |
| 1682 | S | 1 | phenyl-CH₂CH₂CH₂-CH(CH₃)- |
| 1683 | CF₂ | 2 | |
| 1684 | S | | |
| 1685 | CH₂ | | |

TABLE 10-continued

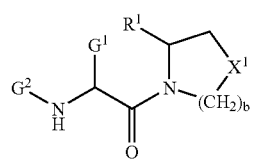

| Ex No | X | a | R |
|---|---|---|---|
| 1686 | S | 1 | |
| 1687 | CF$_2$ | 2 | |
| 1688 | S | | |
| 1689 | CH$_2$ | | |
| 1690 | S | 1 | |
| 1691 | CF$_2$ | 2 | |
| 1692 | S | | |
| 1693 | CH$_2$ | | |
| 1694 | S | 1 | |
| 1695 | CF$_2$ | 2 | |
| 1696 | S | | |
| 1697 | CH$_2$ | | |
| 1698 | S | 1 | |
| 1699 | CF$_2$ | 2 | |
| 1700 | S | | |
| 1701 | CH$_2$ | | |
| 1702 | S | 1 | |
| 1703 | CF$_2$ | 2 | |
| 1704 | S | | |
| 1705 | CH$_2$ | | |

The invention claimed is:

1. A compound according to formula 1, or a pharmaceutically acceptable salt thereof,

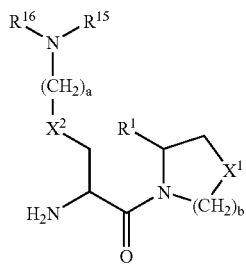

wherein:
either $G^1$ is —CH$_2$—X$^2$—(CH$_2$)$_a$-G$^3$ and $G^2$ is H, or $G^2$ is —CH$_2$—(CH$_2$)$_a$-G$^3$ and $G^1$ is H;
$G^3$ is a group according to formula 4;

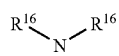

a is 0, 1 or 2;
b is 1;
$X^1$ is CH$_2$;
$X^2$ is CH$_2$;
$R^1$ is H;
$R^{15}$ and $R^{16}$ are independently selected from H, alkyl, alkenyl, aralkyl, aryl and —CH$_2$-L-R$^{17}$ or $R^{15}$ and $R^{16}$ together form a group according to formula 5, formula 6 or formula 7;

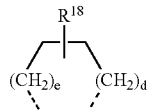

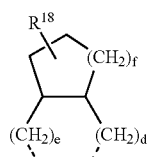

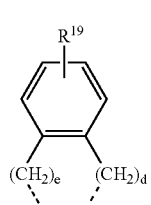

$R^{17}$ is selected from H, alkyl and aryl;
$R^{18}$ is H;
$R^{19}$ is H;
L is selected from a covalent bond, CH=CH, C≡C and —C$_6$H$_4$—;
d and e are selected from 0, 1, 2 and 3 such that d+e is 3, 4 or 5; and
f is 2;
provided that $R^{15}$ and $R^{16}$ are not both H.

2. A compound according to formula 12, or a pharmaceutically acceptable salt thereof, wherein:
a is 0, 1 or 2;
b is 1;
$X^1$ is CH$_2$;
$X^2$ is CH$_2$;
$R^1$ is H,
$R^{15}$ and $R^{16}$ are each independently selected from H, alkyl, alkenyl, aralkyl, aryl and CH$_2$-L-R$^{17}$;
or $R^{15}$ and $R^{16}$ together are a group according to formula 5, a group according to formula 6 or a group according to formula 7;

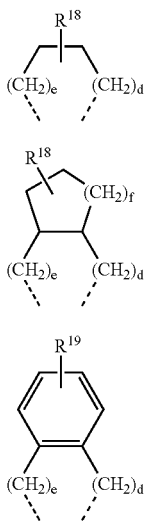

$R^{17}$ is selected from H, alkyl and aryl;
$R^{18}$ is H;
$R^{19}$ is H;
L is selected from a covalent bond, CH=CH, C≡C and —C6H4—;
d and e are selected from 0, 1, 2 and 3 such that d+e is 3, 4 or 5; and
f is 2;
provided that when $R^{15}$ and $R^{16}$ are both H and b is 1 then $X^1$ is not S or $CH_2$.

3. A compound according to claim 2 wherein a is 1.

4. A compound according to claim 2 wherein a is 2.

5. A compound according to formula 13, or a pharmaceutically acceptable salt thereof,

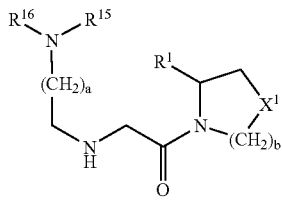

wherein:
a is 1 or 2;
b is 1;
$X^1$ is $CH_2$;
$R^1$ H;
$R^{15}$ and $R^{16}$ are each independently selected from H, alkyl, alkenyl, aralkyl, aryl and $CH_2$-L-$R^{17}$;
or $R^{15}$ and $R^{16}$ together are a group according to formula 5, a group according to Formula 6 or a group according to formula 7;

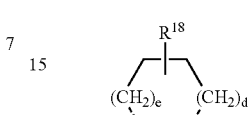

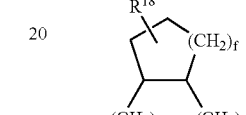

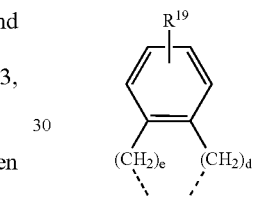

$R^{17}$ is selected from H, alkyl and aryl;
$R^{18}$ is H;
$R^{19}$ is H;
L is selected from a covalent bond, CH=CH, C≡C and —$C_6H_4$—;
d and e are selected from 0, 1, 2 and 3 such that d+e is 3, 4 or 5; and
f is 2.

6. A compound according to claim 5 wherein a is 1.

7. A pharmaceutical composition comprising a compound according to claim 1.

* * * * *